(12) United States Patent
Harth et al.

(10) Patent No.: US 11,305,018 B2
(45) Date of Patent: *Apr. 19, 2022

(54) LINEAR POLYESTER AND SEMI-LINEAR GLYCIDOL POLYMER SYSTEMS: FORMULATION AND SYNTHESIS OF NOVEL MONOMERS AND MACROMOLECULAR STRUCTURES

(71) Applicant: Vanderbilt University, Nashville, TN (US)

(72) Inventors: Eva M. Harth, Nashville, TN (US); Dain B. Beezer, Nashville, TN (US); GuangZhao Li, Nashville, TN (US); Benjamin R. Spears, Nashville, TN (US); David M. Stevens, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/801,014

(22) Filed: Feb. 25, 2020

(65) Prior Publication Data

US 2020/0237918 A1 Jul. 30, 2020

Related U.S. Application Data

(63) Continuation of application No. 15/663,363, filed on Jul. 28, 2017, now Pat. No. 10,610,598, which is a
(Continued)

(51) Int. Cl.
| | | |
|---|---|---|
| A61K 47/32 | (2006.01) | |
| A61K 47/34 | (2017.01) | |
| C08G 65/22 | (2006.01) | |
| A61K 9/00 | (2006.01) | |
| A61K 9/50 | (2006.01) | |

(Continued)

(52) U.S. Cl.
CPC ............ *A61K 47/34* (2013.01); *A61K 9/0019* (2013.01); *A61K 9/5031* (2013.01); *A61K 47/32* (2013.01); *C08G 64/42* (2013.01); *C08G 65/00* (2013.01); *C08G 65/002* (2013.01); *C08G 65/22* (2013.01); *C08G 65/2615* (2013.01);

(Continued)

(58) Field of Classification Search
None
See application file for complete search history.

(56) References Cited

U.S. PATENT DOCUMENTS

| | | |
|---|---|---|
| 4,965,342 A | 10/1990 | Vandenberg et al. |
| 9,161,983 B2 | 10/2015 | Harth et al. |

(Continued)

OTHER PUBLICATIONS

Dworak et al., Macromol. Chem. Phys., 1995, 196(6), pp. 1963-1970. (Year: 1995).*

(Continued)

*Primary Examiner* — Brian Gulledge
(74) *Attorney, Agent, or Firm* — Cooley LLP; J. Dean Farmer; Ramsey M. Hilton

(57) ABSTRACT

Disclosed herein are glycidol-based polymers, nanoparticles, and methods related thereto useful for drug delivery. This abstract is intended as a scanning tool for purposes of searching in the particular art and is not intended to be limiting of the present invention.

11 Claims, 22 Drawing Sheets

Related U.S. Application Data continuation of application No. 14/918,115, filed on Oct. 20, 2015, now Pat. No. 9,757,463, which is a continuation of application No. 13/919,916, filed on Jun. 17, 2013, now Pat. No. 9,161,983.

(60) Provisional application No. 61/660,675, filed on Jun. 15, 2012.

(51) Int. Cl.
*C08G 64/42* (2006.01)
*C08G 65/00* (2006.01)
*C08G 65/26* (2006.01)
*C08G 65/332* (2006.01)
*C08G 65/334* (2006.01)
*C08G 65/34* (2006.01)

(52) U.S. Cl.
CPC ..... *C08G 65/3326* (2013.01); *C08G 65/3348* (2013.01); *C08G 65/34* (2013.01)

(56) References Cited

U.S. PATENT DOCUMENTS

| | | |
|---|---|---|
| 9,745,419 B2 | 8/2017 | Harth et al. |
| 9,757,463 B2 | 9/2017 | Harth et al. |
| 10,308,763 B2 | 6/2019 | Harth et al. |
| 10,610,598 B2 | 4/2020 | Harth et al. |
| 2011/0262531 A1 | 10/2011 | Pohlmann et al. |
| 2014/0005278 A1 | 1/2014 | Harth et al. |
| 2015/0210805 A1 | 7/2015 | Harth et al. |
| 2016/0206743 A1 | 7/2016 | Harth et al. |
| 2018/0125983 A1 | 5/2018 | Harth et al. |
| 2018/0134843 A1 | 5/2018 | Harth et al. |
| 2020/0087454 A1 | 3/2020 | Harth et al. |

OTHER PUBLICATIONS

Non-final Office Action dated Sep. 30, 2020 for U.S. Appl. No. 16/394,958, filed Apr. 25, 2019 and published as US 2020/0087454 A1 on Mar. 19, 2020 (Inventor—Harth, et al.).
Aggarwal VK, et al. (1998) (1R,3R)-2-Methylene-1,3-dithiolane 1,3-dioxide: a highly reactive and highly selective chiral ketene equivalent in cycloaddition reactions with a broad range of dienes. J. Chem. Soc., Perkin Trans. 1, 2771-2782.
Alconcel SNS, et al. (2011) FDA-approved poly(ehtylene glycol)-protein conjugate drugs. Polymer Chemistry, 2(7): 1442-1448.
Boyer C, et al. (2007) Well-defined protein-polymer conjugates via in situ RAFT polymerization. Journal of the American Chemical Society, 129(220: 7145-7154.
Burakowska E, et al. (2009) Photoresponsive Crosslinked Hyperbranched Polyglycerols as Smart Nanocarriers for Guest Binding and Controlled Release. Small, 15(19): 2199-2204.
Calderon M, eta l. (2010) Dendritic Polyglycerols for Biomedical Applications. Advanced Materials, 22(2): 190-218.
De P, et al. (2008) Temperature-regulated activity of responsive polymer-protein conugates prepared by grafting-from via RAFT polymerization. J. Am. Chem. Soc., 130(34)L 11288-11289.
Debaig C, et al. (2002) Synthesis of linear and cyclic polyglycerols. Polyglyceryled surfactants: synthesis and characterization. Ocl-Oleagineux Corps Gras Lipides, 9(2-3): 155-162.
Dworak A, et al. (1995) Cationic Polymerization of Glycidol—Polymer Structure and polymerization Mechanism. Macromolecular Chemistry and Physics, 196(6): 1963-1970.
Ebwein B, et al. (1996) Anionic polymerization of oxirane in the presence of the polyiminophosphazene base t-Bu-P4. Macromolecular Rapid Communications, 17(2): 143-148.
Fischer W, et al. (2010) Dendritic Polyglycerols with Oligoamine Shells Show Low Toxicity and High siRNA Transfection Efficiency in Vitro. Bioconjugate Chemistry, 21(10): 1744-1752.

Fitton AO, et al. (1987) Synthesis of Simple Oxetanes Carrying Reactive 2-Substituents. Synthesis-Stuttgart, 12: 1140-1142.
Gervais M, et al. (2011) Linear High Molar Mass Polyglycidol and its Direct .alpha.-Azido Functionalization. Macromolecular Symposia, 308(1): 11.
Gervais M, et al. (2011) Synthesis of Linear High Molar Mass Glycidol-Based Polymers by Monomer-Activated Anionic Polymerization. Macromolecules, 43(4): 1778-1784.
Gunasekaran K, et al. (2011) Conjugation of siRNA with Comb-Type PEG Enhances Serum Stability and Gene Silencing Efficiency. Macromolecular Rapid Communications, 32(8): 654-659.
Haag R, et al. (2000) An approach to glycerol dendrimers and pseudo-dendritic polyglycerols. J. Am. Chem. Soc., 122(12): 2954-2955.
Haag R, et al. (2001) Polymeric nanocapsules based on core-shell0type architectures in hyperbranched polyglycerols. Abstracts of Papers of the American Chemical Society, 221: U363-U364.
Hamilton SK, eta l. (2008) Effective delivery of IgG-antibodies into infected cells via dendritic molecular transporter conjugate IgGMT. Molecular Biosystems, 4(12): 1209-1211.
Khan M, et al. (2003) Hyperbranched polyglycidol on Si-SiO2 surfaces via surface-initiated polymerization. Macromolecules, 36(140): 5088-5093.
Maminski ML, eta l. (2011) Fast-curing polyurethane adhesives derived from environmentally friendly hyperbranched polyglycerols—The effect of macromonomer structures. Biomass & Bioenergy, 35(10): 4464-4468.
Mendrek A, et al. (2010) Amphiphilic behaviour of poly(glycidol)-based macromonomers and its influence on homo-polymerisation in water and in water/benzene mixture. Polymer, 51(2): 342-354.
Montarnal D, et al. (2011) Silica-Like Malleable Materials from Permanent Organic Networks. Science, 334: 965-968.
Mugabe C, et al. (2011) Development and in vitro characterization of paclitaxel and docetaxel loaded into hydrophobically derivatized hyperbranched polyglycerols. International Journal of Pharmaceutics, 404(1-2): 238-249.
Mugabe C, et al. (2011) In Vitro and In Vivo Evaluation of Intravesical docetaxel Loaded Hydrophobically Derivatized Hyperbranched Polyglycerols in an Orthotopic Model of Bladder Cancer. Biomacrocoleules, 12(4): 949-960.
Mugabe C, et al. (2011) In Vivo Evaluation of Mucoadhesive Nanoparticulate Docetaxel and Paclitaxel Loaded Hydrophobically Derivatized Hyperbranched polyglycerols for Intravesical Bladder Cancer Therapy. European Urology Supplements, 10(2): 166-167.
Mugabe C, et al. (2009) Paclitaxel incorporated in hydrophobically derivatized hyperbranched polyglycerols for intravesical bladder cancer therapy. Bji International, 103(7): 978-986.
Pangborn AB. (1996) Safe and Convenient Procedure for Solvent Purification. Organometallics, 15: 1518-1520.
Parrot MC, et al. (2012) Drug Delivery: Relieving PEGylation. Nature Chemistry, 4(1): 13-14.
Petchsuk et al., Poly. Degrad. Stability, 2009, vol. 94, pp. 1700-1706.
Rangelov S, et al. (2007) Hydrodynamic behavior of high molar mass linear polyglycidol in dilute aqueous solution. Journal of Physical Chemistry B, 111(38): 11127-11133.
Sizovs A, eta l. (2010) Carbohydrate Polymers for Nonviral Nucleic Acid Delivery. Topics in Current Chemistry, 296(296): 131-190.
Spears BR. (2013) Controlled branching of polyglycidol and formation of protein-glycidol bioconjugates via a graft-from approach with "PEG-like"arms. Chem. Commun., 49, 2394-2396.
Steinhilber D, eta l. (2011) Hyperbranched polyglycerols on the nanometer and micrometer scale. Biomaterials, 32(5): 1311-1316.
Sunder A, et al. (1999) Controlled synthesis of hyperbranched polyglycerols by ring-opening multibranching polymerization. Macromolecules, 32(13): 4240-4246.
Sunder A, et al. (2000) Copolymers of glycidol and glycidyl ethers: Design of branched polyether polyols by combination of latent cyclic AB(2) and ABR monomers. Macromolecules, 33(21): 7682-7692.
Sunder A, et al. (2000) Hyperbranched polyglycerols by ring-opening multibranching polymerization. Macromolecular Symposial, 153: 187-196.

(56) References Cited

OTHER PUBLICATIONS

Sunder et al., Macromolecules, 2000, 33(21), pp. 7682-7692.
Tokar R, et al. (1994) Cationic Polymerization of Glucidol—Coexistence of the Activated Monomer and Active Chain-End Mechanism. Macromolecules, 27(2): 320-322.
van der Ende AE, et al. (2008) Approach to formation of multifunctional polyester particles in controlled nanoscopic dimensions. J. Am. Chem. Soc., 130(27): 8706-8713.
van der Ende AE, et al. (2010) "Click" Reactions: Novel Chemistries for Forming Well-defined Polyester Nanoparticles. Macromolecules, 43(13): 5665-5671.
van der Ende AE, et al. (2010) Linear release nanoparticle devices for advanced targeted cancer therapies with increased efficacy. Polymer Chemistry, 1(1): 93-96.
van der Ende AE, et al. (2009) Tailored polyester nanoparticles: post-modification with dendritic transporter and targeting units via reductive amination and thiol-ene chemistry. Soft Matter, 5(7): 1417-1425.
Wang SX, et al. (2008) Growing hyperbranched polyglycerols on magnetic nanoparticles to resist nonspecific adsorption of proteins. Colloids and Surfaces B-Biointerfaces, 67(1): 122-126.
Wang et al., Colloids and Surfaces B-Biointerfaces, 2008, 67(1), pp. 122-126.
Wilms D, et al. (2009) Advanced control over glycidol polymerization: Hyperbranched polyglycerols via macroinitiators. Abstracts of Papers of the American Chemical Society, 237.
Wilms D, et al. (2010) Hyperbranched PEG by Random Copolymerization of Ethylene Oxide and Glycidol. Macromolecular Rapid Communications, 31(20): 1811-1815.
Wilms D, et al. (2010) Hyperbranched Polyglycerols: From the Controlled Synthesis of Biocompatible Polyether Polyols to Multipurpose Applications. Acc Chem Res.; 43(1):129-41.
Ye L, et al. (2011) Synthesis and Characterization of Carboxylic Acid Conjugated, Hydrophobically Derivatized, Hyperbranched Polyglycerols as Nanoparticulate Drug Carriers for Cisplatin. Biomacromoleculesl, 12(1): 145-155.
Zhang JG, et al. (2007) RGD-substituted high molecular weight hyper-branched polyglycerols (HPG) are effective platelet inhibitors. Blood, 110(11): 281A-281A.
Zhang JG, et al. (2008) Conjugation to hyperbranched polyglycerols improves RGD-mediated inhibition of platelet function in vitro. Bioconjugate Chemistry, 19(6): 1241-1247.
Zhang XJ, et al. (2011) beta-Cyclodextrin grafting hyperbranched polyglycerols as carriers for nasal insulin delivery. Carbohydrate Polymers, 84(4): 1419-1425.
Zinelaabadine et al., A Simple and Efficient Green Method for the Deprotection of N-Boc in Various Structurally Diverse Amines under Water-mediated Catalyst-free Conditions, Int. J. Chem., 2012, 4(3), pp. 73-79.
Requirement for Restriction/Election dated Mar. 4, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (9 pages).
Response to Requirement for Restriction/Election filed on May 5, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (15 pages).
Requirement for Restriction/Election dated Jul. 16, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (10 pages).
Response to Requirement for Restriction/Election filed on Aug. 6, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (16 pages).
Non-Final Office Action dated Sep. 19, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (7 pages).
Response to Non-Final Office Action filed on Dec. 29, 2014, for U.S. Appl. No. 13/919,916, filed Jun. 17, 2013 and published as US 2014-0005278 A1 on Jan. 2, 2014 (Inventor—Harth, et al // Applicant—Vanderbilt University) (21 pages).
Final Office Action dated Jan. 23, 2015, for U.S. Appl. No. 13/919,916, filed Jun. 17, 2013 and published as US 2014-0005278 A1 on Jan. 2, 2014 (Inventor—Harth, et al // Applicant—Vanderbilt University) (15 pages).
Response to Final Office Action filed on May 26, 2015, for U.S. Appl. No. 13/919,916, filed Jun. 17, 2013 and published as US 2014-0005278 A1 on Jan. 2, 2014 (Inventor—Harth, et al // Applicant—Vanderbilt University) (8 pages).
Supplemental Response to Final Office Action filed on Jun. 1, 2015, for U.S. Appl. No. 13/919,916, filed Jun. 17, 2013 and published as US 2014-0005278 A1 on Jan. 2, 2014 (Inventor—Harth, et al // Applicant—Vanderbilt University) (6 pages).
Notice of Allowance dated Jun. 8, 2015, for U.S. Appl. No. 13/919,916, filed Jun. 17, 2013 and published as US 2014-0005278 A1 on Jan. 2, 2014 (Inventor—Harth, et al // Applicant—Vanderbilt University) (5 pages).
Issue Notification dated Sep. 30, 2015, for U.S. Appl. No. 13/919,916, filed Jun. 17, 2013 and published as US 2014-0005278 A1 on Jan. 2, 2014 (Inventor—Harth, et al // Applicant—Vanderbilt University) (5 pages).
Requirement for Restriction/Election dated Aug. 12, 2016, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (9 pages).
Response to Requirement for Restriction/Election dated Oct. 12, 2016, to the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (13 pages).
Non Final Rejection dated Nov. 4, 2016, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (10 pages).
Response to Non Final Rejection dated Apr. 4, 2017, to the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (10 pages).
Notice of Allowance dated Apr. 24, 2017, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (7 pages).
Amendment after Notice of Allowance (Rule 312) dated Apr. 25, 2017, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (3 pages).
Response to Amendment under (Rule 312) dated May 9, 2017, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (2 pages).
Issue Notification dated Aug. 23, 2017, by the USPTO for U.S. Appl. No. 14/918,115, filed Oct. 20, 2015 now U.S. Pat. No. 9,757,463 on Sep. 12, 2017 (Inventor—Harth, et al // Applicant—Vanderbilt University) (1 page).
Requirement for Restriction or Election dated Jan. 14, 2016 for U.S. Appl. No. 14/605,602, filed Jan. 26, 2015 and published as US 2015-0210805-A1 on Jul. 30, 2015 (Applicant—Vanderbilt University // Inventor—Harth, et al.) (6 pages).
Response to Requirement for Restriction or Election and Amendment filed on Mar. 25, 2016 for U.S. Appl. No. 14/605,602, filed Jan. 26, 2015 and published as US 2015-0210805-A1 on Jul. 30, 2015 (Applicant—Vanderbilt University // Inventor—Harth, et al.) (8 pages).
Non Final Rejection dated Apr. 8, 2016 for U.S. Appl. No. 14/605,602, filed Jan. 26, 2015 and published as US 2015-0210805-A1 on Jul. 30, 2015 (Applicant—Vanderbilt University // Inventor—Harth, et al.) (10 pages).
Response to Non Final Rejection dated Oct. 10, 2016 for U.S. Appl. No. 14/605,602, filed Jan. 26, 2015 and published as US 2015-0210805-A1 on Jul. 30, 2015 (Applicant—Vanderbilt // Inventor—Harth, et al.) (10 pages).

(56) References Cited

OTHER PUBLICATIONS

Final Rejection filed on Nov. 3, 2016 for U.S. Appl. No. 14/605,602, filed Jan. 26, 2015 and published as US 2015-0210805-A1 on Jul. 30, 2015 (Applicant—Vanderbilt University // Inventor—Harth, et al.) (8 pages).
Response to Final Rejection dated Apr. 24, 2017 for U.S. Appl. No. 14/605,602, filed Jan. 26, 2015 and published as US 2015-0210805-A1 on Jul. 30, 2015 (Applicant—Vanderbilt University // Inventor—Harth, et al.) (7 pages).
Notice of Allowance filed on May 2, 2017 for U.S. Appl. No. 14/605,602, filed Jan. 26, 2015 and published as US 2015-0210805-A1 on Jul. 30, 2015 (Applicant—Vanderbilt University // Inventor—Harth, et al.) (8 pages).
Issue Notification filed on Aug. 9, 2017 for U.S. Appl. No. 14/605,602, filed Jan. 26, 2015 and published as US 2015-0210805-A1 on Jul. 30, 2015 (Applicant—Vanderbilt University // Inventor—Harth, et al.) (1 page).
Non Final Rejection was filed on Apr. 6, 2018 for U.S. Appl. No. 15/684,638, filed Aug. 23, 2017 now U.S. Pat. No. 10,308,763 on Jun. 4, 2019 (Inventor—Harth, et al.) (6 page).
Response to Non Final Rejection dated Oct. 4, 2018 for U.S. Appl. No. 15/684,638, filed Aug. 23, 2017 now U.S. Pat. No. 10,308,763 on Jun. 4, 2019 (Inventor—Harth, et al.) (14 page).
Notice of Allowance was filed on Jan. 23, 2019 for U.S. Appl. No. 15/684,638, filed Aug. 23, 2017 now U.S. Pat. No. 10,308,763 on Jun. 4, 2019 (Inventor—Harth, et al.) (8 pages).
Issue Notification was filed on May 15, 2019 for U.S. Appl. No. 15/684,638, filed Aug. 23, 2017 now U.S. Pat. No. 10,308,763 on Jun. 4, 2019 (Inventor—Harth, et al.) (1 page).
Restriction Requirement was filed on Sep. 21, 2018 for U.S. Appl. No. 15/663,363, filed Jul. 28, 2017 now U.S. Pat. No. 10,610,598 on Apr. 7, 2020 (Inventor—Harth, et al.) (5 pages).
Response to Restriction Requirement dated Mar. 14, 2019 for U.S. Appl. No. 15/663,363, filed Jul. 28, 2017 now U.S. Pat. No. 10,610,598 on Apr. 7, 2020 (Inventor—Harth, et al.) (9 pages).
Non Final Rejection was filed on Apr. 10, 2019 for U.S. Appl. No. 15/663,363, filed Jul. 28, 2017 nows U.S. Pat. No. 10,610,598 on Apr. 7, 2020 (Inventor—Harth, et al.) (7 pages).
Response to Non Final Rejection was filed on Oct. 7, 2019 for U.S. Appl. No. 15/663,363, filed Jul. 28, 2017 now U.S. Pat. No. 10,610,598 on Apr. 7, 2020 (Inventor—Harth, et al.) (10 pages).
Notice of Allowance was filed on Nov. 15, 2019 for U.S. Appl. No. 15/663,363, filed Jul. 28, 2017 now U.S. Pat. No. 10,610,598 on Apr. 7, 2020 (Inventor—Harth, et al.) (7 pages).
Amendment after Notice of Allowance dated Dec. 6, 2019 for U.S. Appl. No. 15/663,363, filed Jul. 28, 2017 now U.S. Pat. No. 10,610,598 on Apr. 7, 2020 (Inventor—Harth, et al.) (3 pages).
Response to Amendment after Notice of Allowance dated Jan. 13, 2020 for U.S. Appl. No. 15/663,363, filed Jul. 28, 2017 now U.S. Pat. No. 10,610,598 on Apr. 7, 2020 (Inventor—Harth, et al.) (3 pages).
Issue Notification was filed on Mar. 18, 2020 for U.S. Appl. No. 15/663,363, filed Jul. 28, 2017 now U.S. Pat. No. 10,610,598 on Apr. 7, 2020 (Inventor—Harth, et al.) (1 page).
U.S. Appl. No. 61/660,675, filed Jun. 15, 2012, Eva M. Harth et al.
U.S. Appl. No. 13/919,916 (U.S. Pat. No. 9,161,983), filed Jun. 17, 2013 (Oct. 20, 2015), Eva M. Harth et al.
U.S. Appl. No. 14/918,115 (U.S. Pat. No. 9,757,463), filed Oct. 20, 2015 (Sep. 12, 2017), Eva M. Harth et al.
U.S. Appl. No. 15,663,363 (U.S. Pat. No. 10,610,598), filed Jul. 28, 2017 (Apr. 7, 2020), Eva M. Harth et al.
U.S. Appl. No. 61/755,949, filed Jan. 23, 2013, Eva M. Harth et al.
U.S. Appl. No. 61/931,556, filed Jan. 24, 2014, Eva M. Harth et al.
U.S. Appl. No. 14/605,602 (U.S. Pat. No. 9,745,419), filed Jan. 26, 2015 (Aug. 29, 2017), Eva M. Harth et al.
U.S. Appl. No. 15/684,638, filed Aug. 23, 2017, Eva M. Harth et al.
U.S. Appl. No. 61/822,843, filed May 13, 2013, Eva M. Harth et al.
U.S. Appl. No. 61/992,708, filed May 13, 2013, Eva M. Harth et al.

\* cited by examiner

Two Component Delivery System from Polyglycidol – "Matrix" and Polyester Nanoparticles Polyglycidol Bone Morphogenetic Protein 2

MEK inhibitor (example)

1. Reaction: Amino-Oxy with Keto group

With or without the presence of

2. Reaction: Transesterification with zincacetate under heat. These reactions are reconfigurable and are not "set".

LINEAR POLYESTER AND SEMI-LINEAR GLYCIDOL POLYMER SYSTEMS: FORMULATION AND SYNTHESIS OF NOVEL MONOMERS AND MACROMOLECULAR STRUCTURES

CROSS-REFERENCE TO RELATED APPLICATIONS

This Application is a Continuation of U.S. patent application Ser. No. 15/663,363, filed on Jul. 28, 2017 (now U.S. Pat. No. 10,610,598), which is a Continuation of U.S. patent application Ser. No. 14/918,115 (now U.S. Pat. No. 9,757,463), filed on Oct. 20, 2015, which is a Continuation of U.S. patent application Ser. No. 13/919,916 (now U.S. Pat. No. 9,161,983), filed on Jun. 17, 2013, which claims the benefit of U.S. Provisional Application No. 61/660,675 filed on Jun. 15, 2012, the contents of which are incorporated herein by reference in their entireties.

STATEMENT REGARDING FEDERALLY SPONSORED RESEARCH

This invention was made with government support under grant number EB009223 awarded by the National Institutes of Health. The government has certain rights in the invention.

BACKGROUND

Many highly efficacious drugs have already been created and the main hurdle that these drug molecules have to overcome is their hydrophobicity. Due to this lack of solubility, regardless of the drugs efficacy, the molecules will never be cleared as viable treatment options. Furthermore, biological therapeutics such as antibodies and proteins (e.g., growth factors) are not stable for a prolonged time in the biological environment and impedes their activity and therapeutic efficacy. Moreover, it has been found that therapeutics can work very efficiently together and enhance the therapeutic outcome known as the synergistic effect.

Thus, there remains a need for delivery systems that address hydrophobicity and/or lack of solubility. In view of the need of delivery systems that deliver drugs of different nature, can control the kinetics of the delivery, and react to external stimuli, multifaceted delivery systems are being developed. The combinations of 3-D nanoparticles are designed to deliver small molecules that are imbedded in non-crosslinked or crosslinked matrices are of interest. Additionally, 2-D materials that contain no 3-D nanoparticle materials are crosslinked to hydrophilic networks to be formed in click reactions in hydrophilic and hydrophobic environments. The functionalities in these hydrogel materials allow response to heat, reconfiguring the network but not destroying the structure.

SUMMARY OF THE INVENTION

In accordance with the purpose(s) of the invention, as embodied and broadly described herein, the invention, in one aspect, relates to compounds that can be used in drug delivery, and composition thereof and methods thereof.

Disclosed herein is a polymer comprising repeating units selected from:

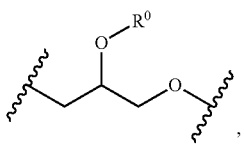
A1

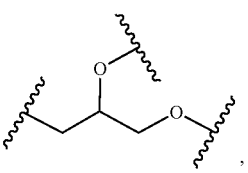
A2

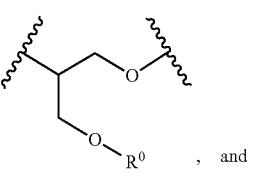
B1, and

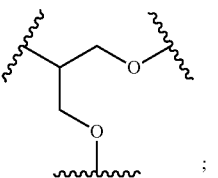
B2;

wherein $R^0$ is selected from H, alkyl, $NH_2$, and $R^1$; wherein $R^1$ comprises a crosslinking functionality; wherein repeating units A1, A2, B1, and B2 account for at least about 50 wgt % of the polymer; and wherein the ratio of (A1+A2):(B1+B2) is greater than 1.

Also disclosed herein is a nanoparticle comprising the disclosed compounds.

Also disclosed is a method for making a polymer, the method comprising the step of polymerizing glycidol in the presence of a tin catalyst.

Also disclosed herein is a method for forming a nanoparticle comprising: a. providing a polymer disclosed herein and crosslinking polymer with crosslinks disclosed herein.

Also disclosed is a drug delivery method comprising the step of administering to a subject a composition comprising a polymer or nanoparticle disclosed herein, in combination with at least one pharmaceutically active agent and/or biologically active agent.

Also disclosed herein is a pharmaceutical composition comprising a polymer or nanoparticle disclosed herein; a pharmaceutically active agent and/or biologically active agent; and a pharmaceutically acceptable earner.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying Figures, which are incorporated in and constitute a part of this specification, illustrate several aspects and together with the description serve to explain the principles of the invention.

Figure 1:
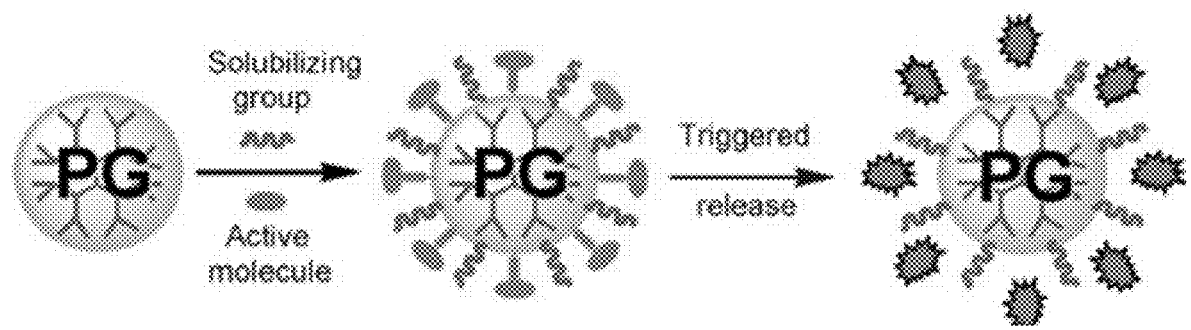
FIG. 1 shows schematic representation of drug-loaded hyperbranched polyglycerols.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "subject" refers to the target of administration, e.g., an animal, such as a human. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for increasing muscle mass prior to the administering step. In some aspects of the disclosed method, the subject has been diagnosed with a need for increasing muscle mass prior to the administering step.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration PPP be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert earners can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polymer refers to one or more —OCH$_2$CH$_2$O— units in the polter, regardless of whether ethylene glycol was used to prepare the polter. Similarly, a sebacic acid residue in a polter refers to one or more —CO(CH$_2$)$_8$CO— moieties in the polter, regardless of whether the residue is obtained by reacting sebacic acid or an ester thereof to obtain the polymer. In certain aspects, a monomer residue in a polymer can also be described as a repeating unit.

As used herein, the term "biologically active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include antiviral agents, vaccines, hormones, antibodies (including active antibody fragments sFv, Fv, and Fab fragments), aptamers, peptide mimetics, functional nucleic acids, therapeutic proteins, peptides, or nucleic acids. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration).

As used herein, the term "pharmaceutically active agent" includes a "drug" or a "vaccine" and means a molecule, group of molecules, complex or substance administered to an organism for diagnostic, therapeutic, preventative medical, or veterinary purposes. This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA). Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, carbonic anhydrase inhibitors, prostaglandin analogs, a combination of an alpha agonist and a beta blocker, a combination of a carbonic anhydrase inhibitor and a beta blocker, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, or a vaccine. In a further aspect, the pharmaceutically active agent can be coumarin, albumin, bromolidine, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthntis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, timol hemihydrate, levobunolol hydrochloride, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists (i.e., alpha adrenergic receptor agonist) such as clonidine, brimonidine tartrate, and apraclonidine hydrochloride; alpha-1-antagonists such as doxazosin and prazosin; anticholinergic/antispasmodic agents such as dicyclomine hydrochloride, scopolamine hydrobromidc, glycopyrrolate, clidinium bromide, flavoxate, and oxybutynin; vasopressin analogues such as vasopressin and desmopressin; prostaglandin analogs such as latanoprost, travoprost, and bimatoprost; cholinergics (i.e., acetylcholine receptor agonists) such as pilocarpine hydrochloride and carbachol; glutamate receptor agonists such as the N-methyl D-aspartate receptor agonist memantine, anti-Vascular endothelial growth factor (VEGF) aptamers such as pegaptanib; anti-VEGF antibodies (including but not limited to anti-VEGF-A antibodies) such as ranibizumab and bevacizumab; carbonic anhydrase inhibitors such as methazolamide, brinzolamide, dorzolamide hydrochloride, and acetazolamide; antiarrhythmic agents such as quinidine, lidocaine, tocainide hydrochloride, mexiletine hydrochloride, digoxin, verapamil hydrochloride, propafenone hydrochloride, flecaimide acetate, procainamide hydrochloride, moricizine hydrochloride, and diisopyramide phosphate; antiparkinsonian agents, such as dopamine, L-Dopa/Carbidopa, selegiline, dihydroergokryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term alkoxyalkyl specifically refers to an alkyl group that is substituted with one or more alkoxy groups, as described below. The term "alkylamino" specifically refers to an alkyl group that is substituted with one or more amino groups, as described below, and the like. When alkyl is used in one instance and a specific term such as "alkylalcohol" is used in another, it is not meant to imply that the term "alkyl" does not also refer to specific terms such as "alkylalcohol" and the like.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polter" as used herein is represented by the formula -$(A^1O(O)C-A^2-C(O)O)_a$— or -$(A^1O(O)C-A^2-OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polter" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "azide" as used herein is represented by the formula —$N_3$.

The term "thiol" as used herein is represented by the formula —SH.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acres Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Polymers

As briefly described herein, the present invention, in various aspects, relates to glycidol-based polymer systems. In a one aspect, as shown below, glycidol is an analog of ethylene glycol. In further aspects, glycidol can be ring opened in different ways, is capable of controlled polymerization, and is inherently hydrophilic due to the presence of a primary hydroxyl functionality. In one aspect, the glycidol polymers can be semi-branched.

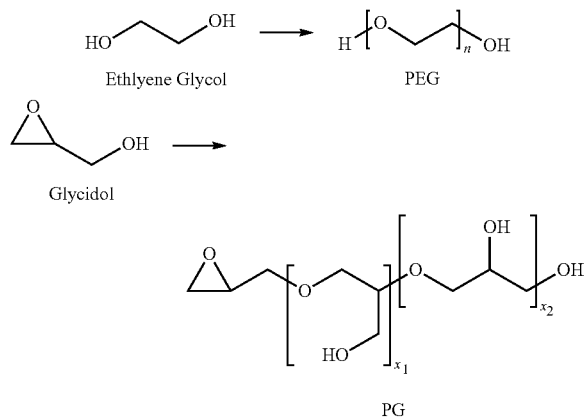

In a further aspect, the semi-branched architectures can be used for transportation of drugs and other biological cargo, as shown in FIG. 1. However, this type of structure presents a number of limitations. For example, the vastly branched systems have limited post-modification, as they only contain an assortment of primary and secondary hydroxyl groups, rather than an assortment of reactive points. In a still further aspect, the random configurations can lead to complications with introducing the intended cargo to the system.

In further aspects, the glycidol based polymer systems comprise linear glycidols. In one aspect, linear glycidols can be accomplished using glycidol derivatives and anionic polymerization methods, as represented by the reaction scheme below.

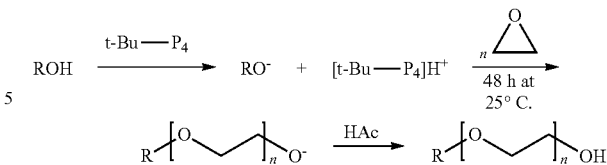

However, this method involves rigorous reaction conditions, is very susceptible to oxygen, and requires numerous purification steps. In a further aspect, this method does not deliver polymer systems with a suitable degradation profile. In a further aspect, the inherent water solubility of poly (glycidol) systems can be utilized to allow a method that will provide more linear poly(glycidol) systems.

Figure 2:
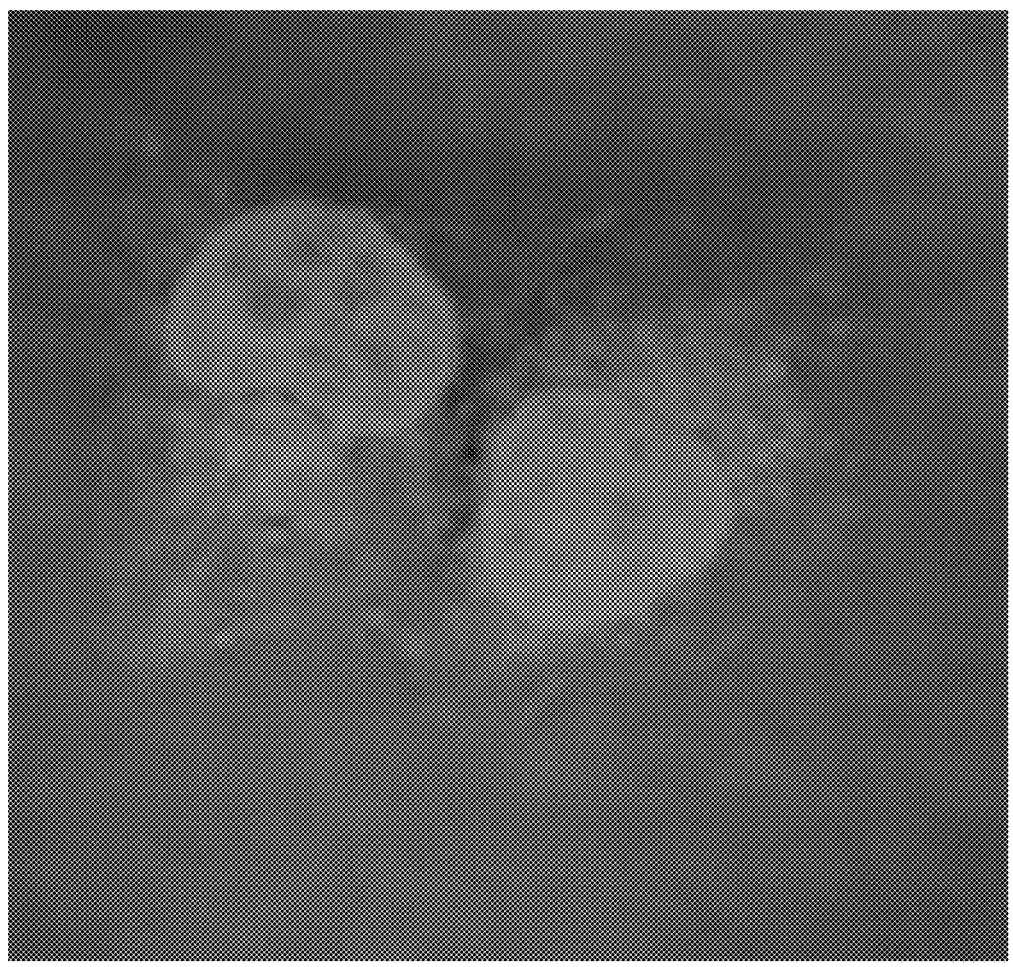
FIG. 2 shows a fluorescent image of polyglycerols loaded with a therapeutic cargo.

In a further aspect, the linear glycidols comprise additional functional group containing co-monomers. In a still further aspect, the additional functional groups can be subsequently cross-linked to form nanoparticle structures. These nanoparticles will imbibe the applicability of the water-soluble glycidol units with the functionality of groups, such as allyl's and epoxides, which are capable of a range of post-modification reactions. In a further aspect, this will allow for the encapsulation of drug molecules followed by the addition of targeting units and/or dyes, as depicted in FIG. 2. In a still further aspect, the addition of this increased functionality provides a variety of nanoparticles that can be tailored to specific needs, as well as structures whose functionality can be verified in a laboratory setting. In an even further aspect, the polymer systems can comprise polyester nanoparticle systems for the transport of hydrophobic drug molecules.

As described above, glycidol's analogous structure to polyethylene glycol, as well as its abundance of primary and secondary hydroxyl groups provides a system that is relatively non-toxic and exceedingly hydrophilic. In various aspects, glycidol-based systems involve the formation of single-step dendrimer like macromolecules that provide the abilities of dendrimers without the painstaking process of dendrimer growth.[2, 4, 5, 18-22] In a further aspect, glycidol's success relates to its latent $AB_2$ monomer type. Thus, in a still further aspect, the glycidol monomer does not become a true $AB_2$ type monomer until it has undergone ring opening. In various further aspects, this characteristic allows for additional control through a ring-opening polymerization rather than a rampant polycondensation, which is the usual reaction type used with other $AB_2$ type monomers.[4, 23, 24]

In a further aspect, the added control allows for investigation of branched polyglycidols and the factors that lead to branching. In a still further aspect, implementation of the ring-opening polymerization (ROP) mechanism can yield materials that are more chemically guided rather than empirical in the degree of branching. In an even further aspect, hyperbranched polyglycidol systems can be formed in varying sizes, with low polydispersity indices (PDIs) and controlled degrees of polymerization (DP). In a still further aspect, these polymer systems can be advantageous as alternatives to multistep dendrimer species.[2, 4, 18-20, 22, 25]

In various aspects. the polymer systems formed from these methods have use in numerous applications ranging from potential vaccine models[26] and selective drug delivery vehicles[11-14, 27], to biomineralization control and soluble catalyst supports in organic synthesis. In a further aspect, much of the success seen in these applications relates to the inherent characteristics of the polyglycerol's branched structure. In a still further aspect, limiting the degree of branching (DB), preferably with little change to the PDI, can be beneficial in the formation of new, and possibly more robust, poly(glycidol) architectures.

As briefly described, the current methods for the formation of completely linear poly(glycidol) polymers rely on the use of protected glycidol derivatives polymerized under stringent anionic polymerization conditions. In a further aspect, the polymer then undergoes a deprotection step that removes the protecting group, leaving a linear poly(glycidol) structure. While an effective method for the formation of linear poly(glycidol) species, this method does not address the problems of the system.[28-31]

In some aspects, glycidol based polymers, much like polyethylene glycol (PEG), have severely slow degradation profiles. While not a significant problem for low molecular weight species, the large macromolecular hyperbranched systems cannot be easily eliminated from the body. In a further aspect, the difficult of elimination from the body equates to an inevitable buildup of poly(glycidol) (PG) over time and one would expect eventual data will show higher toxicity with this build up, as is being seen now with PEG. In a still further aspect, the presence of only one post modification unit, the hydroxyl side arms, adds an extra challenge to the creation of a polymer structure that has a variety of post-modification capabilities.

In various further aspects, the present polyglycidol polymer systems can be useful in the solubilization of proteins and siRNA, which investigations had thus far been dominated by polyacrylates having PEG side chains.[32, 33] In most aspects, RAFT initiators are attached to thiol groups on the periphery of the structures, and PEG is grown to cover the outside and increase hydrophilicity.[34] Traditional methods are not ideal because they severely diminish the activity of the protein as well as introduces high molecular weight linear PEG into the body, which cannot easily be eliminated.[35] It is this method of protein solubilization that has been the cause of recent PEG toxicity problems. In some aspects, the attachment of branched PEG systems to thiol-modified siRNA and has shown an increase in biological half-life due to reduced immunogenicity, arising from the morphology of the branched structure, and enhanced resistance against proteolysis.[33]

Figure 3:
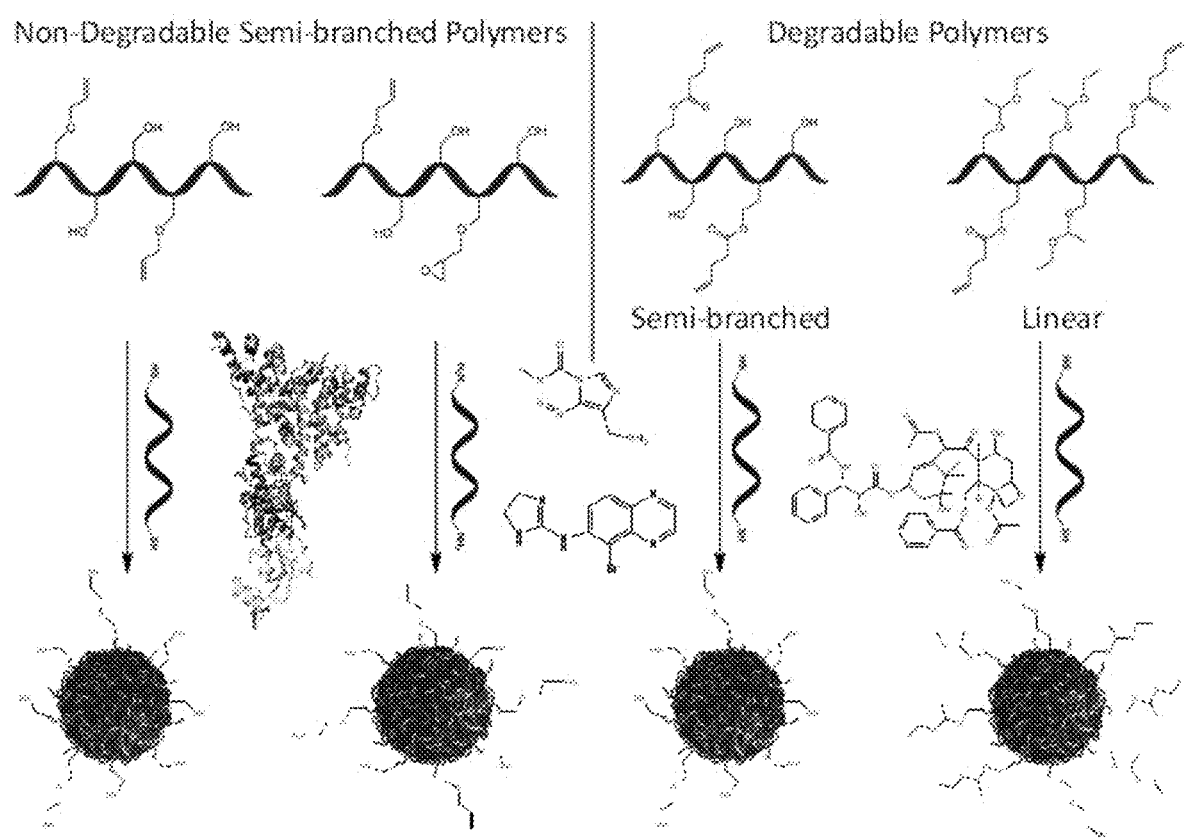
FIG. 3 shows a schematic representation of degradability of glycidol polymers.
Figure 4:
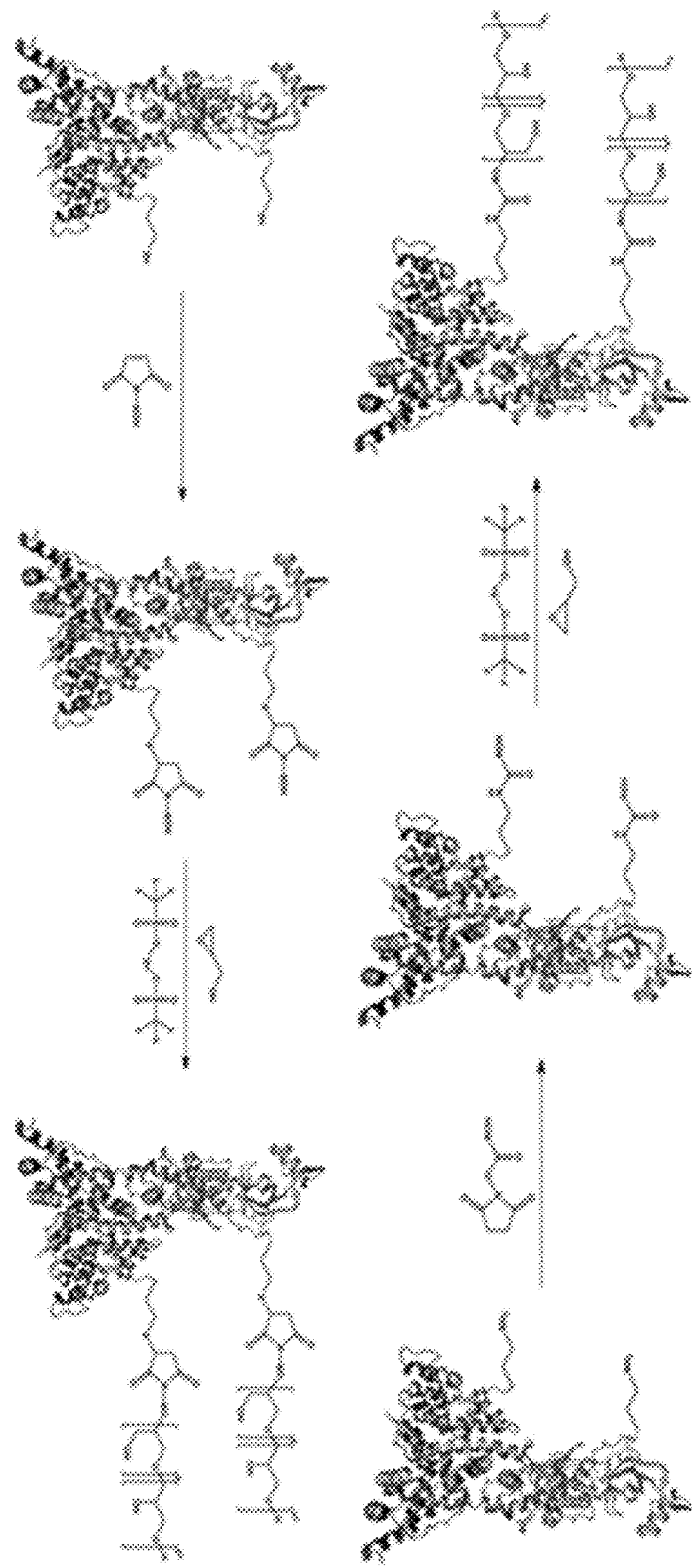
FIG. 4 shows schematic representations of glycidol polymers carrying solubilized biological cargo.
Figure 5:
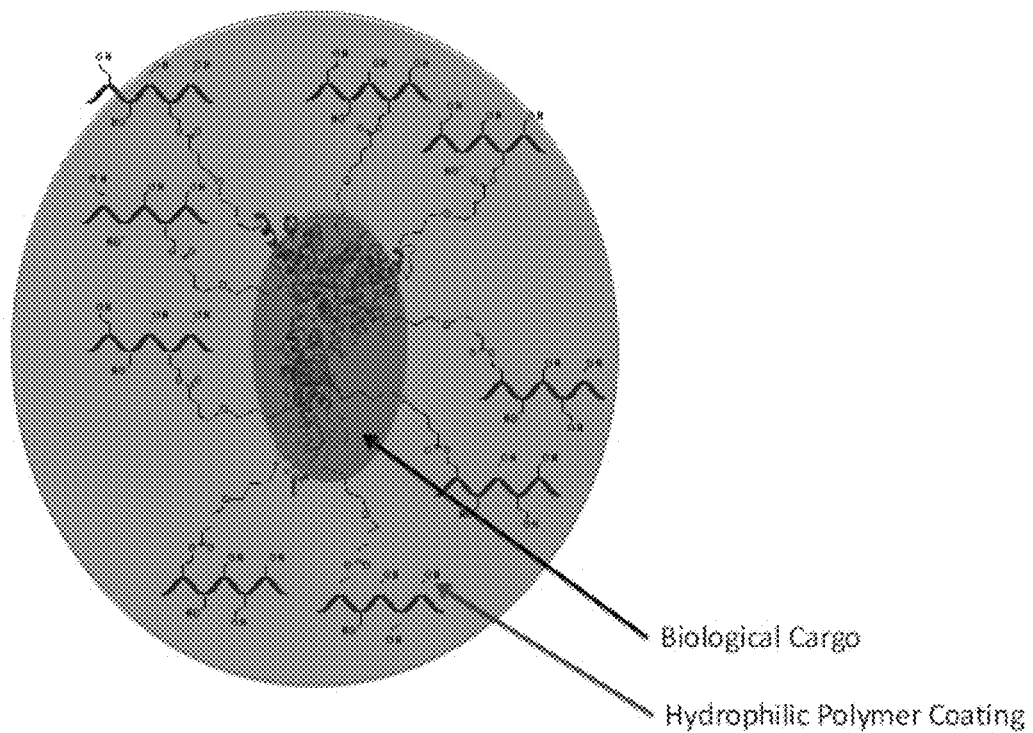
FIG. 5 shows a schematic representation of a polyethylene glycol)-protein conjugate.

In further aspects, poly(glycidol) can be used as a method of increasing the solubility of biological structures, as depicted in FIG. 3. In a still further aspect, the ability to control the degree of branching present will be integral to the efficacy of the synthesized structures and will allow for a more tailored approach to solubilization of biological structures and their behavior in vivo, as shown in FIGS. 4 and 5. In a yet further aspect, facilitated by the increased degradability, the glycidol based copolymers can be both more effective and less harmful than their PEG counterparts.

Although a seemingly glaring problem, the low degree of solubility in the polyglycerol systems has, for the most part, been overlooked. Rather than attempting to form polyglycerols with increased capabilities, a large amount of research has been aimed at increasing the hydrophilicity of polyester structures. Using polyether macroinitiators in the attempt to form block copolymers is one method of combating this downfall of the polyester systems. Unfortunately, the polymers synthesized in this manner are highly prone to the formation of micellular structures, thus drastically diminishing their actual viability.[1] Few studies have been attempted on the basis of random copolymerization of glycidol with other monomer species, and rarely address the branching characteristics of the synthesized polymers.[24, 36] These copolymerizations have also been dictated by the use of a single catalyst, stannous ethylhexanoate, which is a common lactide polymerization catalyst that implements a coordination-insertion type mechanism.

The compounds and compositions described herein combat the problems associated with polyglycerols, while still maintaining a high degree of water solubility and low PDI values. In a further aspect, the present disclosure provides inclusion of increased physiological degradability, through the incorporation of esters, as well as the introduction of more viable post modification units, by the addition of allyl groups. In a further aspect, the implementation of stannous triflate has been chosen as the desired catalysis method based on its ability to allow for low reaction temperatures while maintaining high polymerization rates and low PDI values.

In a still further aspect, by employing the stannous triflate catalyst at low temperatures, the DB of the resulting polymers can be restricted to well below the currently published values of 40% and higher. In still further aspect, the present invention can comprise a range of comonomers, both commercially available and novel, which exhibit the ability to copolymerize with glycidol to form an array of new and exciting polymer architectures. In a yet further aspect, the polymers comprise desirable structural features and can provide new polymers with customizable degrees of branching, high functionality, increased solubility, and tunable biodegradability, thus imbuing all the benefits of polyglycerols to systems that are more tailored for delivery of a range of drugs and biological cargo. In an even further aspect, the chemical characteristics of the synthesized polymers were investigated through both $^1$HNMR and $^{13}$CNMR techniques, and are further described in the Examples.

Disclosed herein is a polymer comprising repeating units selected from:

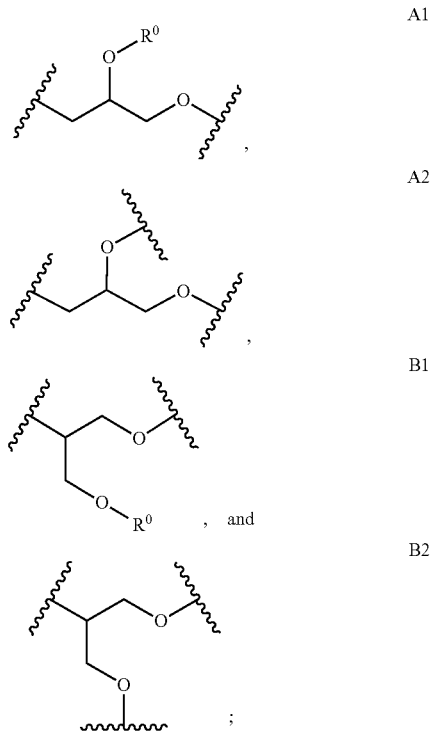

wherein R⁰ is selected from H, alkyl, NH$_2$, and R$^1$; wherein R$^1$ comprises a crosslinking functionality; wherein repeating units A1, A2, B1, and B2 account for at least about 50 wgt % of the polymer; and wherein the ratio of (A1+A2):(B1+B2) is greater than 1.

In one aspect, the ratio of (A1+A2):(B1+B2) is greater than 1. In another aspect, the ratio of (A1+A2):(B1+B2) is greater than 3. In yet another aspect, the ratio of (A1+A2):(B1+B2) is greater than 5. In yet another aspect, the ratio of (A1+A2):(B1+B2) is greater than 10. In yet another aspect, the ratio of (A1+A2):(B1+B2) is greater than 25. In yet another aspect, the ratio of (A1+A2):(B1+B2) is greater than 50. In yet another aspect, the ratio of (A1+A2):(B1+B2) is greater than 100. In yet another aspect, the ratio of (A1+A2):(B1+B2) is from 1 to 100. In yet another aspect, the ratio of (A1+A2):(B1+B2) is from 5 to 100. In yet another aspect, the ratio of (A1+A2):(B1+B2) is from 10 to 100. In yet another aspect, the ratio of (A1+A2):(B1+B2) is from 25 to 100.

In one aspect, repeating units A1; A2; B1; and B2 account for at least about 50 wgt % of the polymer. In another aspect, repeating units A1; A2; B1; and B2 account for at least about 60 wgt % of the polymer. In yet another aspect, repeating units A1; A2; B1; and B2 account for at least about 60 wgt % of the polymer. In yet another aspect, repeating units A1; A2; B1; and B2 account for at least about 70 wgt % of the polymer. In yet another aspect, repeating units A1; A2; B1; and B2 account for at least about 80 wgt % of the polymer. In yet another aspect, repeating units A1; A2; B1; and B2 account for at least about 90 wgt % of the polymer. In yet another aspect, repeating units A1; A2; B1; and B2 account for at least about 95 wgt % of the polymer. In yet another aspect, repeating units A1; A2; B1; and B2 account for at least about 99 wgt % of the polymer.

In one aspect, the polymer is covalently bonded to a biologic agent, such as a protein, DNA, or SiRNA, for example, a protein. Such system can enhance the solubility of the biologic agent.

In one aspect, the polymer comprising at least one repeating unit formed from a monomer selected from:

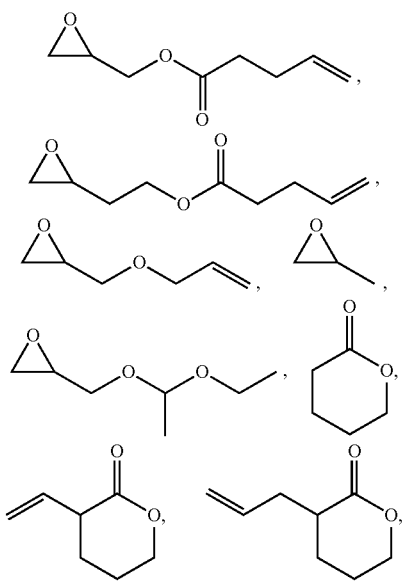

-continued

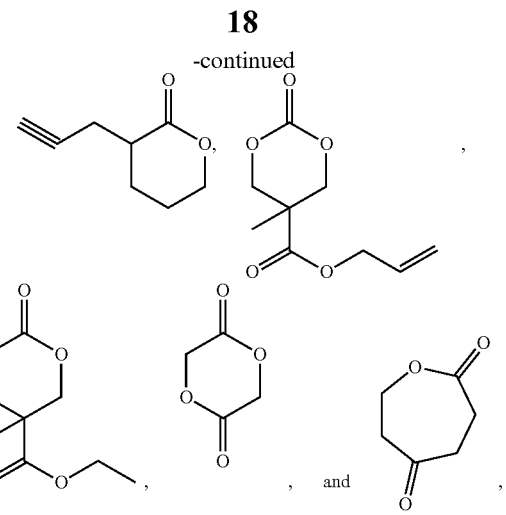

or a combination thereof.

In one aspect, the polymer comprises at least one repeating unit from a monomer selected from:

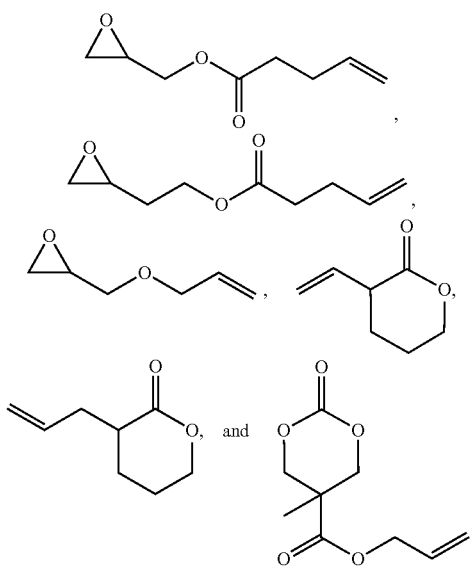

or a combination thereof, and wherein the polymer is oxidized to form repeating units comprising epoxides or alkynes.

It is understood that all or only a portion of the repeating units are oxidized in the polymer. Thus, it is understood that the resultant polymer can comprise repeating units comprising alkenes and repeating units comprising epoxides and/or alkynes. For example, the polymer can comprise at least 1%, 5%, 10%, 15%, 20%, or 25% repeating units that have been oxidized. Thus, in one aspect, the polymer comprises repeating units comprising pendent groups selected from

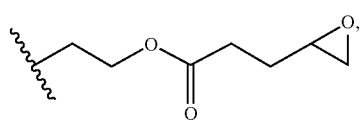

-continued

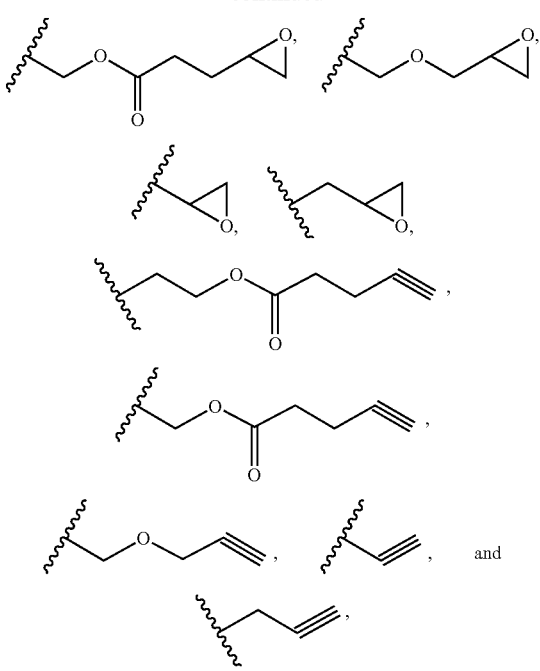

or a combination thereof.

In one aspect, the polymer further comprises a repeating unit formed from

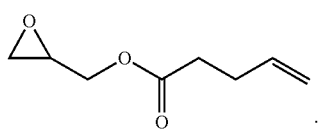

In another aspect, the polymer further comprises a repeating unit formed from

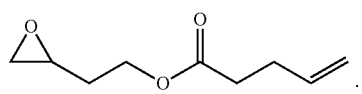

In yet another aspect, the polymer further comprises a repeating unit formed from

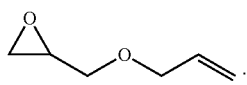

In yet another aspect, the polymer further comprises a repeating unit formed from

In yet another aspect, the polymer further comprises a repeating unit formed from

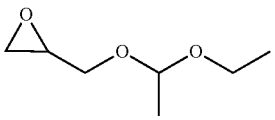

In yet another aspect, the polymer further comprises a repeating unit formed from

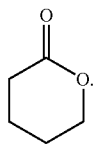

In yet another aspect, the polymer further comprises a repeating unit formed from

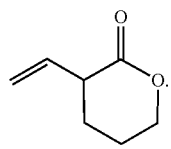

In yet another aspect, the polymer further comprises a repeating unit formed from

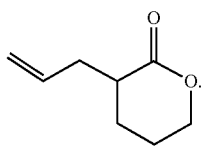

In yet another aspect, the polymer further comprises a repeating unit formed from

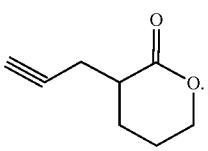

In yet another aspect, the polymer further comprises a repeating unit formed from

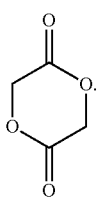

In yet another aspect, the polymer further comprises a repeating unit formed from

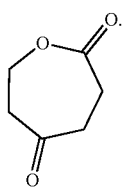

In yet another aspect, the polymer further comprises a repeating unit formed from

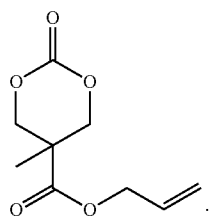

In yet another aspect, the polymer further comprises a repeating unit formed from

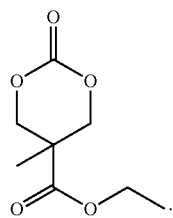

In one aspect, the polymer further comprises crosslinks, wherein the crosslinks comprise

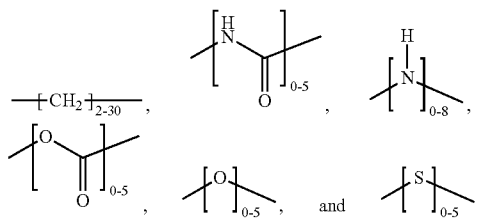

wherein at least one of

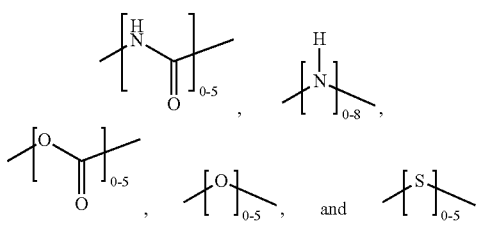

is not 0.

The crosslinks binds two or more polymers together. The polymers can be any polymer disclosed herein. The crosslinks can comprise one or more, such as two, moieties that can react with one or more of the disclosed polymers thereby linking the polymers together. Thus, suitable moieties include those that can react with alkenes, epoxides, or alkynes. Non-limiting moieties include —SH, —NH$_2$, and

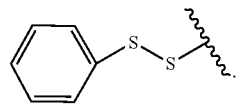 [SMILES: *SSc1ccccc1]

The resultant polymer will then comprise one or more bonds which is a result from these reactions. For example, the polymer can comprise —S— and —NH— bonds. It is also understood that these reactions will reduce the alkenes, alkynes, or epoxides that participates in the reactions.

In one aspect, the polymer comprises

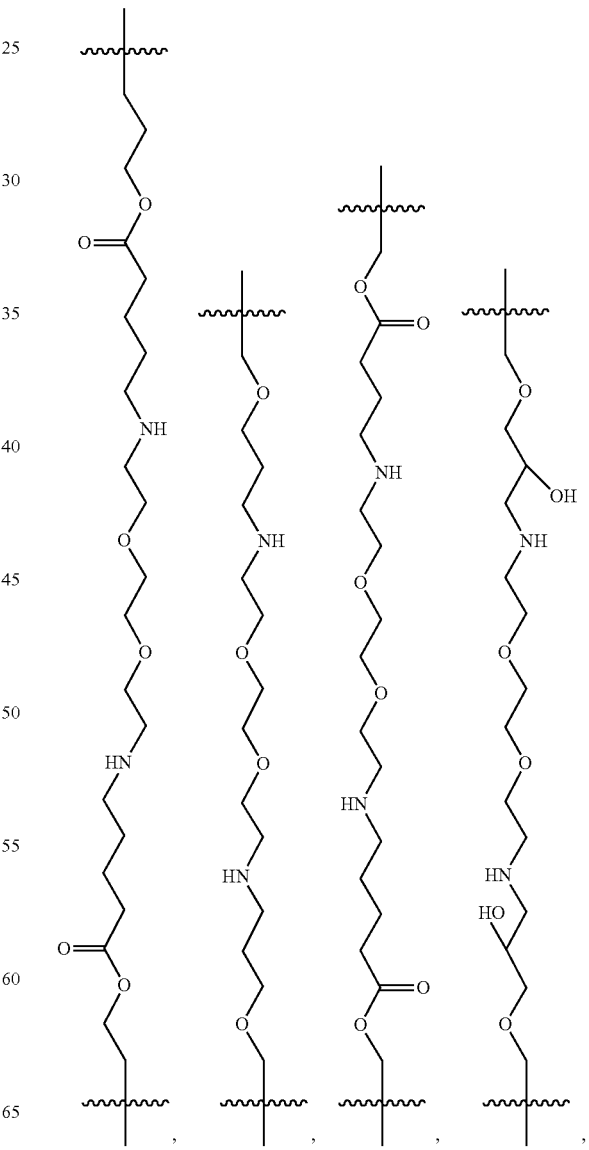

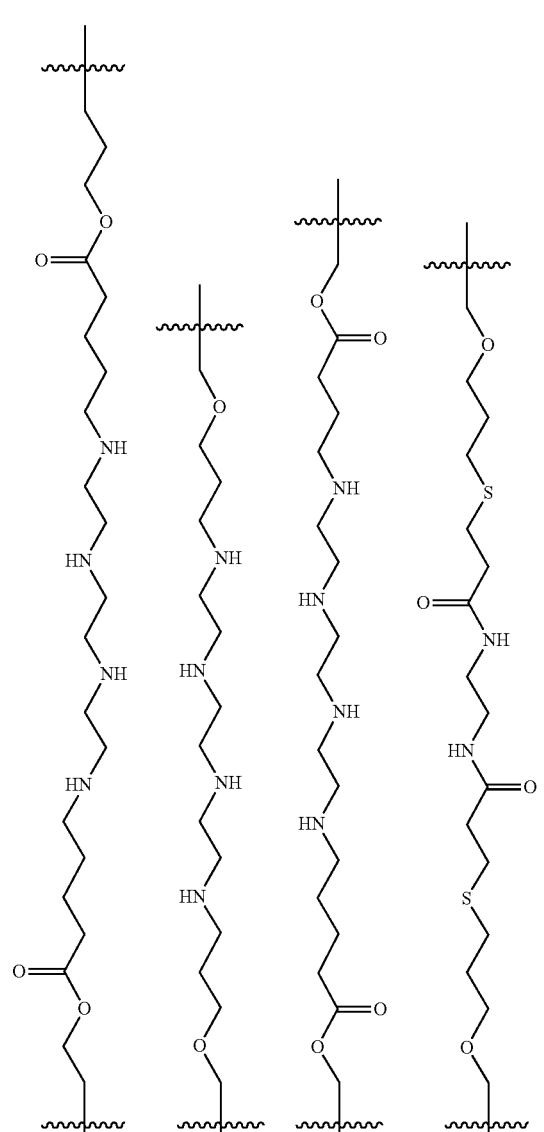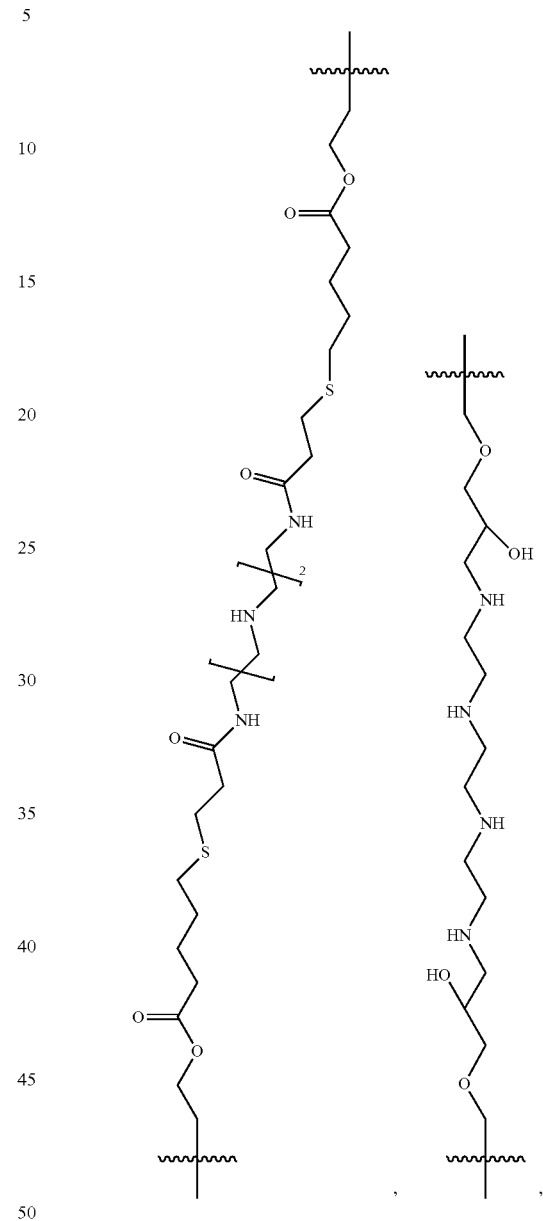

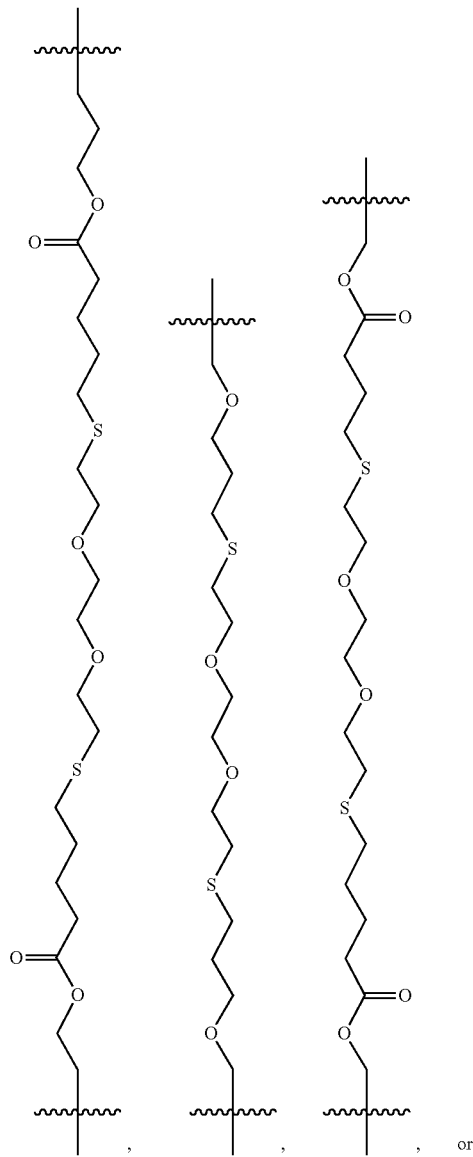 [SMILES: *CCCOC(=O)CCCCSCCOCCOCCSCCCCC(=O)OCC* ; *COCCCSCCOCCOCCSCCCOC* ; *COC(=O)CCCCSCCOCCOCCSCCCC(=O)OC*], or
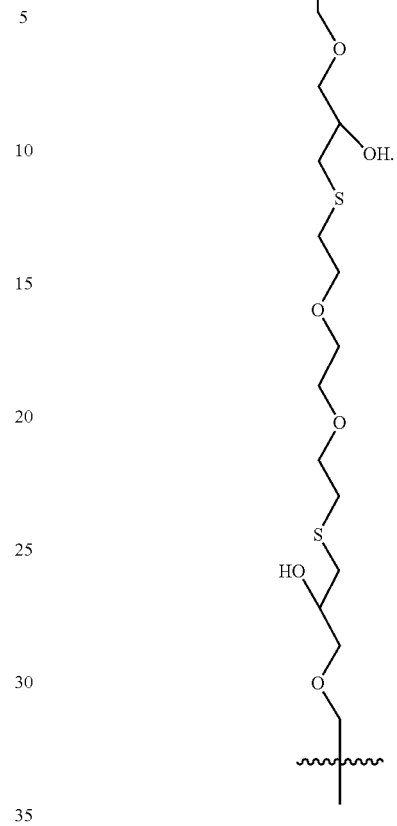
Accordingly, the polymer can comprise the structure
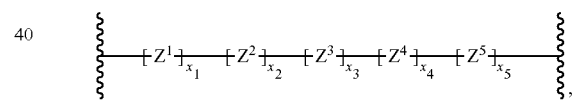
wherein $Z^1$ is
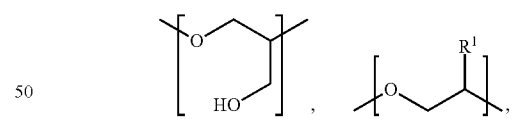
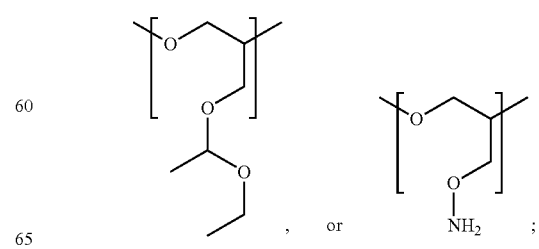

wherein $Z^2$ is

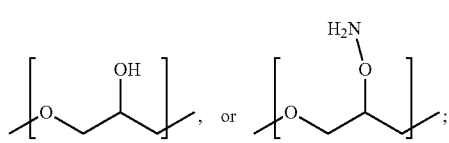

, or wherein $Z^3$ is

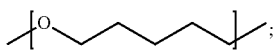

;

wherein $Z^4$ is

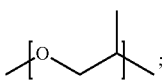

;

wherein $Z^5$ is

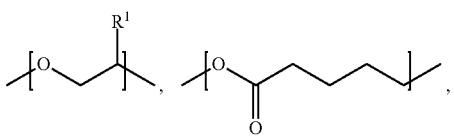

,

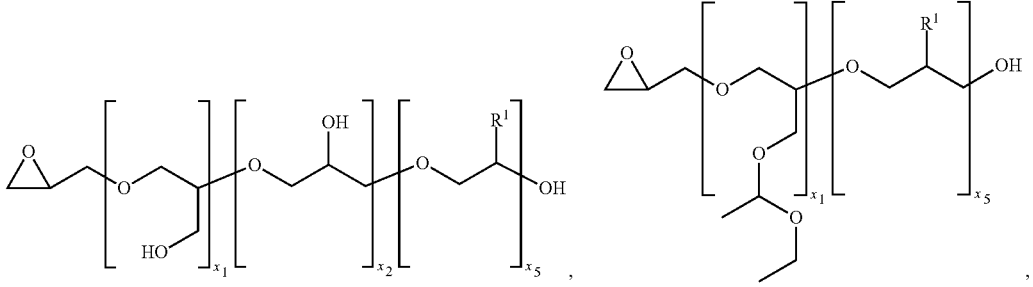

or a combination thereof;

wherein, simultaneously, $X_1$ is from greater than 0% to 90%, $X_2$ is from 0% to 95%, $X_3$ is from 0% to 90%, $X_4$ is from 0% to 90%, and $X_5$ is from greater than 0% to 90%, provided that $X_1+X_2+X_3+X_4+X_5$ equals 100%; and wherein each $R^1$ independently comprises a crosslinking functionality In one aspect, the crosslinking functionality comprises an allyl, epoxide, amine, thiol, azide, or alkyne functionality. In one aspect, the crosslinking functionality comprises an allyl functionality. In another aspect, the crosslinking functionality comprises an epoxide. In yet another aspect, the crosslinking functionality comprises an amine functionality. In yet another aspect, the crosslinking functionality comprises a thiol functionality. In yet another aspect, the crosslinking functionality comprises an azide functionality. In yet another aspect, the crosslinking functionality comprises an alkyne functionality.

In one aspect, polymer has the structure selected from the group consisting of

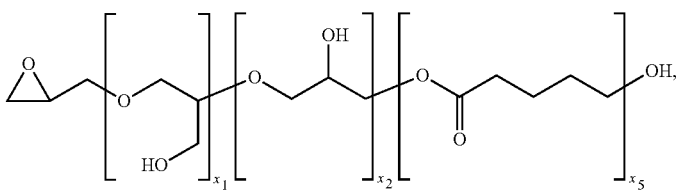

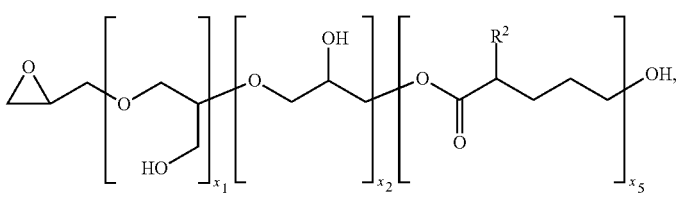

-continued
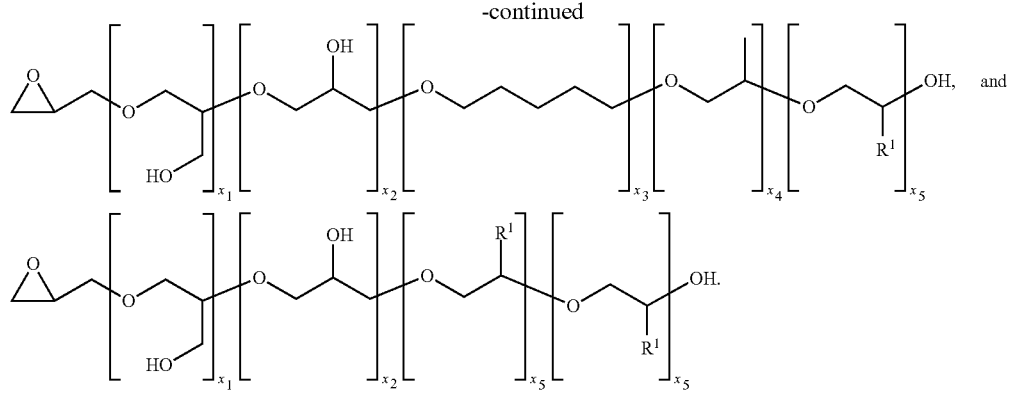
In one aspect, the polymer can comprise one or more of repeating units selected from
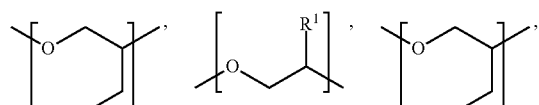,
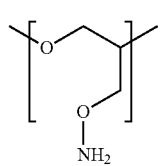,
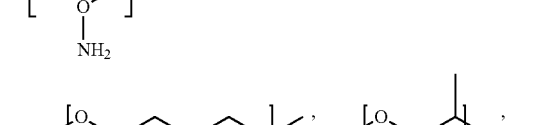,
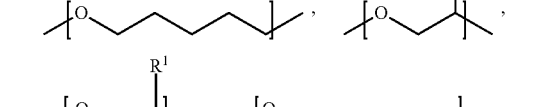,
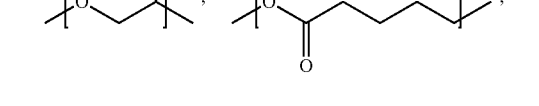,
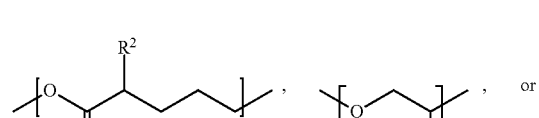, or
,
or a combination thereof.
In another aspect, the polymer can comprise the structure
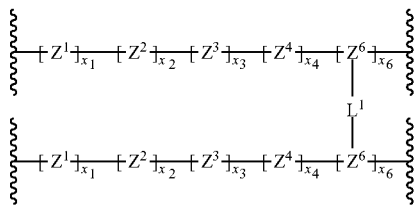
wherein each $Z^1$ independently is
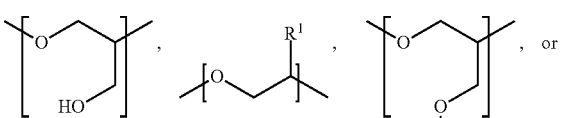
;
wherein each $Z^2$ independently is
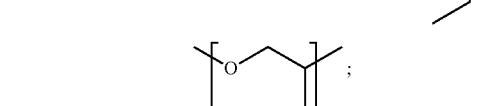, or 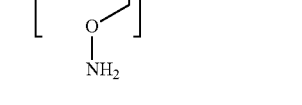;
wherein $Z^3$ is
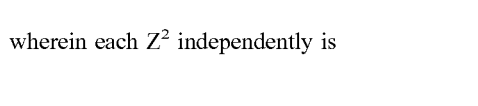;

wherein $Z^4$ is

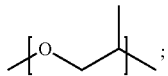

wherein each $Z^6$ independently comprises

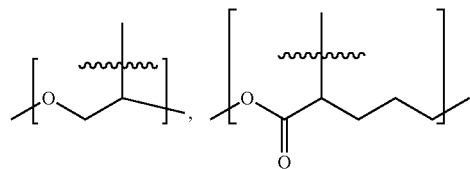

and optionally independently comprises

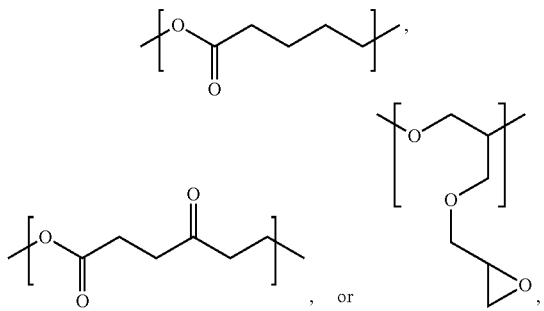

or a combination thereof; wherein, simultaneously, $X_1$ is from greater than 0% to 90%, $X_2$ is from 0% to 95%, $X_3$ is from 0% to 90%, $X_4$ is from 0% to 90%, and $X_6$ is from greater than 0% to 90%, provided that $X_1+X_2+X_3+X_4+X_6$ equals 100%; wherein each $R^1$ independently comprises a crosslinking functionality; and wherein $L^1$ comprises

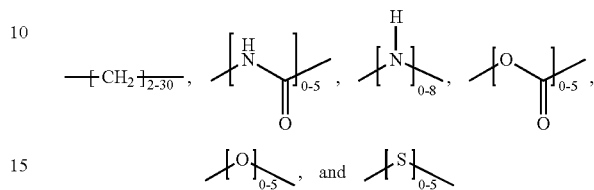

wherein least one of

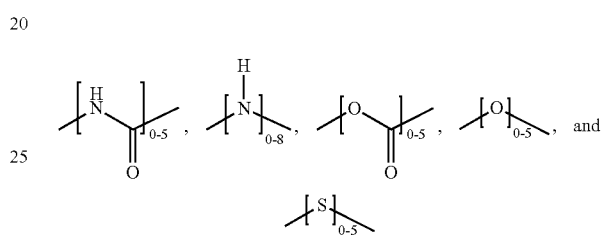

is not 0.

In one aspect, the compound comprises the structure

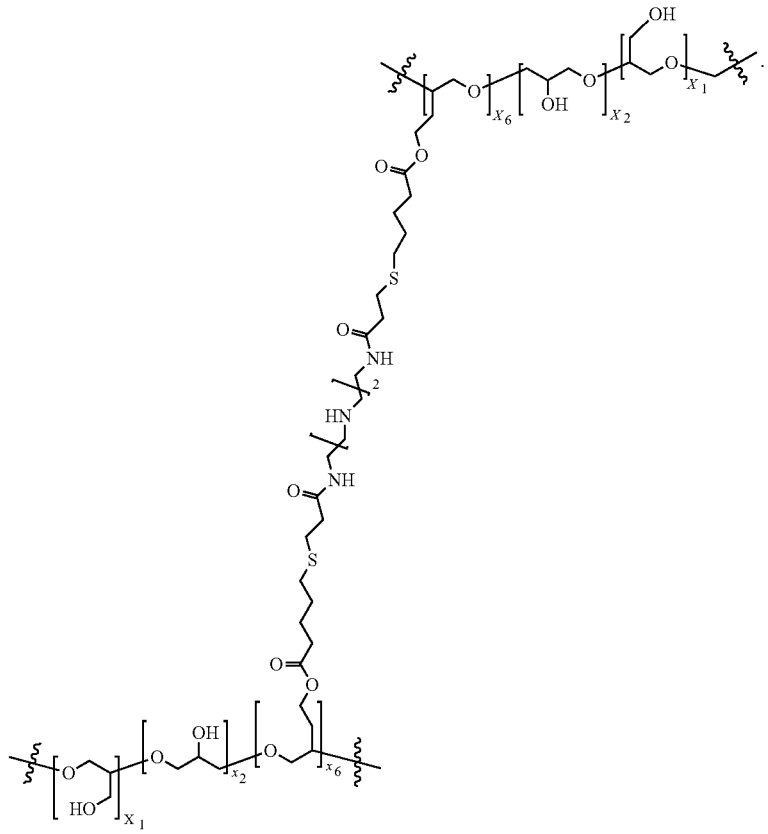

In one aspect, the polymer comprises a structure formed from reacting a polymer disclosed herein further comprising repeating units

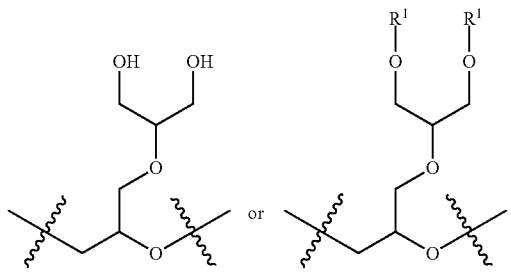

with a polymer comprising at least one repeating unit formed from

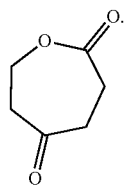

In one aspect, such polymer further comprises a structure formed from reacting the polymer with a polymer comprising at least one repeating unit formed from

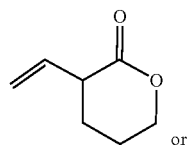

or

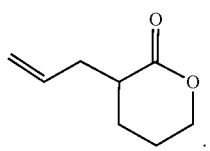

Also disclosed herein is a composition comprising a. a polymer comprising repeating units formed from monomers

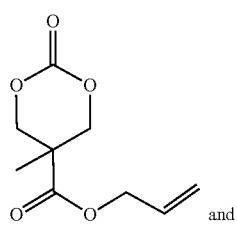
and

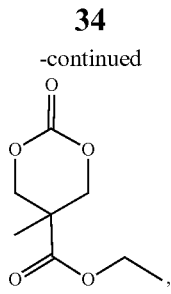

wherein the polymer is crosslinked via crosslinks, wherein the crosslinks comprises

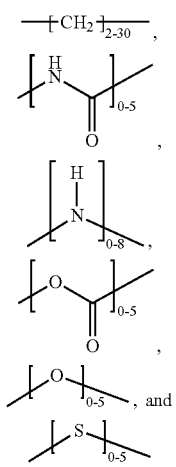

wherein at least one of

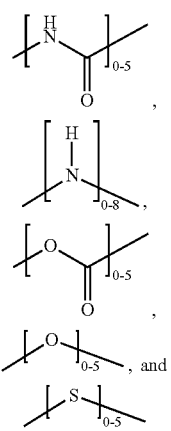

is not 0; and b. a polymer comprising repeating units selected from:

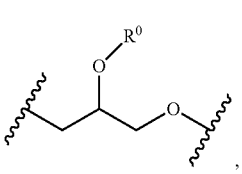

A1

A2
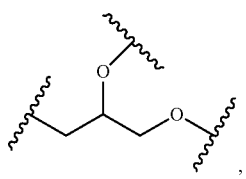,
B1
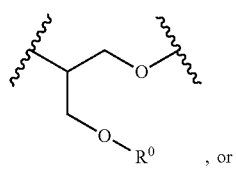, or
B2
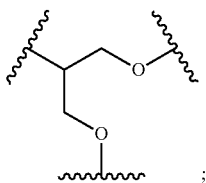;
wherein $R^0$ is selected from H, alkyl, $NH_2$, or $R^1$; wherein $R^1$ comprises a crosslinking functionality; wherein repeating units A1; A2; B1; and B2 account for at least about 50 wgt % of the polymer; and wherein the ratio of (A1+A2):(B1+B2) is greater than 1, wherein the polymers are optionally covalently bonded together.
Thus, the polymer can comprise the structure
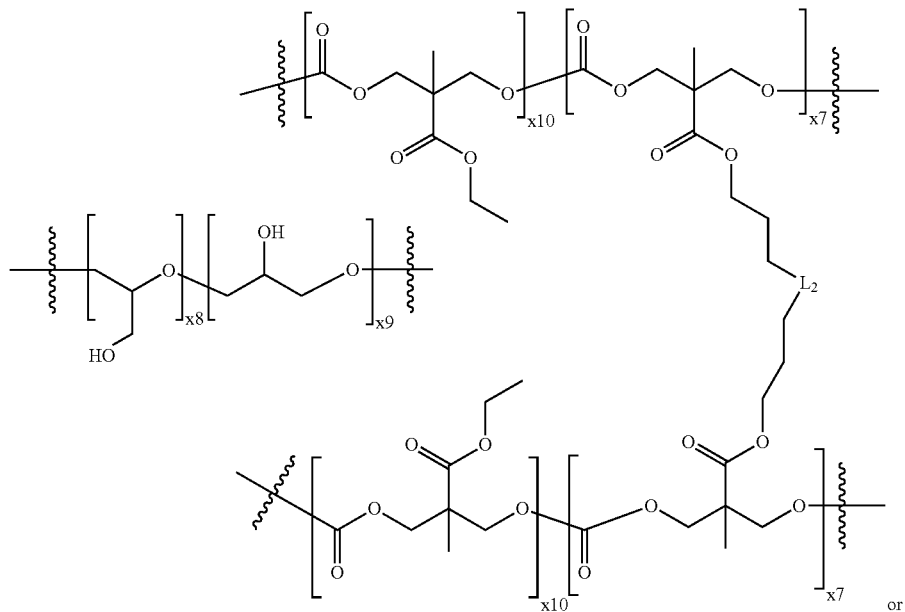

-continued

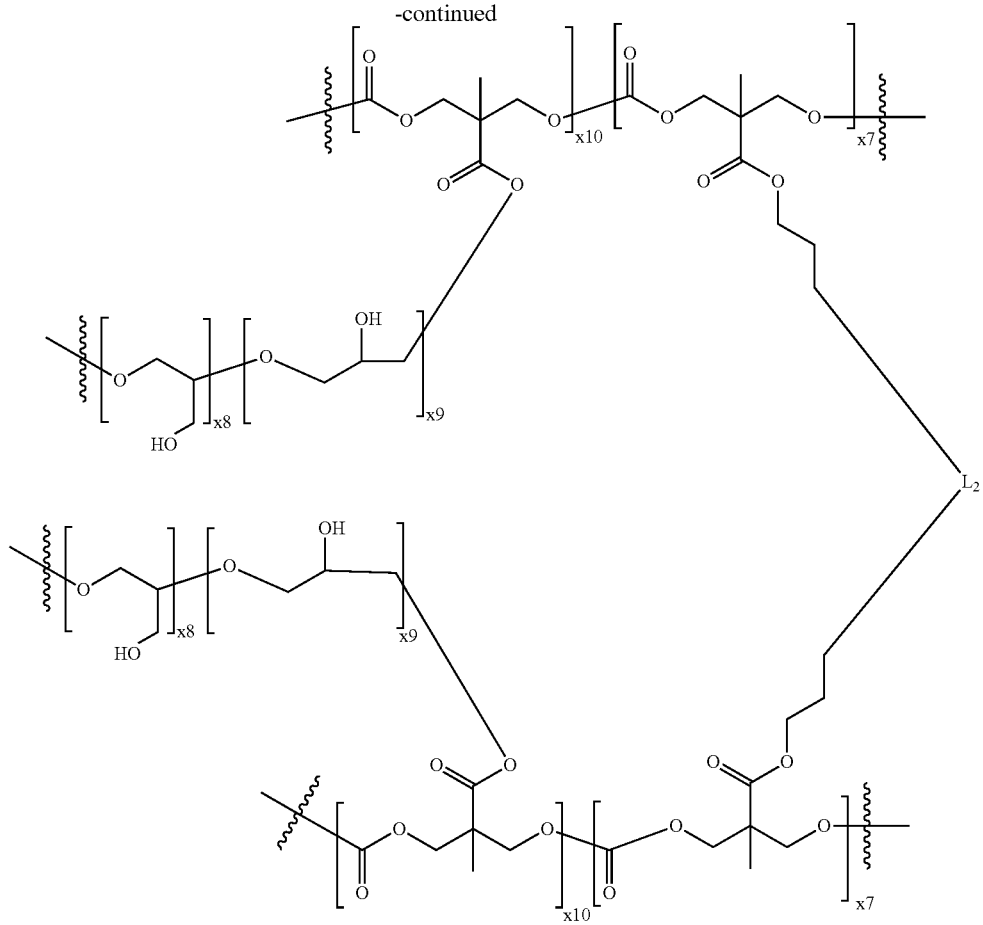

wherein L² comprises

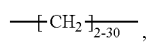,

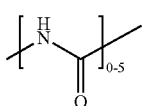,

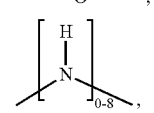,

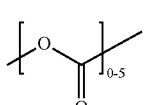,

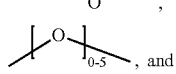, and

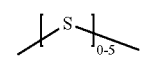

wherein at least one of

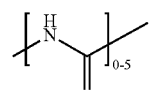,

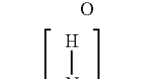,

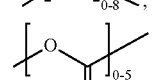,

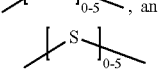, and

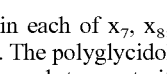

is not 0; and wherein each of $x_7$, $x_8$, $x_9$, and $x_{10}$ independently are 1 to 1000. The polyglycidol is reversibly attached and disconnected through transesterification reactions. The attachment of the polyglycidol to the polycarbonate via a transesterification reaction can be promoted by the use of zinc acetate and heat. Such reaction is reversible. The attachment and disconnection of the polyglycidol can be a function of the temperature, thus, the structure of the compound can be controlled by altering the temperature. Such compound is called a macroscopic network and can be thermally responsive. Thus, the properties of the compound can be altered by attaching or disconnecting the polyglycidol to the polycarbonate polymer. A therapeutic agent, diagnostic agent, or prophylactic agent, or a mixture thereof, can be present in a composition comprising the compound or macroscopic network. These macroscopic networks can be altered via reversible trans-esterification reactions, thereby changing the properties of the macroscopic network. An example of such technology is described by Montarnal et al. (Science, 334, 965 (2011), which is hereby incorporated by references in its entirety.

In one aspect, the polymer is a macroscopic network.

In one aspect, the polymer is biodegradable.

In one aspect, the polymer has a weight average molecular weight from 1 kDa to 1,000 kDa. In another aspect, the polymer has a weight average molecular weight from 1 kDa to 500 kDa. In yet another aspect, the polymer has a weight average molecular weight from 1 kDa to 150 kDa. In yet another aspect, the polymer has a weight average molecular weight from 1 kDa to 100 kDa. In yet another aspect, the polymer has a weight average molecular weight from 1 kDa to 75 kDa. In yet another aspect, the polymer has a weight average molecular weight from 1 kDa to 50 kDa. In yet another aspect, the polymer has a weight average molecular weight from 1 kDa to 25 kDa. In yet another aspect, the polymer has a weight average molecular weight from 1 kDa to 10 kDa.

In one aspect, the polymer has a PDI from 1.01 to 5.0. In another aspect, the polymer has a PDI from 1.01 to 4.0. In yet another aspect, the polymer has a PDI from 1.01 to 3.0. In yet another aspect, the polymer has a PDI from 1.01 to 2.0. In yet another aspect, the polymer has a PDI from 1.01 to 1.5. In yet another aspect, the polymer has a PDI from 1.01 to 1.25. In yet another aspect, the polymer has a PDI from 1.01 to 1.10.

a. X Groups

In one aspect, $X_1+X_2$ equals from 50% to 99%. In another aspect, $X_1+X_2$ equals from 60% to 95%. In yet another aspect, $X_1+X_2$ equals from 70% to 90%.

In one aspect, $X_1+X_2+X_3+X_4$ equals from 50% to 99%. In another aspect, $X_1+X_2+X_3+X_4$ equals from 60% to 95%. In yet another aspect $X_1+X_2+X_3+X_4$ equals from 70% to 90%.

In one aspect, $X_5$ is from 1% to 40%. In another aspect, $X_5$ is from 5% to 35%. In yet another aspect, $X_5$ is from 10% to 30%.

In one aspect, $X_2$, $X_3$, and $X_4$ are 0%. In another aspect, $X_2$ is greater than 0% to 90% and $X_3$, and $X_4$ are 0%. In yet another aspect, $X_2$, $X_3$, and $X_4$ are from greater than 0% to 90%.

In one aspect, each of $X_1$, $X_2$, $X_3$, $X_4$, and $X_5$ independently are 1 to 1000. In one aspect, each of $X_1$, $X_2$, and $X_5$ independently are 1 to 1000. In one aspect, each of $X_1$ and $X_5$ independently are 1 to 1000. In another aspect, each of $X_1$, $X_2$, $X_3$, $X_4$, and $X_5$ independently are 1 to 500. In yet another aspect, each of $X_1$, $X_2$, $X_3$, $X_4$, and $X_5$ independently are 1 to 300. In yet another aspect, each of $X_1$, $X_2$, $X_3$, $X_4$, and $X_5$ independently are 1 to 100. In yet another aspect, each of $X_1$, $X_2$, $X_3$, $X_4$, and $X_5$ independently are 1 to 50. In yet another aspect, each of $X_1$, $X_2$, $X_3$, $X_4$, and $X_5$ independently are 1 to 25. In another aspect, each of $X_1$, $X_2$, and $X_5$ independently are 1 to 500. In yet another aspect, each of $X_1$, $X_2$, and $X_5$ independently are 1 to 300. In yet another aspect, each of $X_1$, $X_2$, and $X_5$ independently are 1 to 100. In yet another aspect, each of $X_1$, $X_2$, and $X_5$ independently are 1 to 50. In yet another aspect, each of $X_1$, $X_2$, and $X_5$ independently are 1 to 25. In another aspect, each of $X_1$ and $X_5$ independently are 1 to 500. In yet another aspect, each of $X_1$ and $X_5$ independently are 1 to 300. In yet another aspect, each of $X_1$ and $X_5$ independently are 1 to 100. In yet another aspect, each of $X_1$ and $X_5$ independently are 1 to 50. In yet another aspect, each of $X_1$ and $X_5$ independently are 1 to 25.

In one aspect, each of $X_1$, $X_2$, $X_3$, $X_4$, and $X_6$ independently are 1 to 1000. In one aspect, each of $X_1$, $X_2$, and $X_6$ independently are 1 to 1000. In one aspect, each of $X_1$ and $X_6$ independently are 1 to 1000. In another aspect, each of $X_1$, $X_2$, $X_3$, $X_4$, and $X_6$ independently are 1 to 500. In yet another aspect, each of $X_1$, $X_2$, $X_3$, $X_4$, and $X_6$ independently are 1 to 300. In yet another aspect, each of $X_1$, $X_2$, $X_3$, $X_4$, and $X_6$ independently are 1 to 100. In yet another aspect, each of $X_1$, $X_2$, $X_3$, $X_4$, and $X_6$ independently are 1 to 50. In yet another aspect, each of $X_1$, $X_2$, $X_3$, $X_4$, and $X_6$ independently are 1 to 25. In another aspect, each of $X_1$, $X_2$, and $X_6$ independently are 1 to 500. In yet another aspect, each of $X_1$, $X_2$, and $X_6$ independently are 1 to 300. In yet another aspect, each of $X_1$, $X_2$, and $X_6$ independently are 1 to 100. In yet another aspect, each of $X_1$, $X_2$, and $X_6$ independently are 1 to 50. In yet another aspect, each of $X_1$, $X_2$, and $X_6$ independently are 1 to 25. In another aspect, each of $X_1$ and $X_6$ independently are 1 to 500. In yet another aspect, each of $X_1$ and $X_6$ independently are 1 to 300. In yet another aspect, each of $X_1$ and $X_6$ independently are 1 to 100. In yet another aspect, each of $X_1$ and $X_6$ independently are 1 to 50. In yet another aspect, each of $X_1$ and $X_6$ independently are 1 to 25.

In one aspect, each of $x_7$, $x_8$, $x_9$, and $x_{10}$ independently are 1 to 1000. In another aspect, each of $x_7$, $x_8$, $x_9$, and $x_{10}$ independently are 1 to 500. In yet another aspect, each of $x_7$, $x_8$, $x_9$, and $x_{10}$ independently are 1 to 300. In yet another aspect, each of $x_7$, $x_8$, $x_9$, and $x_{10}$ independently are 1 to 100. In yet another aspect, each of $x_7$, $x_8$, $x_9$, and $x_{10}$ independently are 1 to 50. In yet another aspect, each of $x_7$, $x_8$, $x_9$, and $x_{10}$ independently are 1 to 25.

b. Z Groups

It is understood that the Z groups represent It is understood that the arrangement of Z groups in the polymers disclosed herein can be in any order, for example, $Z^1$, $Z^2$, $Z^3$, $Z^4$, and $Z^5$ can be in any order. Thus, it is also understood that the polymer can be a random copolymer, whereby the order of each repeat unit of $Z^1$, $Z^2$, $Z^3$, $Z^4$, and $Z^5$ is random.

In one aspect, $Z^1$ is

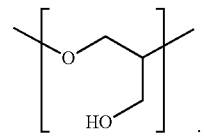

In another aspect, $Z^1$ is

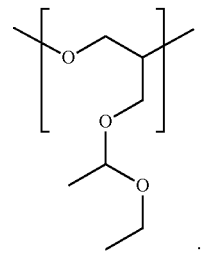

In yet another aspect, $Z^1$ is

![structure: -[O-CH2-CH(CH2-O-NH2)]-]

In yet another aspect, $Z^1$ is

![structure: -[O-CH2-CH(R^1)]-]

In one aspect, $Z^2$ is

![structure: -[O-CH2-CH(OH)]-]

In another aspect, $Z^2$ is

![structure: -[O-CH2-CH(O-NH2)]-]

In one aspect, $Z^5$ is

![structure: -[O-CH2-CH(R^1)]-]

In another aspect, $Z^5$ is

![structure: -[O-C(=O)-CH2CH2CH2]-]

In yet another aspect, $Z^5$ is

![structure: -[O-C(=O)-CH(R2)-CH2CH2]-]

In yet another aspect, $Z^5$ is

![structure: -[O-C(=O)-CH2CH2-C(=O)-CH2]-]

In yet another aspect, $Z^5$ is

![structure: -[O-CH2-CH(CH2-O-CH2-epoxide)]-O]

In yet another aspect, $Z^5$ is

![structure: -[O-C(=O)-CH(R2)-CH2CH2]-]

and

![structure: -[O-CH2-CH(CH2-O-CH2-epoxide)]-O]

In yet another aspect, $Z^5$ is

![structure: -[O-CH2-CH(R^1)]- and -[O-CH2-CH(CH2-O-CH2-epoxide)]-O]

In one aspect, each $Z^6$ comprise

![structure: -[O-CH2-CH]- with squiggly bond]

In another aspect, each $Z^6$ comprises

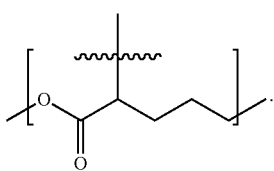

In one aspect, $Z^{11}$ is

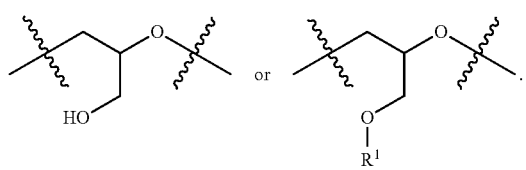

In one aspect, $Z^{12}$ is

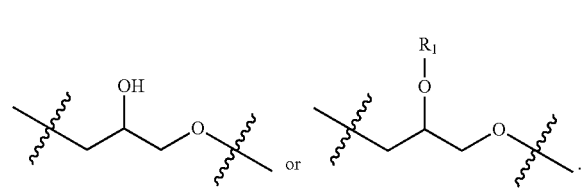

In one aspect, $Z^{13}$ is

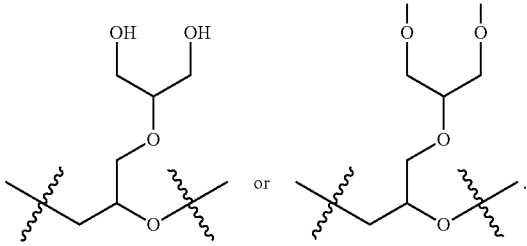

c. R Groups

In one aspect, $R^0$ is H. In another aspect, $R^0$ is alkyl. In yet another aspect, $R^0$ is $NH_2$. In yet another aspect, $R^0$ is $R^1$.

In one aspect, each of R and $R^2$ independently comprises

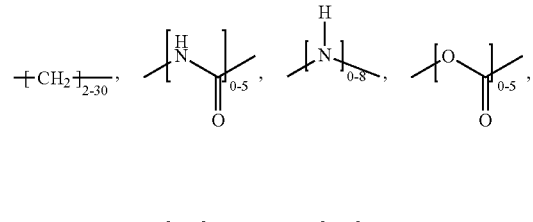

wherein at least one of

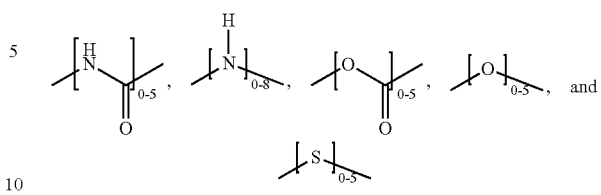

is not 0.

In one aspect, $R^1$ comprises

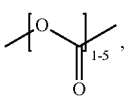

for example, $R^1$ can comprise

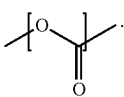

In one aspect, $R^1$ comprises

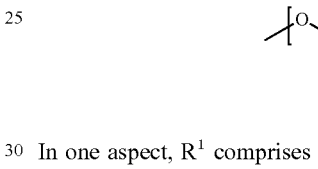

In another aspect, $R^1$ comprises

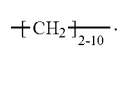

In one aspect, $R^1$ comprises

In yet another aspect, $R^1$ comprises

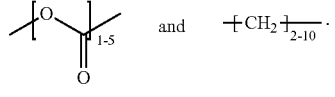

In yet another aspect, $R^1$ comprises

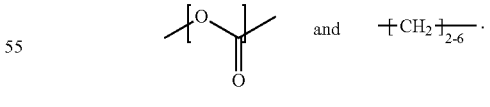

and an allyl functionality.

In one aspect, R² comprises
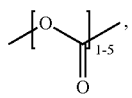
for example, R² can comprise
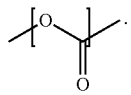
In one aspect, R² comprises
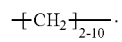
In another aspect, R² comprises
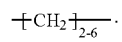
In one aspect, R² comprises
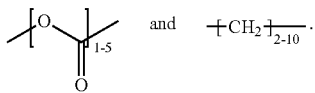
In yet another aspect, R² comprises
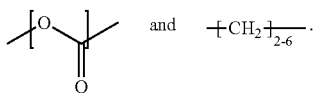
In yet another aspect, R¹ comprises
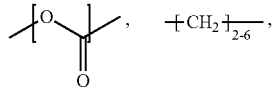
and an allyl functionality.
In one aspect, the each of R¹ and R² independently are selected from the group consisting of
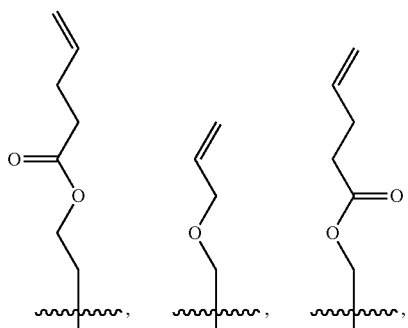
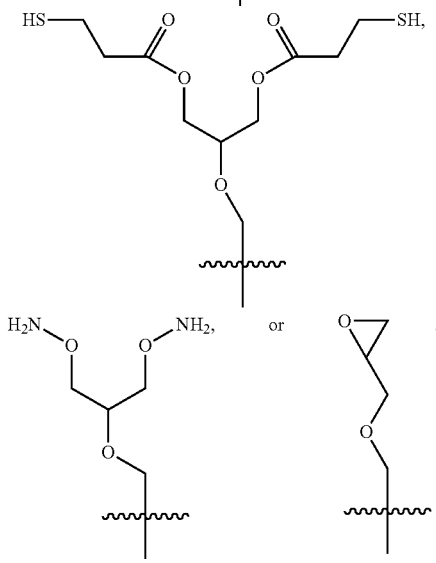
In one aspect, R¹ is
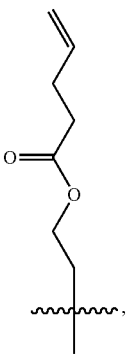

In another aspect, R¹ is
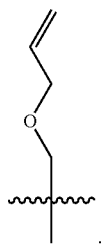
In yet another aspect, R¹ is
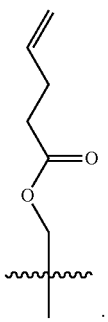
In yet another aspect, R¹ is
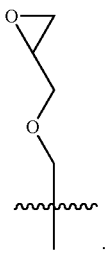
In yet another aspect, R¹ is
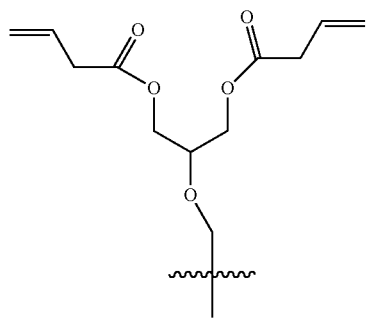
In yet another aspect, R¹ is
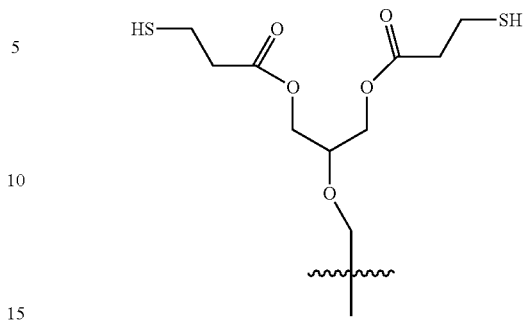
In yet another aspect, R¹ is
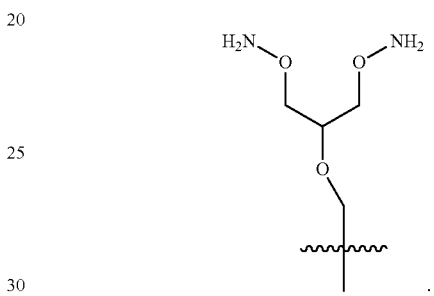
In yet another aspect, R¹ is
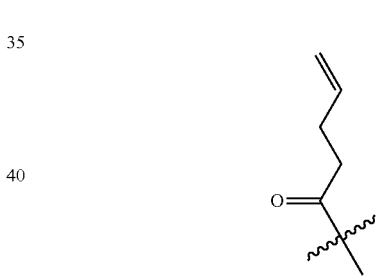
In yet another aspect, R¹ is
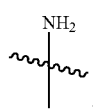
In yet another aspect, R¹ is
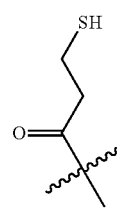

In yet another aspect, R¹ is
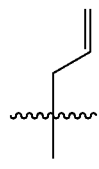 [SMILES: *CC=C]
In one aspect, R² is
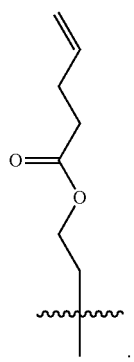 [SMILES: *CCOC(=O)CCC=C]
In another aspect, R² is
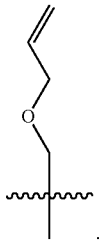
In yet another aspect, R² is
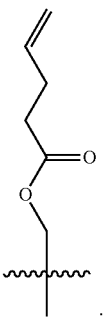
In yet another aspect, R² is
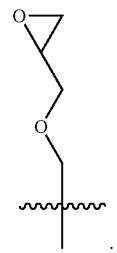
In yet another aspect, R² is
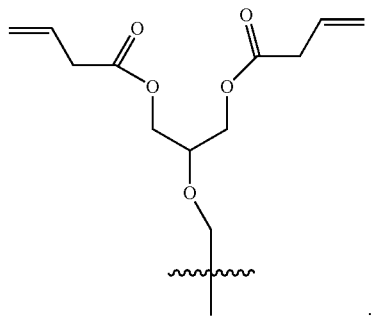 [SMILES: *COC(COC(=O)CC=C)COC(=O)CC=C]
In yet another aspect, R² is
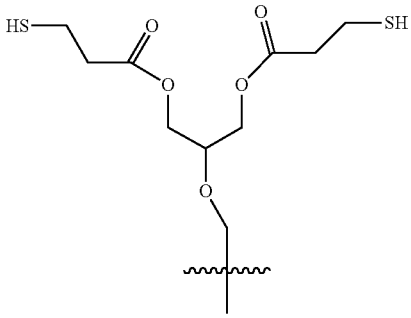 [SMILES: *COC(COC(=O)CCS)COC(=O)CCS]
In yet another aspect, R² is
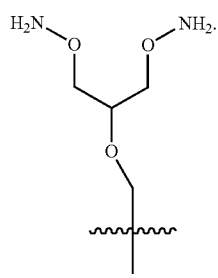

d. Crosslinks and L Groups

In one aspect, crosslinks or $L^1$ comprises

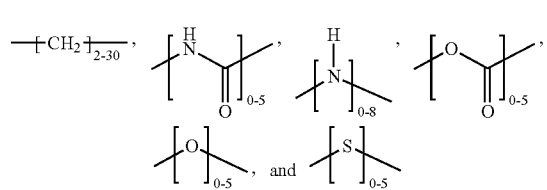

wherein least one of

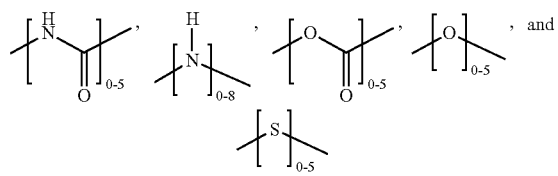

is not 0.

In one aspect, crosslinks or $L^1$ comprises at least

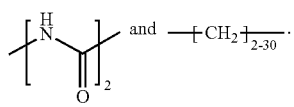

In one aspect, $L^1$ comprises at least

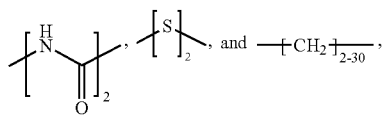

In one aspect, crosslinks or $L^1$ comprises one or more of

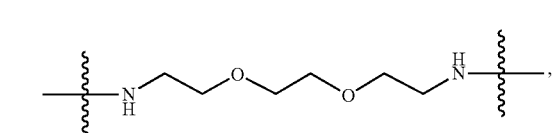

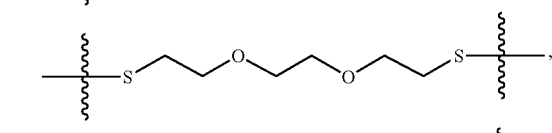

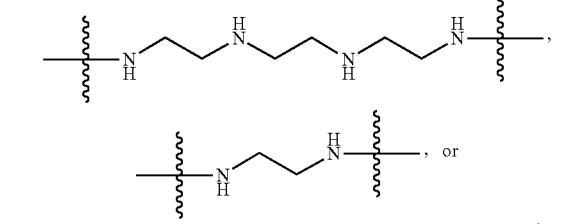

or any combination thereof.

In one aspect, crosslinks or $L^1$ comprises one or more of

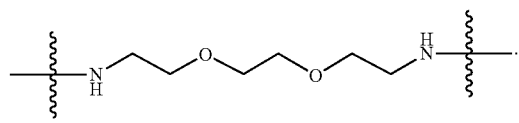 [SMILES: *NCCOCCOCCN*]

In another aspect, crosslinks or $L^1$ comprises one or more of

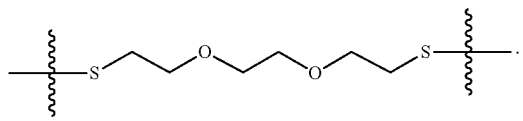 [SMILES: *SCCOCCOCCS*]

In yet another aspect, crosslinks or $L^1$ comprises one or more of

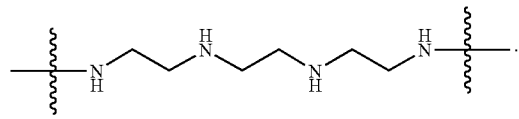 [SMILES: *NCCNCCNCCN*]

In yet another aspect, crosslinks or $L^1$ comprises one or more of

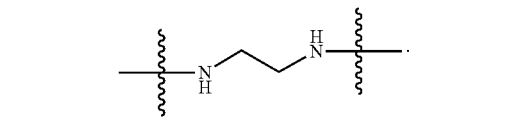

In yet another aspect, crosslinks or $L^1$ comprises one or more of

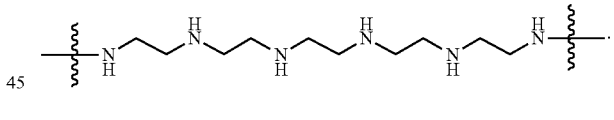

In one aspect, $L^1$ comprises one or more of

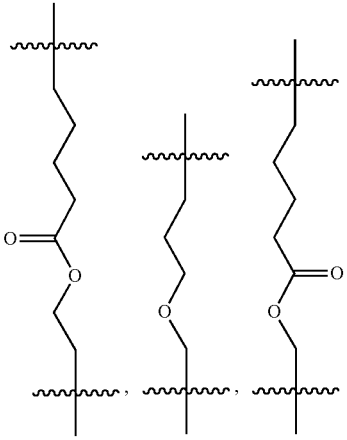

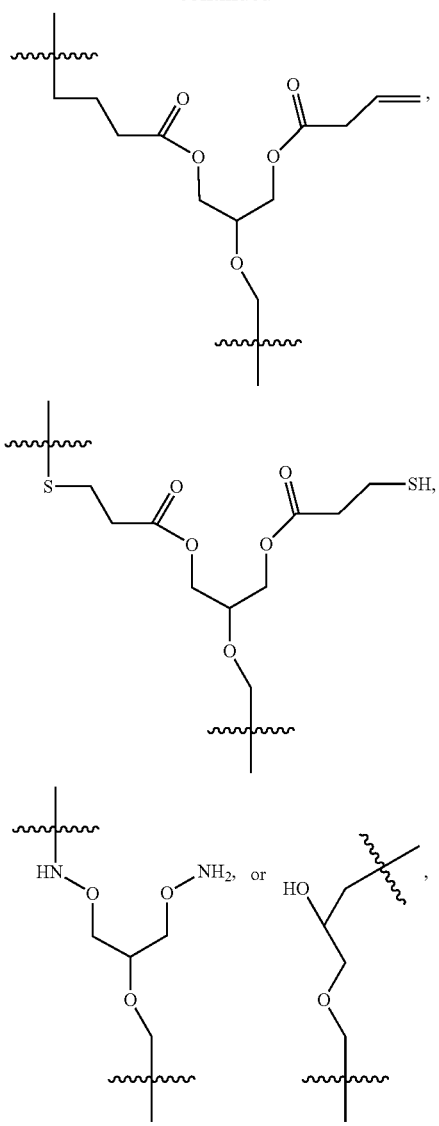
or any combination thereof.
In one aspect, $L^1$ comprises two of
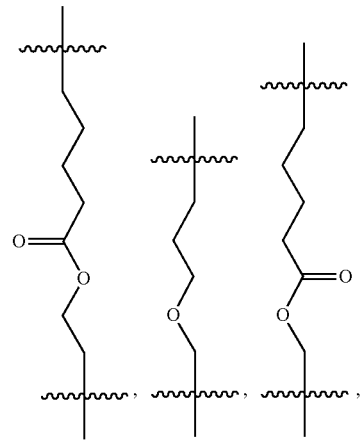
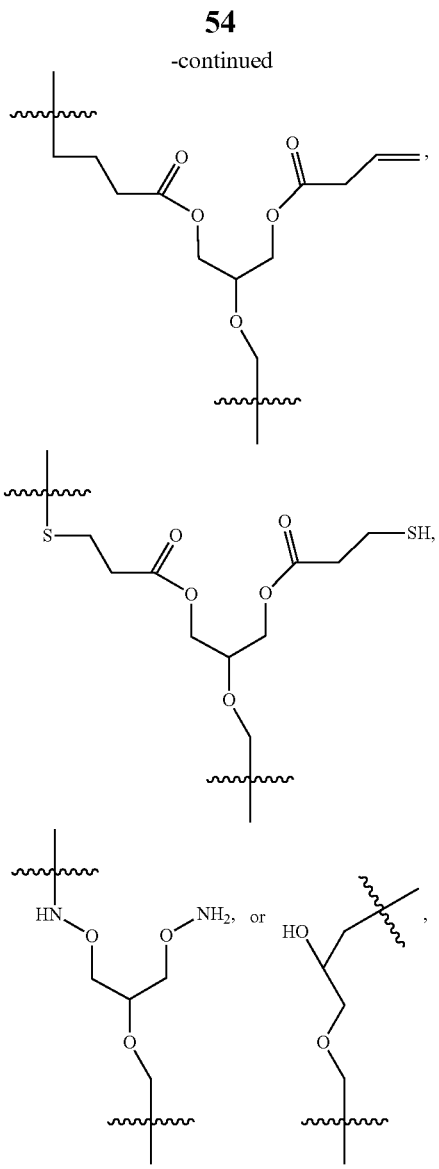
or any combination thereof.
In another aspect, $L^1$ comprises two of
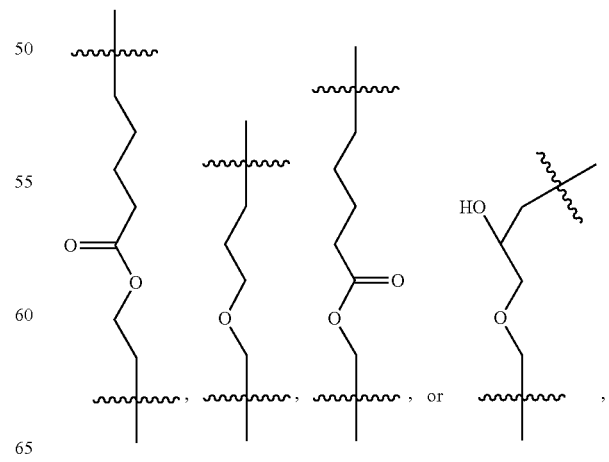
or any combination thereof.

In one aspect, $L^1$ is
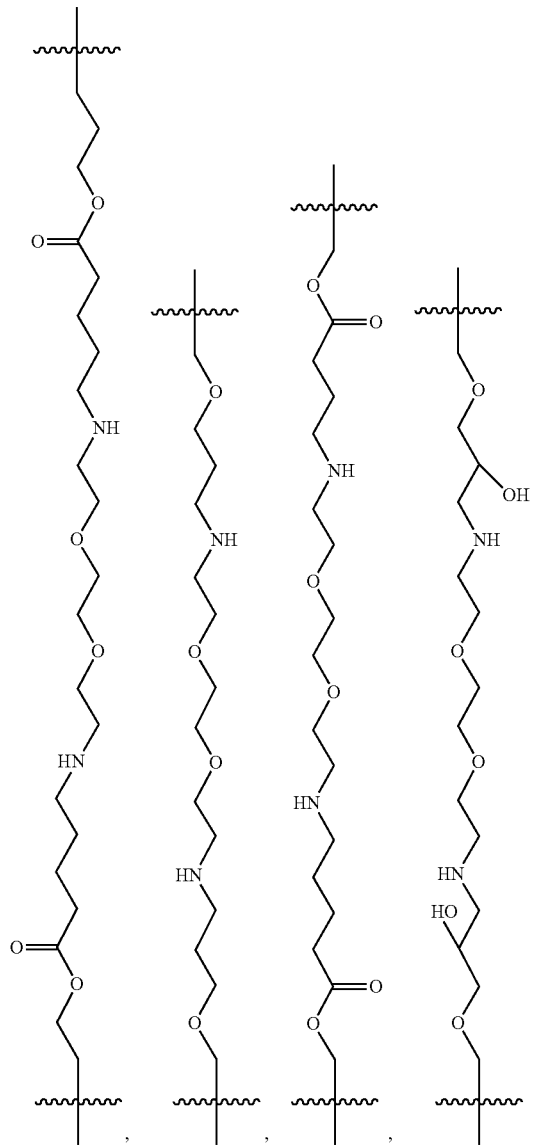
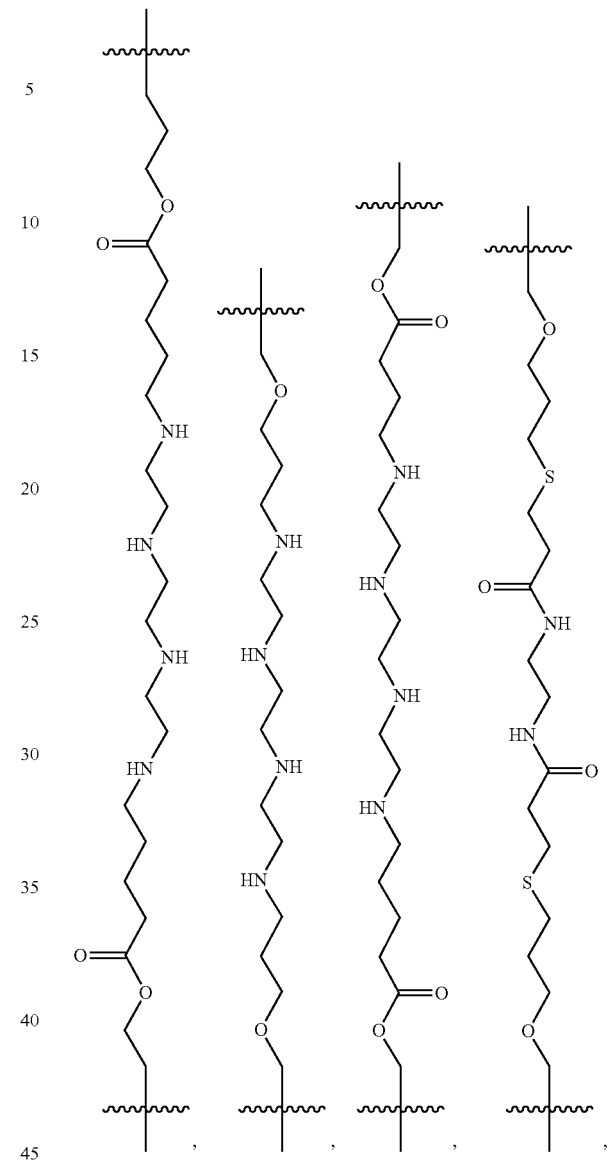

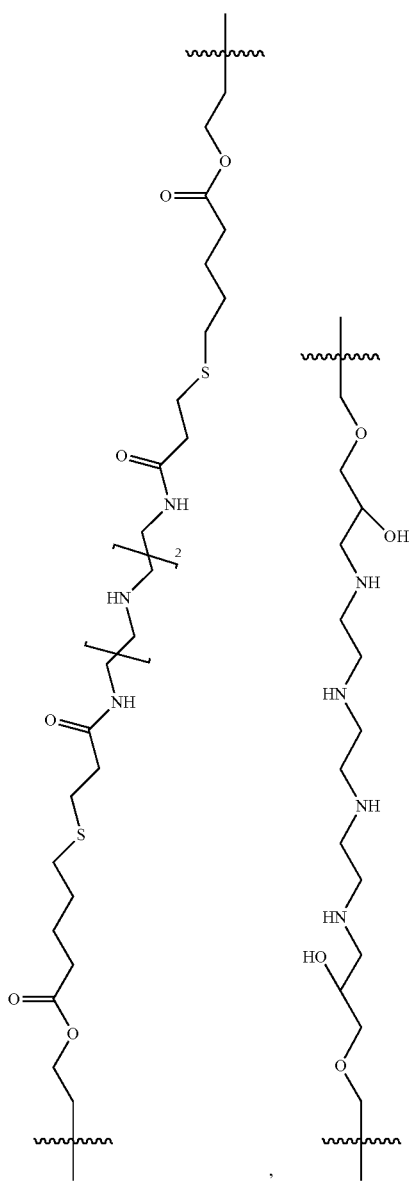
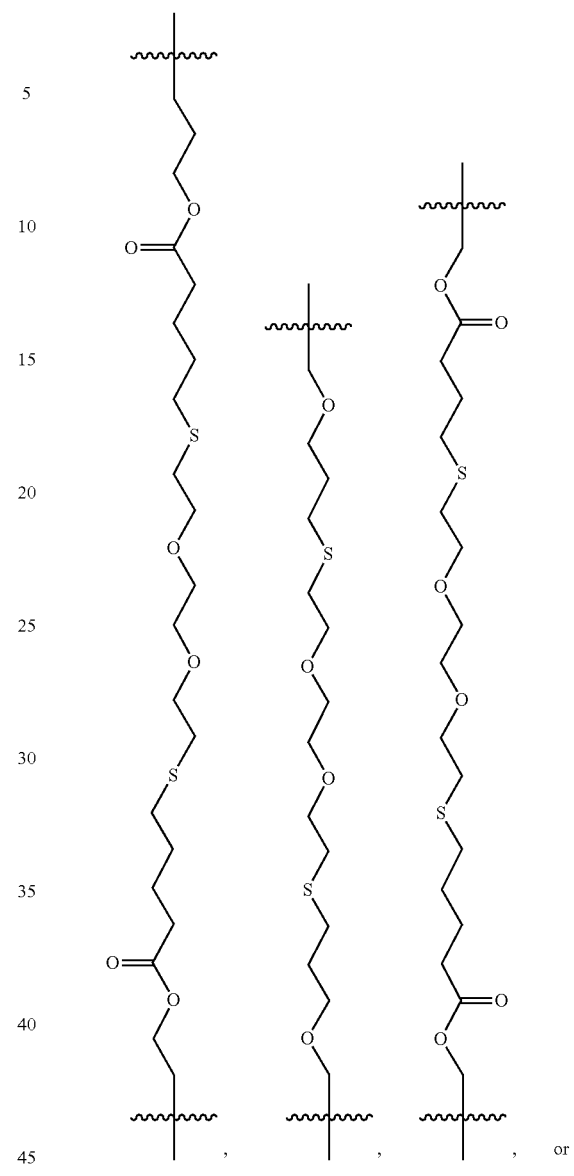

In one aspect, $L^2$ comprises

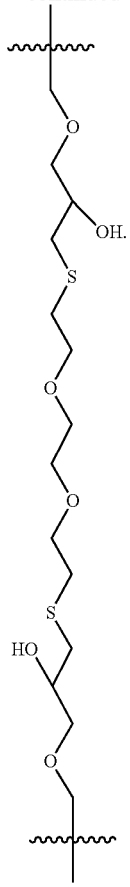 [SMILES: *COCC(O)CSCCOCCOCCSCC(O)COC*]

In one aspect, $L^2$ comprises

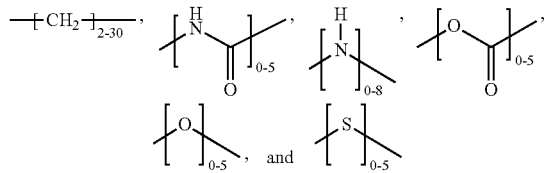

wherein at least one

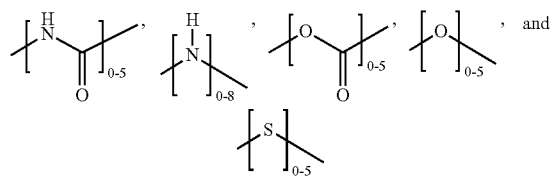

is not 0.

In one aspect, $L^2$ comprises at least

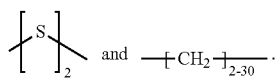

In one aspect, $L^2$ comprises at least

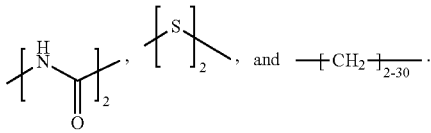

In one aspect, $L^2$ comprises

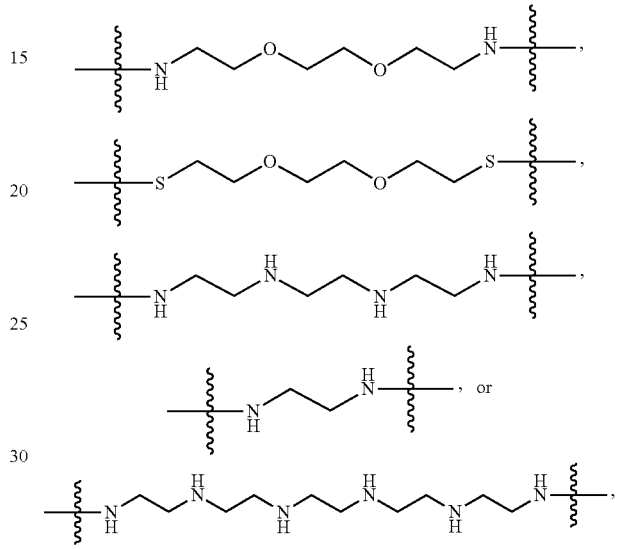

or any combination thereof.

In a further aspect, the invention relates to a polyglycidol having a degree of branching of less than about 0.25. For example, the degree of branching can less than about 0.20, less than about 0.15, or less than about 0.10.

C. Nanoparticles

Also disclosed herein is a nanoparticle comprising one or more compounds or polymers disclosed herein. In one aspect, the nanoparticle is made from one or more compounds or polymers disclosed herein, for example, the nanoparticle is made from one or more polymers disclosed herein. In one aspect, the nanoparticle comprises crosslinked polymers disclosed herein.

In one aspect, the nanoparticle further comprises at least one pharmaceutically active agent and/or biologically active agent.

In one aspect, the nanoparticle is biodegradable. The biodegradability can depend on the number of hydrolysable bonds, such as ester bonds, present in the compounds making up the nanoparticle.

In one aspect, the nanoparticle is hydrophilic. In another aspect, the t at least one pharmaceutically active agent and/or biologically active agent is hydrophobic. In another aspect, the at least one pharmaceutically active agent and/or biologically active agent is a protein, DNA, or SiRNA. In one aspect, the at least one pharmaceutically active agent and/or biologically active agent is covalently bonded to the nanoparticle.

In one aspect, the nanoparticle is between 1 nm and 1000 nm in diameter. In another aspect, the nanoparticle is between 1 nm and 750 nm in diameter. In yet another aspect, the nanoparticle is between 1 nm and 500 nm in diameter. In yet another aspect, the nanoparticle is between 1 nm and 250 nm in diameter. In yet another aspect, the nanoparticle is between 1 nm and 100 nm in diameter.

In one aspect, the nanoparticle comprises reactive functionalities, such as a hydroxyl group, an amine group, a thiol group, an allyl group, an epoxide, or an alkyne group, or a combination thereof.

D. Compositions and Pharmaceutical Compositions

Also disclosed herein are compositions, such as pharmaceutical compositions.

In one aspect, the pharmaceutical composition comprises a) a compound or polymer disclosed herein; b) pharmaceutically active agent and/or biologically active agent; and c) a pharmaceutically acceptable carrier.

In one aspect, the pharmaceutical composition comprises a) a nanoparticle disclosed herein; b) pharmaceutically active agent and/or biologically active agent; and c) a pharmaceutically acceptable carrier.

In one aspect, the invention relates to pharmaceutical compositions comprising the disclosed compounds and/or nanoparticles; pharmaceutically active agent and/or biologically active agent, and a pharmaceutically acceptable carrier or salt thereof. In an aspect, the disclosed pharmaceutical compositions can be provided comprising a therapeutically effective amount of the therapeutic agent, diagnostic agent, or prophylactic agent, or a mixture thereof, and a pharmaceutically acceptable carrier. The disclosed pharmaceutical compositions can be provided comprising a prophylactically effective amount of the therapeutic agent, diagnostic agent, or prophylactic agent, or a mixture thereof, and pharmaceutically acceptable carrier.

In one aspect, the pharmaceutical composition comprises one or more pharmaceutically active agent and/or biologically active agents. The compounds and nanoparticles disclosed herein are capable of being loaded with several different classes of therapeutics. Thus, the pharmaceutical composition is capable of delivering at least two different classes of therapeutics. For example, the therapeutic agent can comprise a MEK inhibitor and a bone morphogenetic protein 2 (BMP2) growth factor. In one aspect, the therapeutic agent is hydrophobic. The compounds and nanoparticles are capable of being a delivery vehicle for therapeutic agents, diagnostic agents, or prophylactic agents that were previously difficult to deliver due to their physical properties, such as their hydrophobicity. In one aspect, an effective amount of a therapeutic agent, diagnostic agent, or prophylactic agent can be present in the pharmaceutical composition. For example, an effective amount of a therapeutic agent, diagnostic agent, or prophylactic agent can be loaded in the compounds or nanoparticles disclosed herein.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for treatment of a disorder in a subject (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound, a therapeutic agent, diagnostic agent, or prophylactic agent, or a mixture thereof, with a pharmaceutically acceptable carrier or diluent.

It is understood that the disclosed compositions can be prepared from the disclosed compounds. It is also understood that the disclosed compositions can be employed in the disclosed methods of using.

a. Methods of Using the Pharmaceutical Compositions

Disclosed herein is a drug delivery method comprising the step of administering to a subject a composition comprising a polymer or nanoparticle disclosed herein, in combination with at least one pharmaceutically active agent and/or biologically active agent. In one aspect, the composition further comprises a pharmaceutically acceptable carrier. In one aspect, the method comprises administering an effective amount of the pharmaceutically active agent and/or biologically active agent to the subject. In one aspect, the effective amount is a therapeutically effective amount. Such amount can be determined by one skilled in the art.

In one aspect, the therapeutic agent is a cancer agent. In another aspect, the therapeutic agent is a protein, DNA, or SiRNA.

In one aspect, the subject is an animal. In a further aspect, the subject is a mammal. In a yet further aspect, the subject is a primate. In a still further aspect, the subject is a human. In an even further aspect, the subject is a patient.

In a further aspect, the pharmaceutical composition is administered following identification of the subject in need of treatment of disorder. In a still further aspect, the pharmaceutical composition is administered following identification of the subject in need of prevention of a disorder. In an even further aspect, the subject has been diagnosed with a need for treatment of a disorder prior to the administering step.

In one aspect, the method delivers one or more therapeutic agents. The compounds and nanoparticles disclosed herein are capable of being loaded with several different classes of therapeutics. Thus, the method is capable of delivering at least two different classes of therapeutics. For example, the therapeutic agent can comprise a MEK inhibitor and a bone morphogenetic protein 2 (BMP2) growth factor.

In one aspect, the method comprises administering an effective amount of the pharmaceutically active agent and/or biologically active agent to the subject. In one aspect, the effective amount is a therapeutically effective amount. Such amount can be determined by one skilled in the art.

In one aspect, the therapeutic agent is a cancer agent. In another aspect, the pharmaceutically active agent and/or biologically active agent is a protein, DNA, or SiRNA.

In one aspect, the subject is an animal. In a further aspect, the subject is a mammal. In a yet further aspect, the subject is a primate. In a still further aspect, the subject is a human. In an even further aspect, the subject is a patient.

In a further aspect, the pharmaceutical composition is administered following identification of the subject in need of treatment of disorder. In a still further aspect, the pharmaceutical composition is administered following identification of the subject in need of prevention of a disorder. In an even further aspect, the subject has been diagnosed with a need for treatment of a disorder prior to the administering step.

E. Method of Making Polymers

Also disclosed here is a method of making a polymer, the method comprising the step of polymerizing glycidol in the presence of a tin catalyst. In one aspect, the tin catalyst is a tin(II) catalyst, for example, $Sn(OTf)_2$.

Also disclosed is a polymer made from the methods disclosed herein. For example, the resultant polymer comprises repeating units selected from:

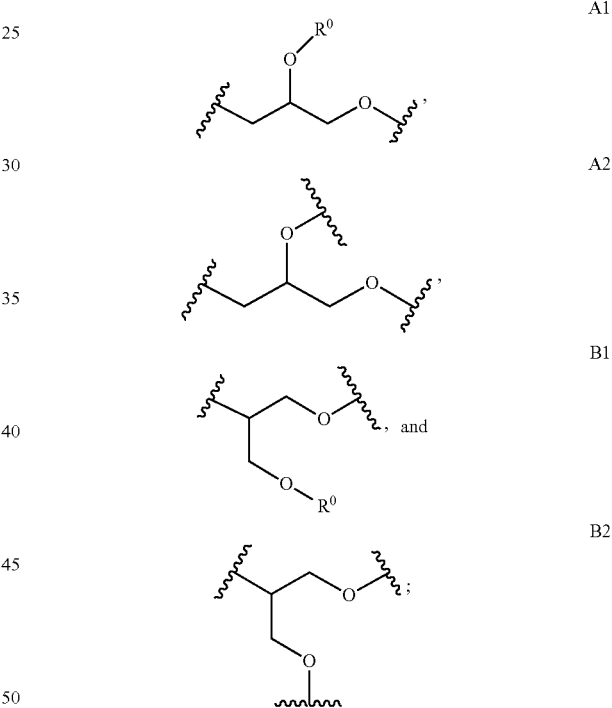

wherein $R^0$ is selected from H, alkyl, $NH_2$, and $R^1$; wherein $R^1$ comprises a crosslinking functionality; wherein repeating units A1, A2, B1, and B2 account for at least about 50 wgt % of the polymer; and wherein the ratio of (A1+A2):(B1+B2) is greater than 1.

In another aspect, the resultant polymer further comprises at least one repeating unit formed from a monomer selected from:

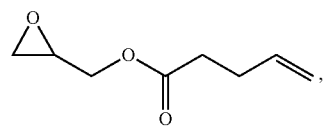

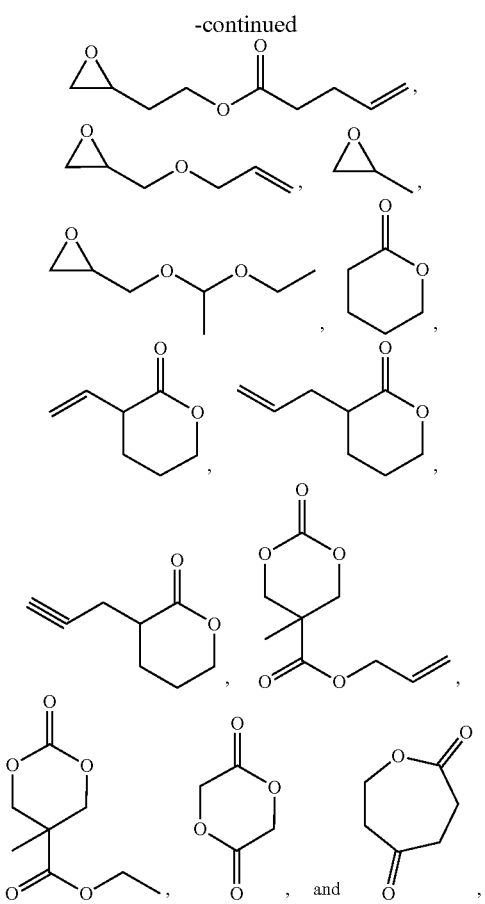

or a combination thereof.

In one aspect, the method further comprises the step of crosslinking the polymer with crosslinks, wherein the wherein the crosslinks comprises

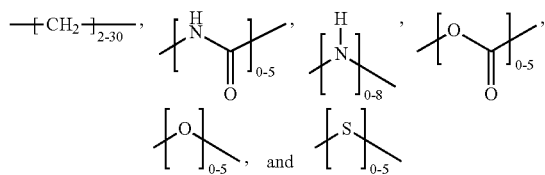

wherein at least one of

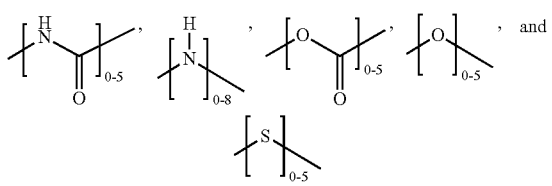

is not 0.

In another aspect, the polymer is linear when the first compound comprises an ester moiety. In another aspect, the polymer is semi-branched when the first polymer comprises a glycidol moiety. Non-limiting examples of first compounds comprising an ester moiety are 2-oxepane-1,5-dione and lactones, such as δ-valerolactone and α-allyl-δ-valerolactone. Non-limiting examples of first compounds comprising a glycidol moiety are glycidol, allyl-glycidol ether, glycidyl ester allyl, and ethoxyethyl glycidyl ether. In one aspect, the method comprises polymerizing the first compound comprising a glycidol moiety and/or an ester moiety with a second compound comprising a glycidol moiety and/or a ester moiety, thereby making a copolymer. In one aspect, the first compound comprises a glycidol moiety and the second compound comprises an ester moiety. In one aspect, the first compound comprises a glycidol moiety and the second compound comprises a glycidol moiety and an ester moiety.

In one aspect, the polymerization step is performed at a temperature of from −30° C. to 50° C. In another aspect, the polymerization step is performed at a temperature of from −30° C. to 20° C. In yet another aspect, the polymerization step is performed at a temperature of from −30° C. to 0° C. In yet another aspect, the polymerization step is performed at a temperature of from −30° C. to −10° C.

Also disclosed herein is a method of crosslinking comprising: a) providing a first and second compound, wherein both the first and second compound comprises a crosslinking functionality; b) crosslinking the first and second compound with a crosslinks described herein.

F. Manufacture of a Medicament

In one aspect, the invention relates to a method for the manufacture of a medicament for treatment of a disorder comprising combining a disclosed compound or nanoparticle with a therapeutically effective amount of a therapeutic agent, diagnostic agent, or prophylactic agent, or a mixture thereof and with a pharmaceutically acceptable carrier or diluent.

G. Kits

Disclosed herein is a kit comprising a compound or nanoparticle disclosed herein and a therapeutic agent, diagnostic agent, or prophylactic agent, or a mixture thereof and one or more of: a) instructions of delivering the therapeutic agent, diagnostic agent, or prophylactic agent, or a mixture thereof; b) instructions for using the therapeutic agent, diagnostic agent, or prophylactic agent, or a mixture thereof to treat a disorder.

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 6:
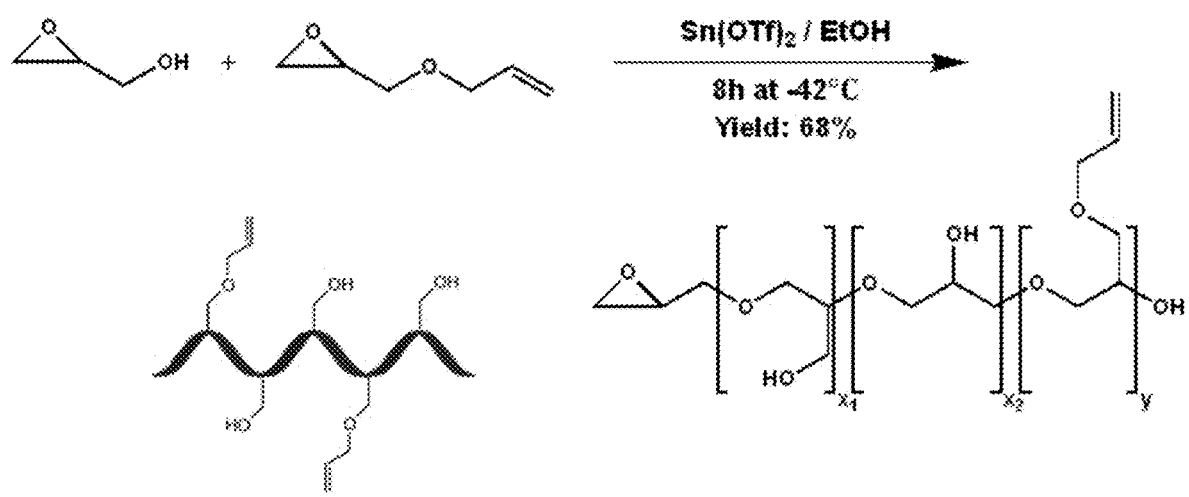
FIG. 6 shows a schematic representation of a reaction scheme for the introduction of allyl functionalities in the polymer systems of the present invention.
Figure 27:
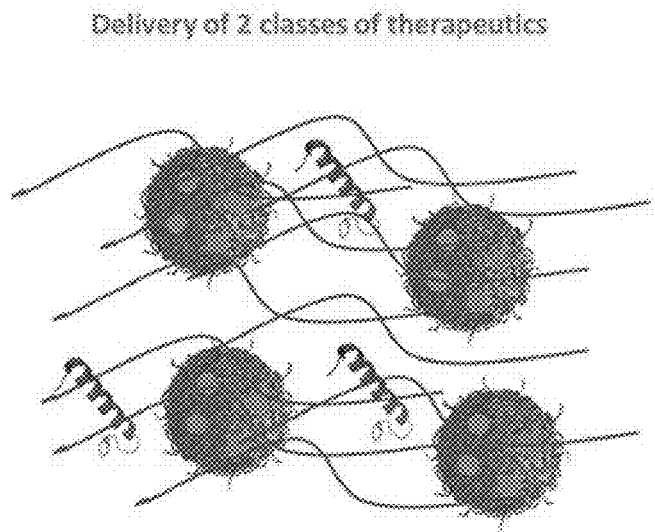
FIG. 27 shows a schematic representation of an exemplary two component delivery system of the present invention.
Figure 27:
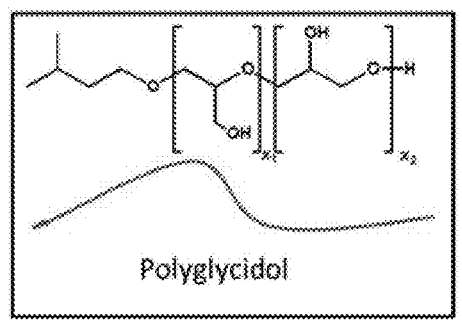
Figure 27:
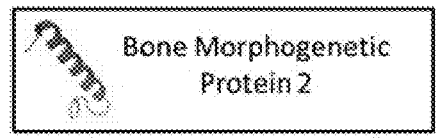
Figure 27:
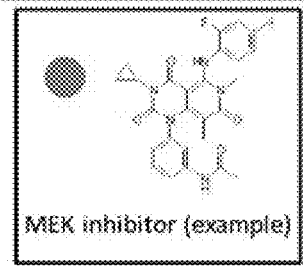
Figure 28:
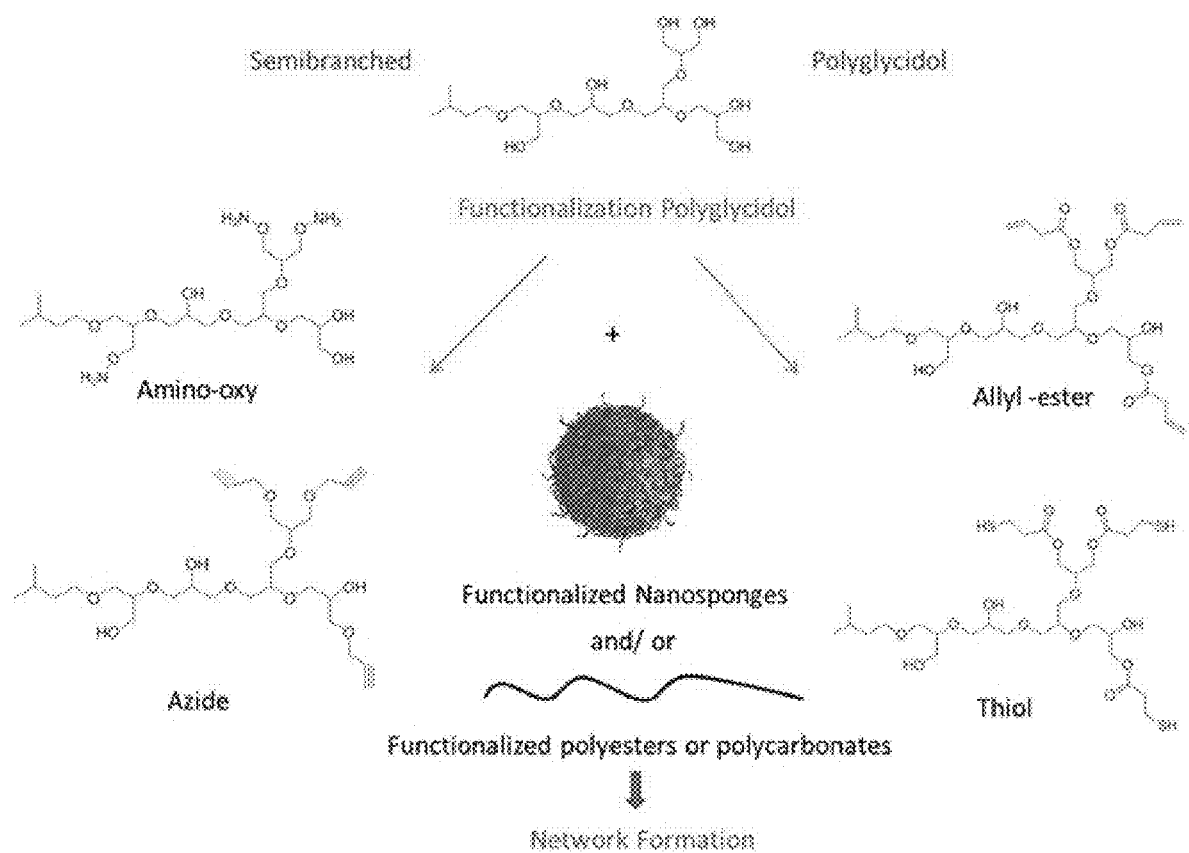
FIG. 28 shows a schematic representation of exemplary reconfigurable and responsive network systems of the present invention.

As briefly discussed above, while hyperbranched systems formed through the polymerization of glycidol have shown applicability, the ability to form polymers with a controlled degree of branching was investigated. In one aspect, controlled polymerization can allow the lower branching systems to achieve a better clearance but also allow the formation of nanoparticles which is not possible with globular starticel materials. The semibraching retain some benefits of the hyperbranched systems for the functionalization and hydrogels formation with and without stimuli-responsive reactions (FIG. 27-28). Without wishing to be bound by a particular theory, it is believed that the secondary reaction ability will impart a wider range of versatility to the already robust poly(glycidol) architecture. In a further aspect, the increase in post-modification capability will increase the viability of the synthesized polymer systems and allow for novel macromolecules. As depicted in FIG. 6, introduction of allyl functionalities, in one aspect, can allow for the formation of a more robust polymer system with crosslinking potential.

In a still further aspect, controlled degree of branching and linear systems which can be synthesized more easily can used for targeted delivery of drug molecules and biological cargo. In a yet further aspect, semi-branched structures with that are more favorable in vivo.

Figure 7:
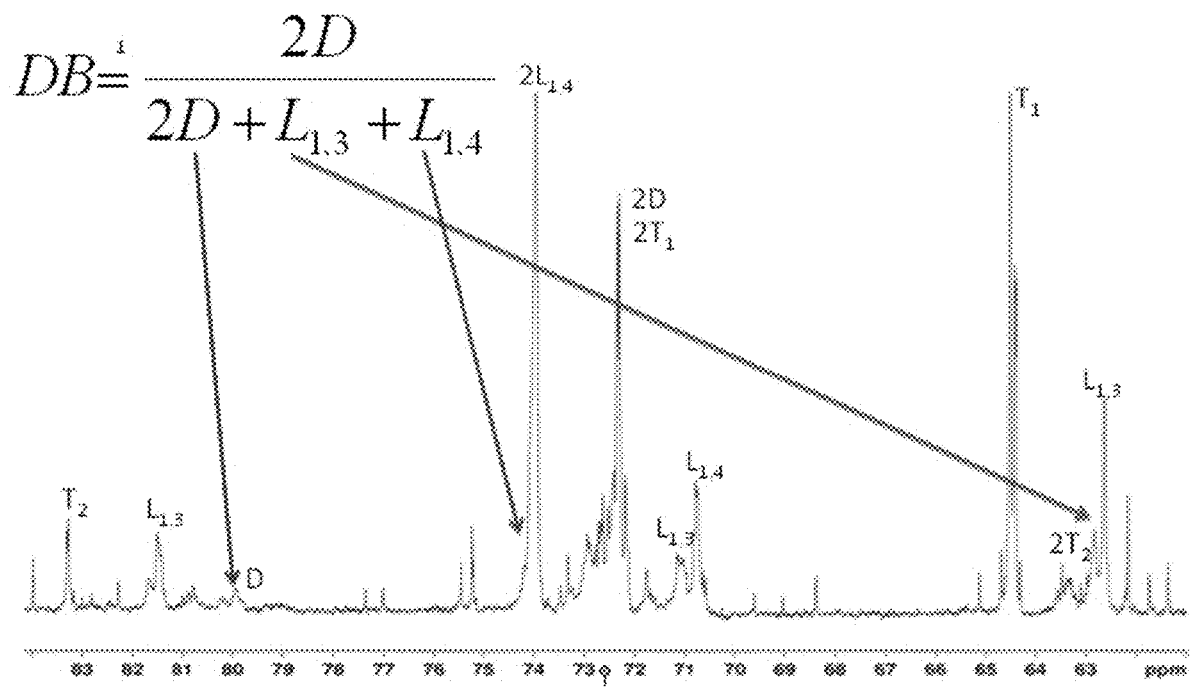
FIG. 7 shows the equation for degree of branching in the resultant polymers with the variables referring to the integration values obtained from quantitative $^{13}$CNMR investigation of the present invention.
Figure 8:
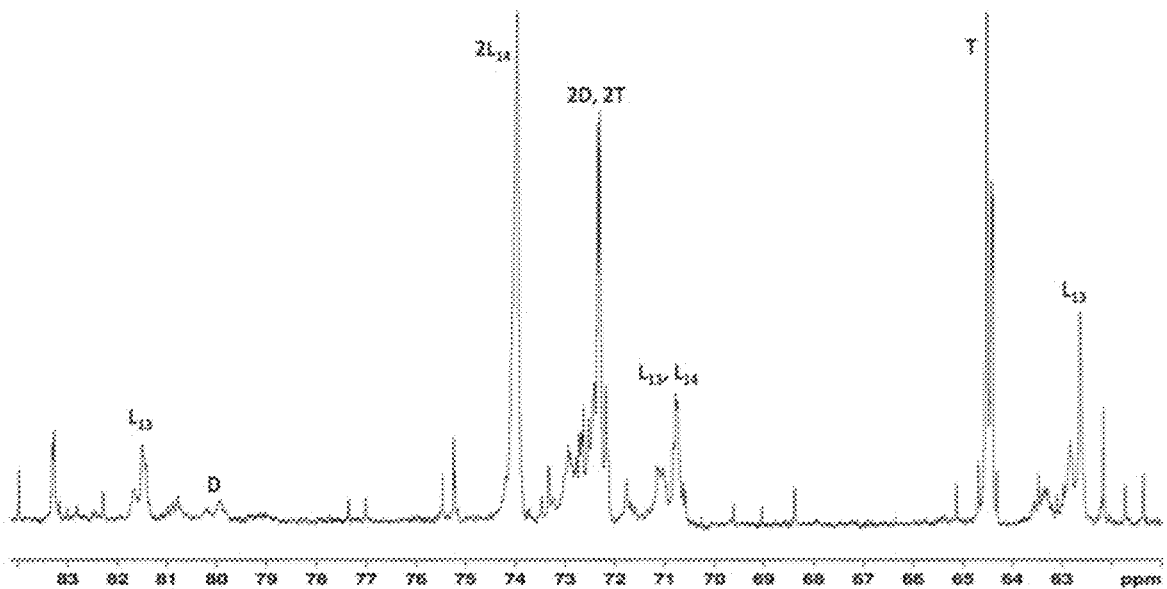
FIG. 8 shows $^{13}$C-NMR spectra of glycidol homopolymer of the present invention.

In various aspects, the ring opening polymerization of glycidol can be influenced kinetically. In the present example, the kinetic control on the polymerization of poly (glycidol) was evaluated. To evaluate the kinetics of the polymer system, four temperatures were chosen in order to undergo a thorough kinetic study on the ring opening polymerization mechanism. The temperatures chosen are shown in Table 1, below. The degree of branching in the resultant polymers can be calculated using equation 1 shown below, with the variables referring to the integration values obtained from quantitative $^{13}$CNMR investigation, as further shown in FIG. 7. Unique peaks arise in the 13C-NMR based on the type of ring opening undergone by each monomer. The $^{13}$C-NMR of glycidol homopolymer is shown in FIG. 8.

$$DB = \frac{2D}{2D + L_{1,3} + L_{1,4}} \quad \text{(Eq. 1)}$$

Figure 9:
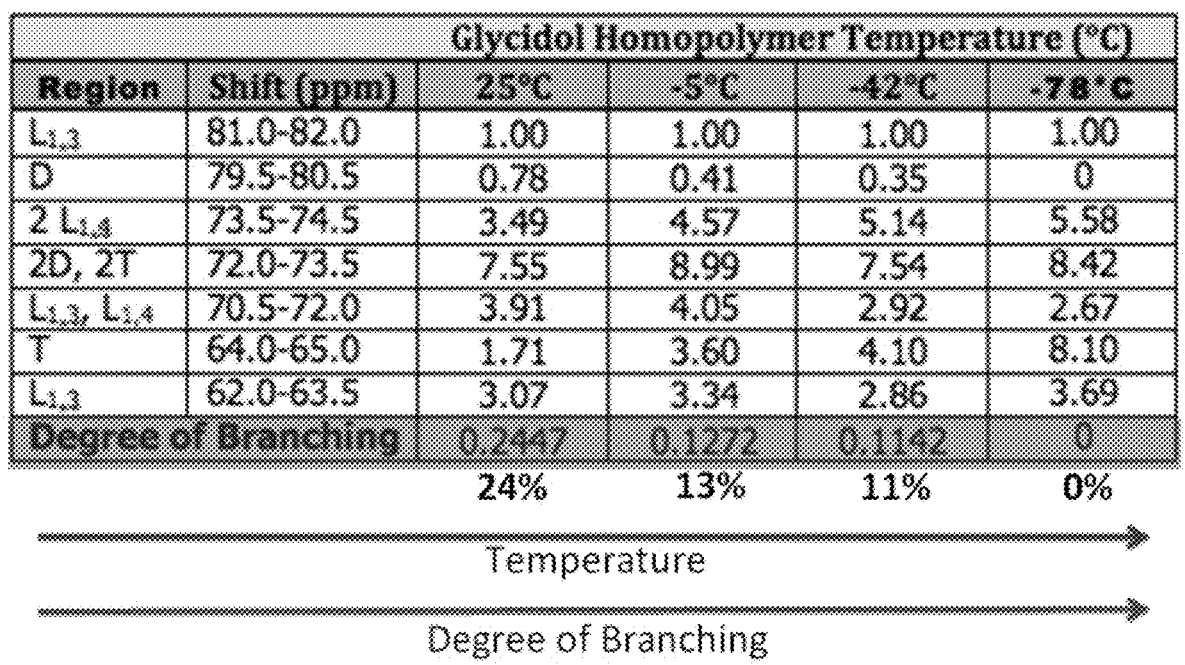
FIG. 9 shows a table reporting experimental NMR data and degree of branching for polyglycidol systems of the present invention.
Figure 10:
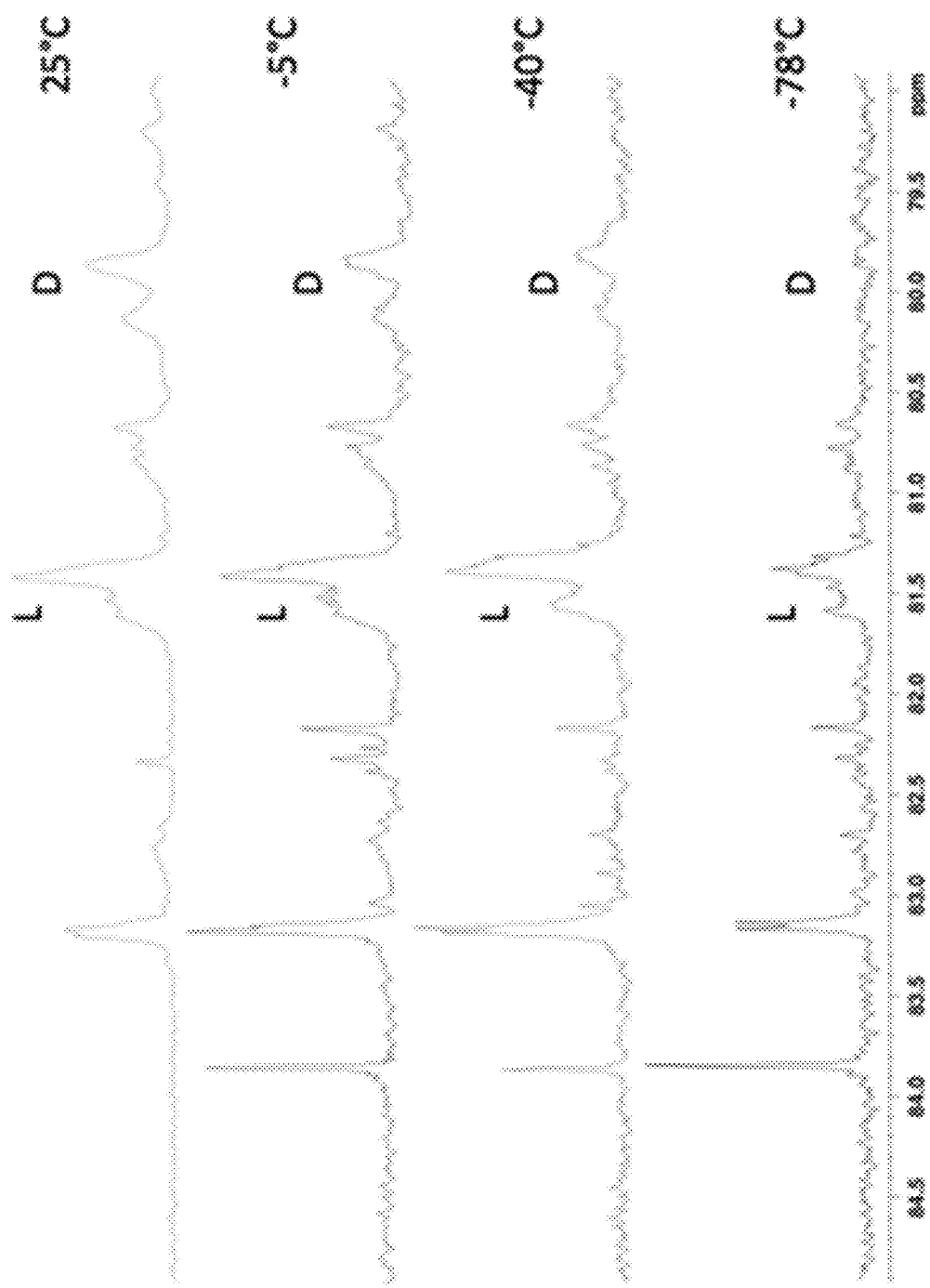
FIG. 10 shows a visual representation of depression of dendritic peak through kinetically controlled reactions of the present invention.

For the purpose of direct correlation, the only variable that was changed for each reaction was the temperature. NMR data and degree of branching for polyglycidol systems are reported in Table 1 below. As shown in Table 1 and FIG. 9, kinetic control over the degree of branching in the polymer systems was accomplished by depressing the temperature at which the reaction was conducted. Inspection of the NMR data (FIG. 10) shows the suppression of the dendritic carbon peak while the linear peak remains strong. Thus, depressed reaction temperatures reduce the formation of branches within the polymer backbone. In a further aspect, these results allows for the determination of an optimal reaction temperature based on the degree of branching that is desired for the various applications proposed for the synthesized polymers.

TABLE 1

| Glycidol Homopolymer Reaction Temperature (° C.) | | | | | |
|---|---|---|---|---|---|
| Region | Shift (ppm) | 40° C. | 20° C. | 0° C. | −20° C. |
| $L_{1,3}$ | 81.0-82.0 | 1.00 | 1.00 | 1.00 | 1.00 |
| D | 79.5-80.5 | 0.79 | 0.62 | 0.60 | 0.48 |
| 2 $L_{1,4}$ | 73.5-74.5 | 3.69 | 3.65 | 3.98 | 4.80 |

TABLE 1-continued

| Glycidol Homopolymer Reaction Temperature (° C.) | | | | | |
|---|---|---|---|---|---|
| 2D, 2T | 72.0-73.5 | 7.05 | 7.52 | 7.62 | 8.44 |
| $L_{1,3}$, $L_{1,4}$ | 70.5-72.0 | 3.14 | 3.01 | 3.17 | 2.93 |
| T | 64.0-65.0 | 1.74 | 2.13 | 2.17 | 3.53 |
| $L_{1,2}$ | 62.0-63.5 | 3.15 | 2.97 | 2.76 | 2.87 |
| Degree of Branching | | 0.24 | 0.21 | 0.20 | 0.15 |
| Relative Abundance of Dendritic Carbons | | 10.5% | 8.2% | 8.0% | 5.2% |
| Region | Shift (ppm) | 25° C. | −5° C. | −42° C. | −78° C. |
| $L_{1,3}$ | 81.0-82.0 | 1.00 | 1.00 | 1.00 | 1.00 |
| D | 79.5-80.5 | 0.78 | 0.41 | 0.35 | 0 |
| 2 $L_{1,4}$ | 73.5-74.5 | 3.49 | 4.57 | 5.14 | 5.58 |
| 2D, 2T | 72.0-73.5 | 7.55 | 8.99 | 7.54 | 8.42 |
| $L_{1,3}$, $L_{1,4}$ | 70.5-72.0 | 3.91 | 4.05 | 2.92 | 2.67 |
| T | 64.0-65.0 | 1.71 | 3.60 | 4.10 | 8.10 |
| $L_{1,3}$ | 62.0-63.5 | 3.07 | 3.34 | 2.86 | 3.69 |
| Degree of Branching | | 0.2447 | 0.1272 | 0.1142 | 0 |

Figure 11:
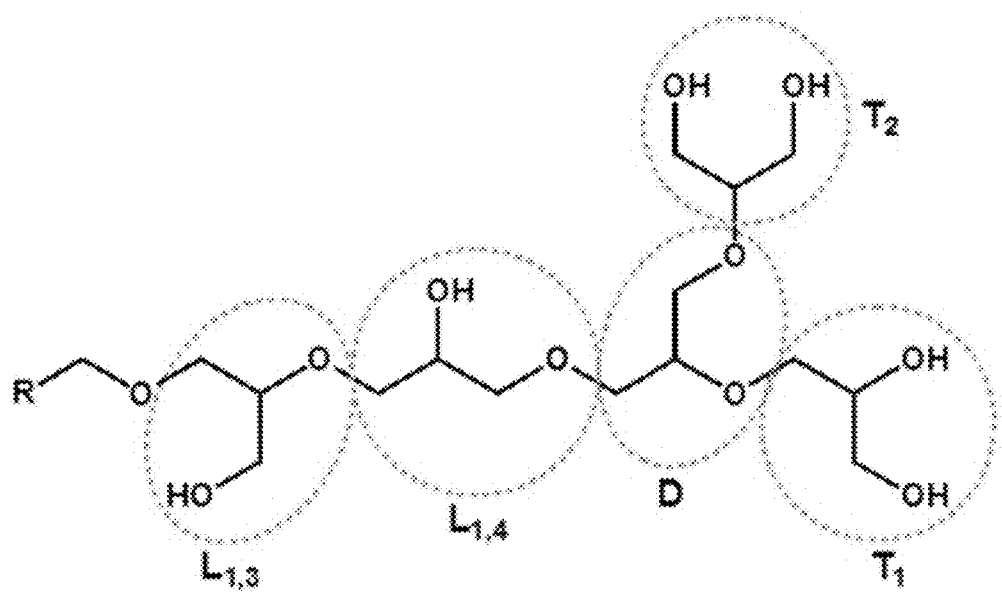
FIG. 11 shows a visual representation of poly(glycidol) branching possibilities.
Figure 12:
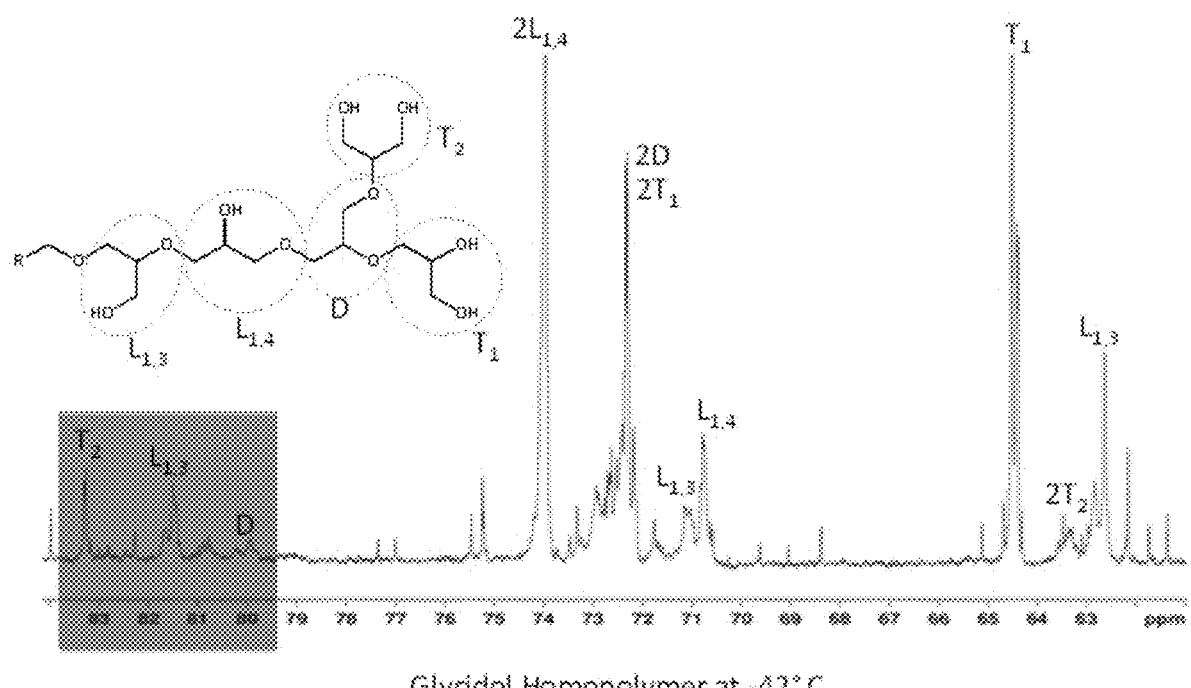
FIG. 12 shows NMR spectra and a visual representation of poly(glycidol) branching possibilities.

The capability to choose the degree of branching optimized for the poly(glycidol) system affords the ability to modify the synthesized polymers based on the preferred application for each. This possibility indicates that the present invention can be used in a wide range of applications with the reaction temperature being the determining factor for the polymer architecture. Without wishing to be bound by a particular theory, such control over this synthetic method allows for more effective and diverse potential. Poly(glycidol) branching possibilities are shown in FIGS. 11 and 12.

Figure 13:
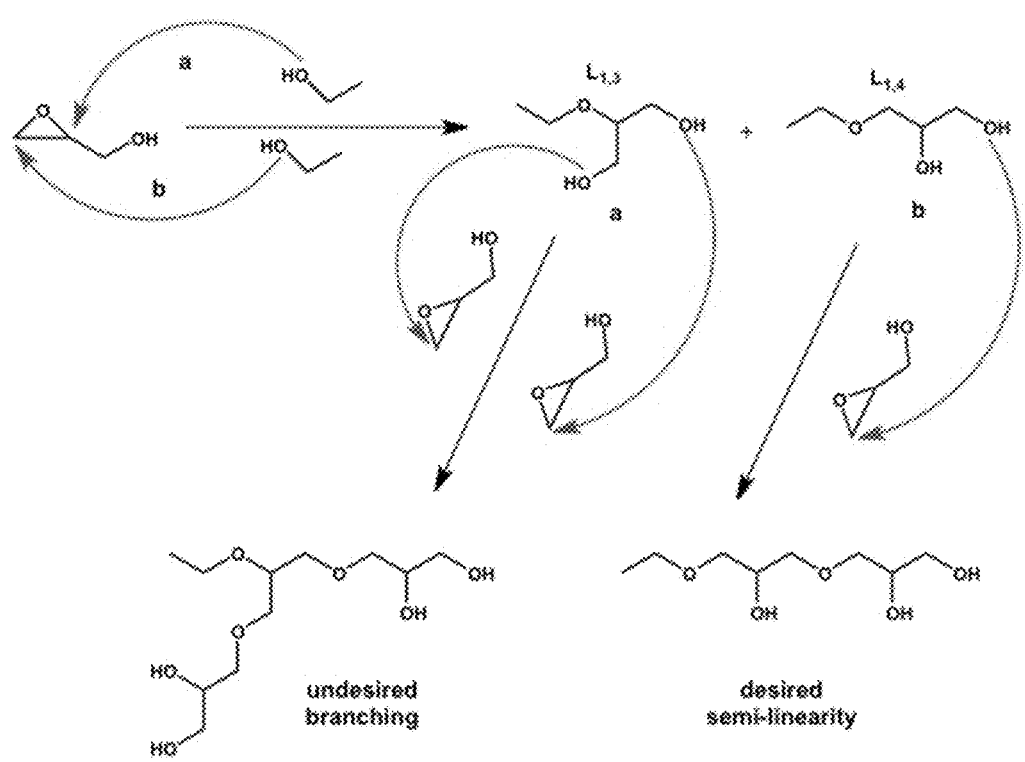
FIG. 13 shows a schematic representation of ring opening possibilities for polyglycidol systems.

In various aspects, the glycidol monomer can be opened in two ways to yield different polymer units.[4, 22, 24, 36] As seen in FIG. 13, these repeat units are known as linear-1,3 ($L_{1,3}$) and linear-1,4 ($L_{1,4}$) and influence the branching that is seen in the polymer products. In a still further aspect, the undesired branching point can be alleviated through two main methods: kinetically, as previously described, and through the use of glycidol derivatives.

In a further aspect, the use of the glycidol derivatives forces the epoxide ring to open exclusively into the $L_{1,3}$ orientation. While this is undesired in certain glycidol homopolymer embodiments, the absence of the primary hydroxyl group does not allow branching of the polymer to take place. In a still further aspect, the absence of the primary hydroxyl group increases the linearity of the polymer product and, when coupled with depressed reaction temperatures, gives polymers with very small degrees of branching. In a yet further aspect, the use of protected glycidol units can yield polymers that are completely linear and can subsequently be deprotected to yield linear glycidol polymers with the restored primary hydroxyl groups.[29]

The objective of the following example was to form a polymer with the increased solubility of glycidol-based polymers but the biodegradability of polyesters. In a further aspect, a molecule was formulate that incorporated the rapid reaction rate of glycidol with the physiological degradability of polyesters. In a still further aspect, this formulation would allow incorporation of the desired characteristics without sacrificing the low reaction conditions needed to impart a high degree of linearity into the system.

In a first trial, glycidol was reacted directly with 4-pentenoyl chloride. Despite the use of pyridine, the excess acid formed in the reaction was enough to cause an opening of the strained epoxide ring, yielding a mixture of products, none of which were desired, as represented by the reaction scheme below.

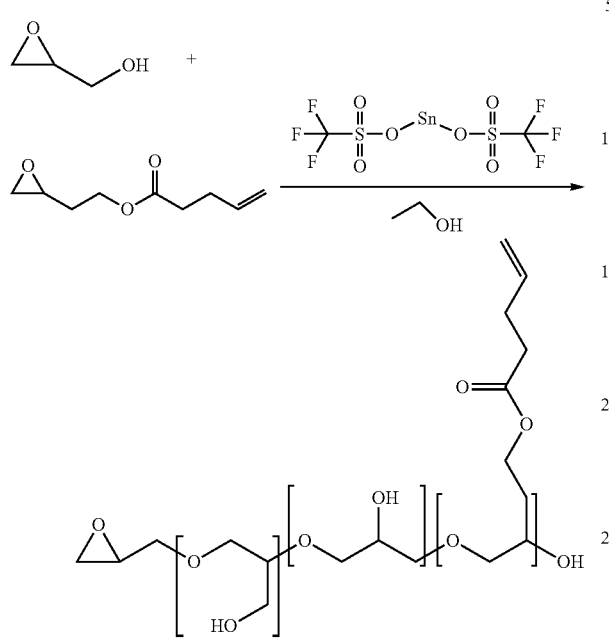

In a subsequent trial, an alternative method was used in which a diallyl intermediate was employed following the reaction scheme below.

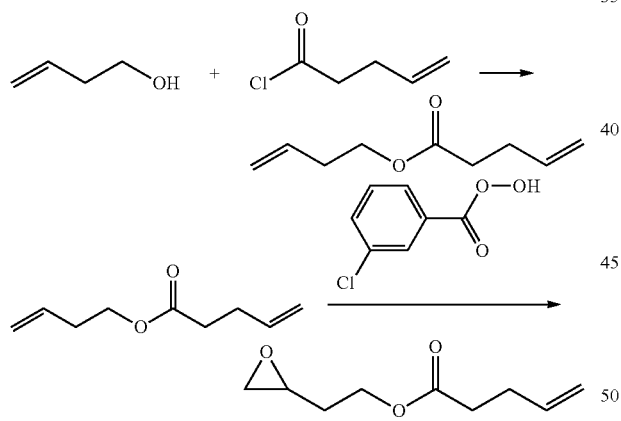

In order to achieve this molecule, 4-pentenoyl chloride was reacted with 3-buten-1-ol in a 1:1 ratio to yield a diallyl species with an ester in the center. This molecule was then oxidized using m-CPBA to afford a clear liquid product that was determined to have an epoxide on the oxygen side of the ester while maintaining the allyl functionality on the carbonyl side.

Figure 14:
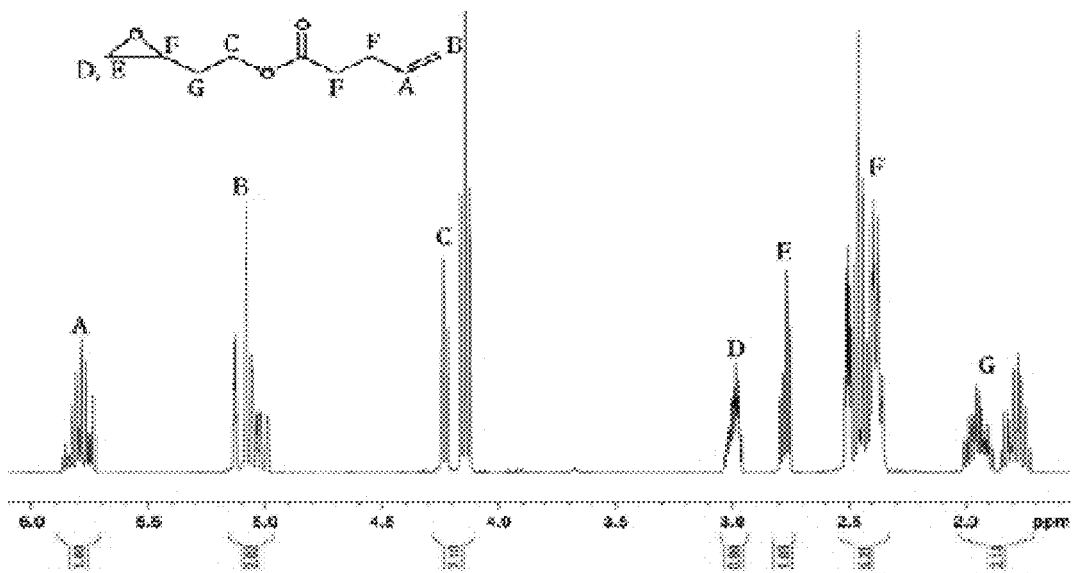
FIG. 14 shows NMR spectra for glycidyl ester allyl of the present invention.

As shown in FIG. 14, this new species was confirmed through 2-D NMR techniques and appeared poised to overcome both the degradability problems of homoglycidol systems as well as the homoglycidol system's lack of post-modification units.

Next, in order to force linearity into the system, a protected glycidol derivative was added to the list of possible monomers. Ethoxyethyl glycidyl ether (EEGE) was chosen as a viable candidate as its protected side arm is similar in bulk to that of the newly synthesized glycidyl ester allyl (GEA), following the reaction scheme below.

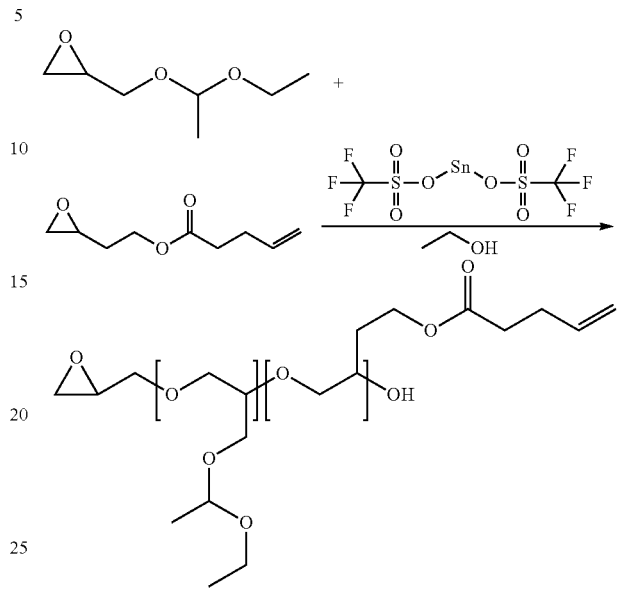

With the similar steric bulkiness, it was believed that both EEGE and GEA will polymerize at similar rates, allowing for a controlled copolymerization of the two monomers. In a further aspect, the presence of the EEGE can also allow for subsequent deprotection, which can yield a completely linear polymer with a plethora of hydroxyls, esters, and allyls.

Synthesis of Degradable and Non-Degradable Glycidol Based Copolymers

To remedy the physiological degradability issues as well as the post-modification limitations of the glycidol homopolymers, a range of copolymers was produced. First, the degradability of the synthesized polymers was increased and subsequently an increased degree of post-modification units was introduced. These two problems were first addressed individually and then a more complete method was devised.

For increased degradability, first attempts were aimed at the incorporation of polyester sections into the backbone of the polymers through the incorporation of 5-valerolactone (VL) as a comonomer with the glycidol monomer, according to the reaction scheme below.

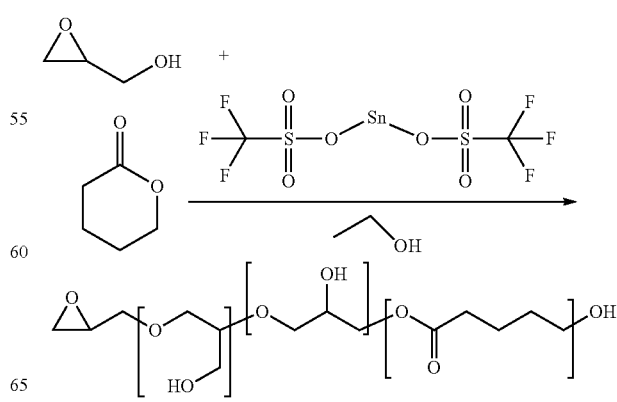

However, the stringent reaction conditions that yield the lowest glycidol branching do not allow for a high incorporation of the lactones. The decision was made to give up some of the control over the branching in order to increase the lactone incorporation. Unfortunately, the lowest temperature at which the polymerization could be run without the lactone freezing was 10° C. Even at these elevated temperatures, the large difference in polymerization kinetics did not allow for a high degree of incorporation.

Next, allyl glycidyl ether (AGE) was used to introduce allyl functionalities into the backbone of the polymer, thus alleviating the poor post-modification potential of poly(glycidol). This reaction, shown in the reaction scheme below, was successful, yielding polymers with allyl units dispersed throughout the structure.

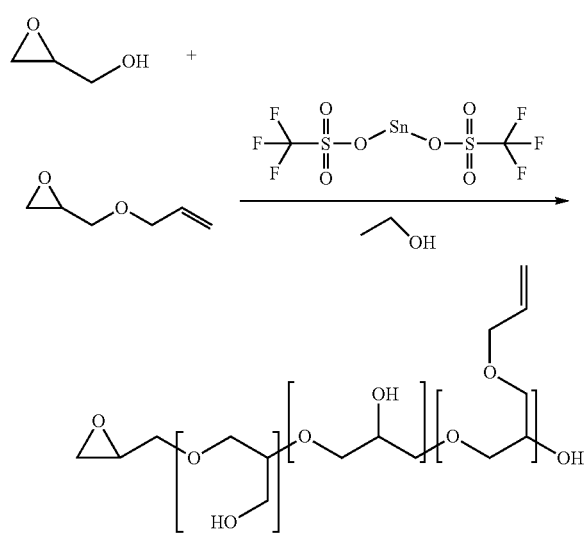

However the lack of a readily degradable unit meant that the synthesized polymers could serve little purpose apart from illuminating the cross-linking ability of the new, semi-branched structures.

Next, the newly synthesized GEA monomer was incorporated into glycidol, according to the reaction scheme below.

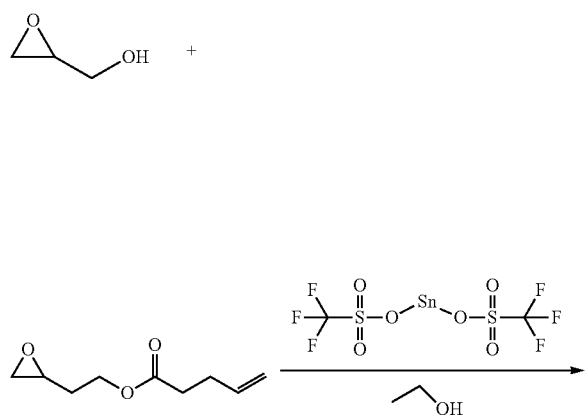

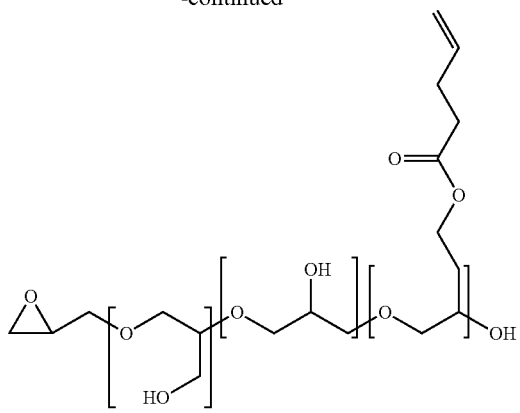

Figure 15:
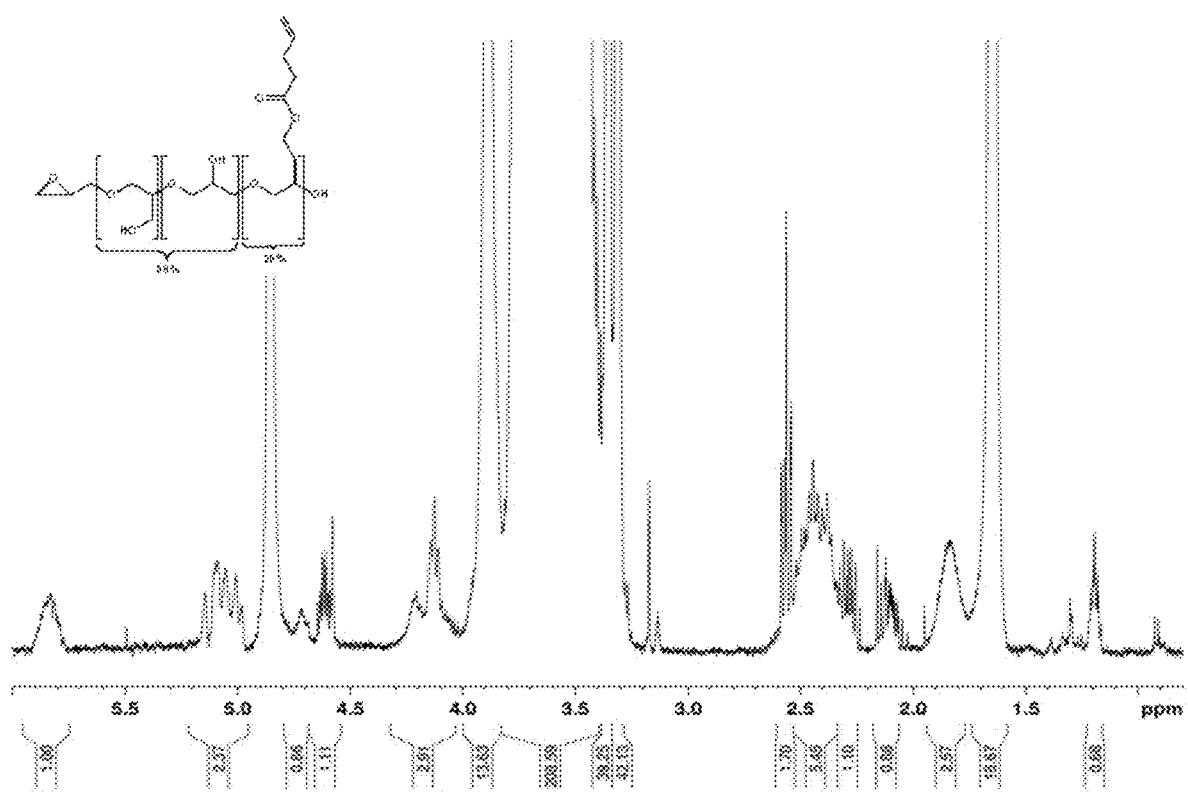
FIG. 15 shows NMR spectra for GLY/GEA polymer.

Unfortunately, the successful synthesis of the novel GEA monomer species was followed by the monomer's lackluster performance when copolymerized with glycidol. The drastic difference in polymerization kinetics, glycidol being very fast and GEA being rather slow, afforded a polymer product with truncated incorporation of the GEA monomer, appearing as a fifth of what was intended. This realization led to the realization that a kinetic study of the GEA homopolymer is needed so that the optimal reaction conditions for the new monomer can be discovered. The NMR of GLY/GEA polymer is shown in FIG. 15.

Synthesis of One-Pot Block Copolymer Structures

After determining that glycidol greatly outcompetes many lactone comonomers, it was proposed that a glycidol homopolymer capped with ester and allyl-containing units would be beneficial. In order to accomplish this, glycidol polymers were formed according to the determined polymerization restrictions and small amounts of α-allyl-δ-valerolactone (AVL) were added during the last hour of the polymerization, as the reaction was allowed to return to room temperature. This subsequent addition of the degradable lactone monomer was expected to add onto the end of the already formed poly(glycidol). The reaction scheme is shown below.

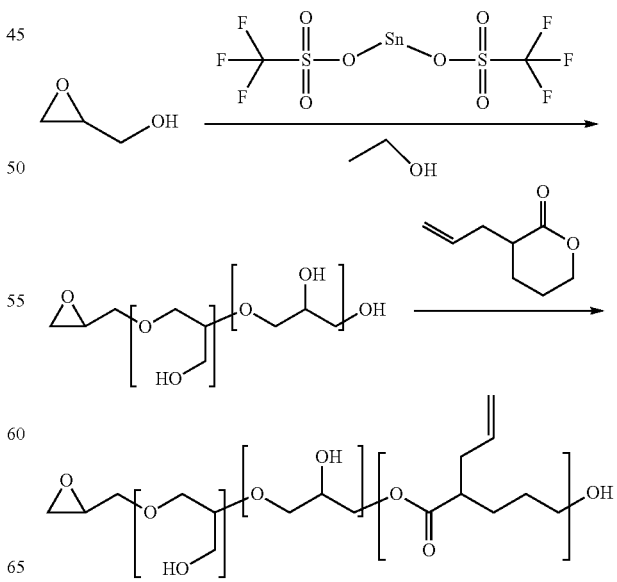

While $^1$HNMR does show the inclusion of ally groups to the polymer product, since glycidol is such a kinetically favored monomer, it cannot be determined if the product is actually a block copolymer or a random copolymer with a large glycidol "tail."

Regardless of the actual morphology of the polymer product, the incorporation of the allyl groups should allow for subsequent conjugation to free thiols on the exterior of biological structures such as proteins. It is believed that the attachment of these degradable hydrophilic polymers to proteins will increase the proteins' solubility and provide a system that is more advantageous for protein delivery than the PEGylated protein structures that are currently in use.

Synthesis of Linear Polyesters

Next, formation of linear polyester systems was investigated.[7-10] In one aspect, it was unknown whether tin triflate would yield polyester polymers similar to the ones obtained using the previously employed tin ethylhexanoate. In another aspect, tin triflate is more reactive than tin ethylhexanoate due to the large electron withdrawing character of its ligands. Therefore, in a further aspect, tin triflate is a preferential catalyst if it allows for the same control over polymer size and PDI as tin ethylhexanoate. First trials were performed using VL and AVL as copolymers according to the reaction scheme below.

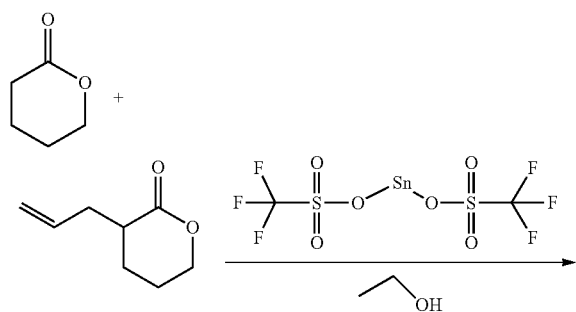

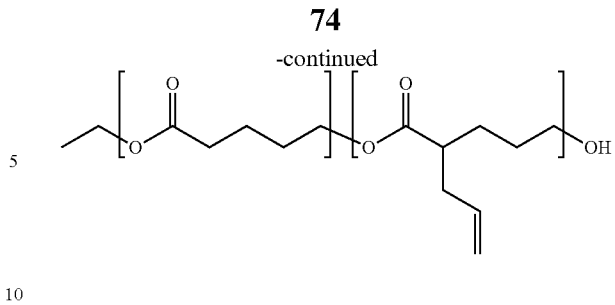

The produced linear polymers exhibited correct size and distribution with a faster reaction time and the ability to run the reaction at room temperature rather than elevated temperatures. Upon this positive outcome, further implementation of tin triflate was employed.

Figure 16:
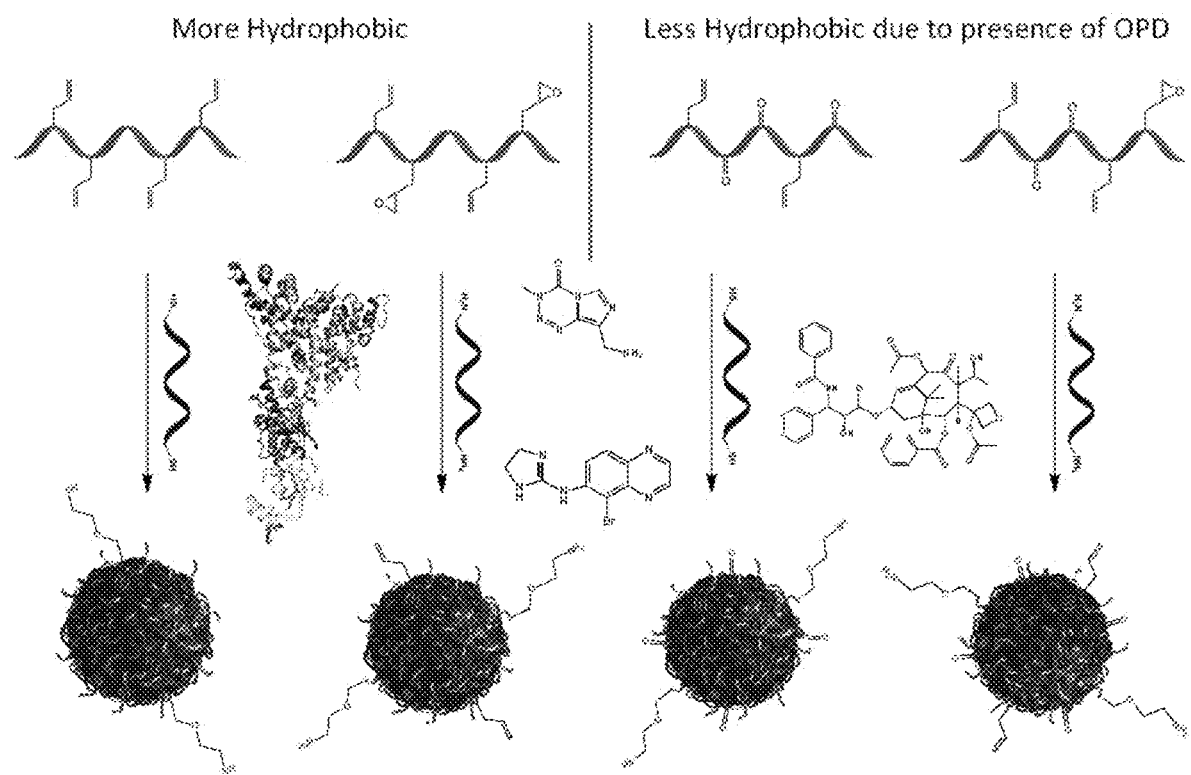
FIG. 16 shows a schematic representation of hydrophobicity of glycidol polymers due to the presence of OPD.

As depicted in FIG. 16, the addition of 2-oxepane-1,5-dione (OPD) to the backbone of the linear polyester systems imparts a higher degree of water solubility to the system.[7, 9, 10] Since this increased hydrophilicity is beneficial for the eventual use of the linear polyesters as the building blocks for nanoparticle drug delivery systems, a range of OPD containing VL/AVL polymers were evaluated to study its influence on the system.

The resulting polymer products contained OPD percentages ranging from 5%-40%. Furthermore, the purification of the polymer had to undergo a change. Rather than precipitating in methanol, as done with VL/AVL polymers, the new OPD containing polymers must be dialyzed against DCM as they do not precipitate in methanol. As expected, with the increase in OPD, there was an increase in the degree of water solubility. These new OPD polymers will be used for the formation of nanoparticles with increased hydrophilicity that will be employed as drug delivery vehicles. The exemplary reaction scheme below shows the synthesis of VL/AVL/OPD linear polymer according to the above method.

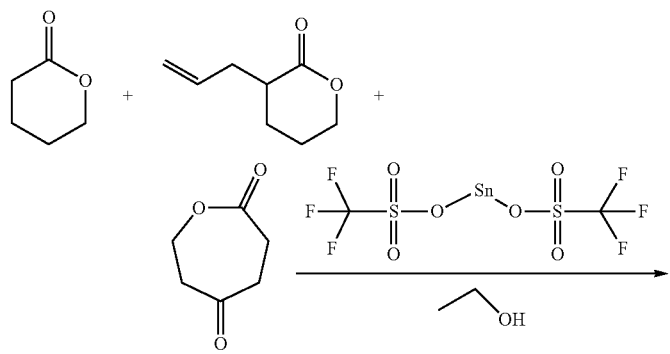

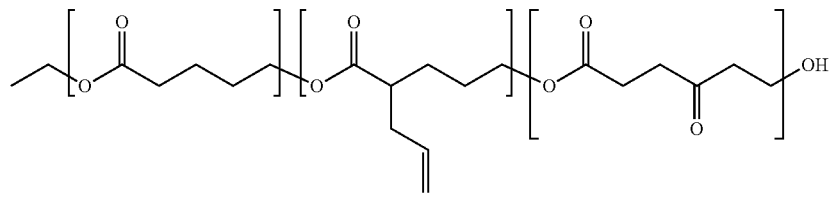

Synthesis of Novel Crosslinker Molecules for the Formation of Nanoparticles

As described herein, the present invention, in one aspect, also involves novel cross-linking molecules. In a further aspect, the cross-linking molecules have the ability to be protonated. In another aspect, the present invention also relates to the delivery of biological structures with the nanoparticles using the cross-linking molecules. In a further aspect, the protonation capacity is important since biological structures, such as siRNA will be held more tightly by the positive charges than they would be if the cross-linking of the polymers was the only method being employed to contain the biological structures in the nanoparticles. In a still further aspect, the efficacy of this approach has recently been illuminated in dendritic polyglycerol species.[37]

Figure 17:
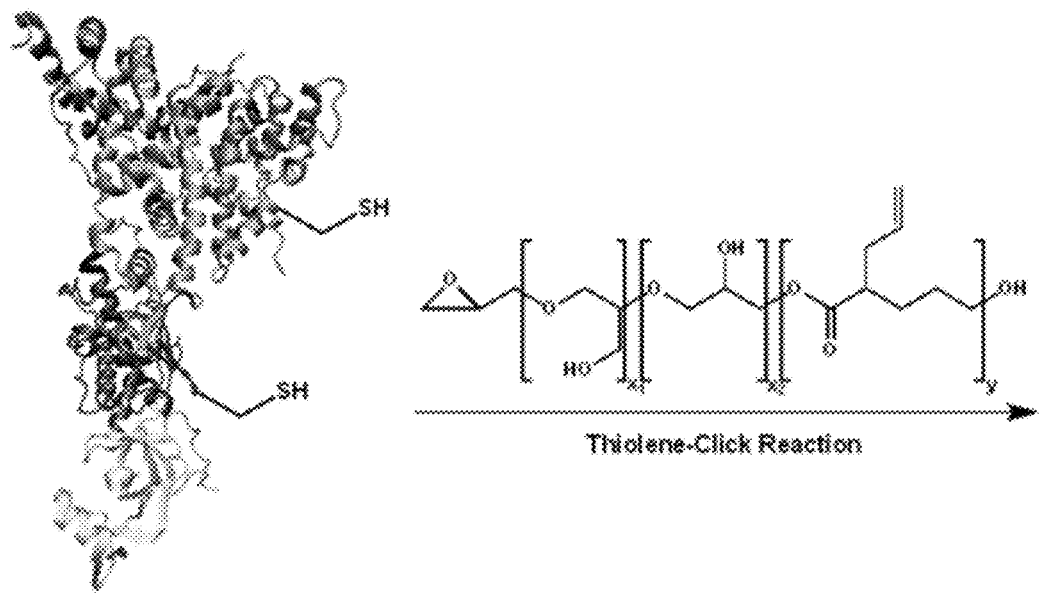
FIG. 17 shows a schematic representation of a siRNA complexation reaction.
Figure 18:
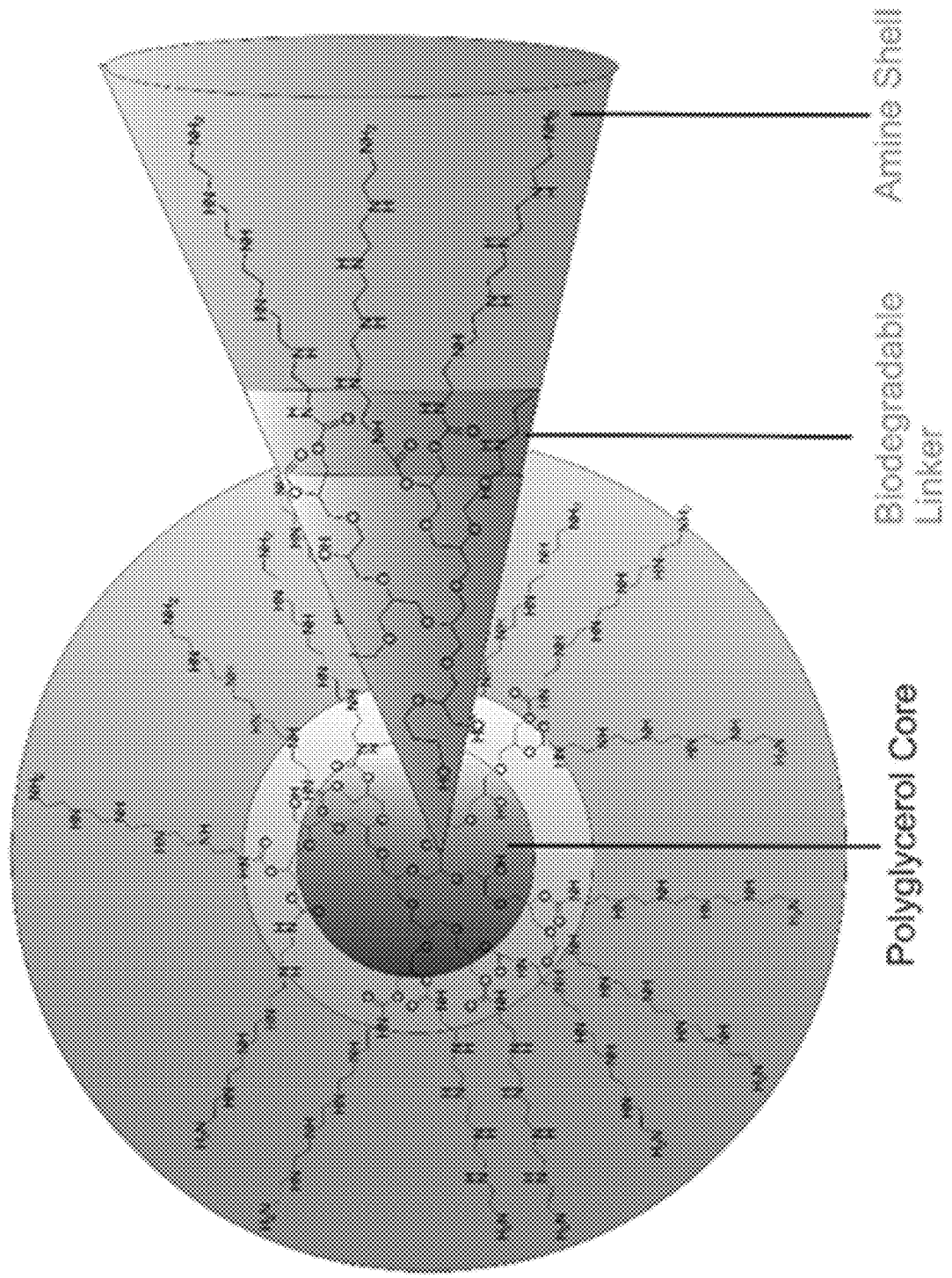
FIG. 18 shows a schematic representation of a dendritic polyglycerols with an amine shell.

In a first example, a protected dithiol species was employed. The disulfide was attached to a carboxylic acid and subsequently reacted with 0.5 equivalents of a diamine species, affording a molecule with secondary amine species and readily accessible thiol groups. The thiol groups were used for "click" reactions[8] in order to form nanoparticles (FIG. 17), while the secondary amines were used to increase the complexation of siRNA into the system (FIG. 18). [37, 40] The exemplary reaction scheme below shows the formation of a nanoparticle in accordance with the above method.

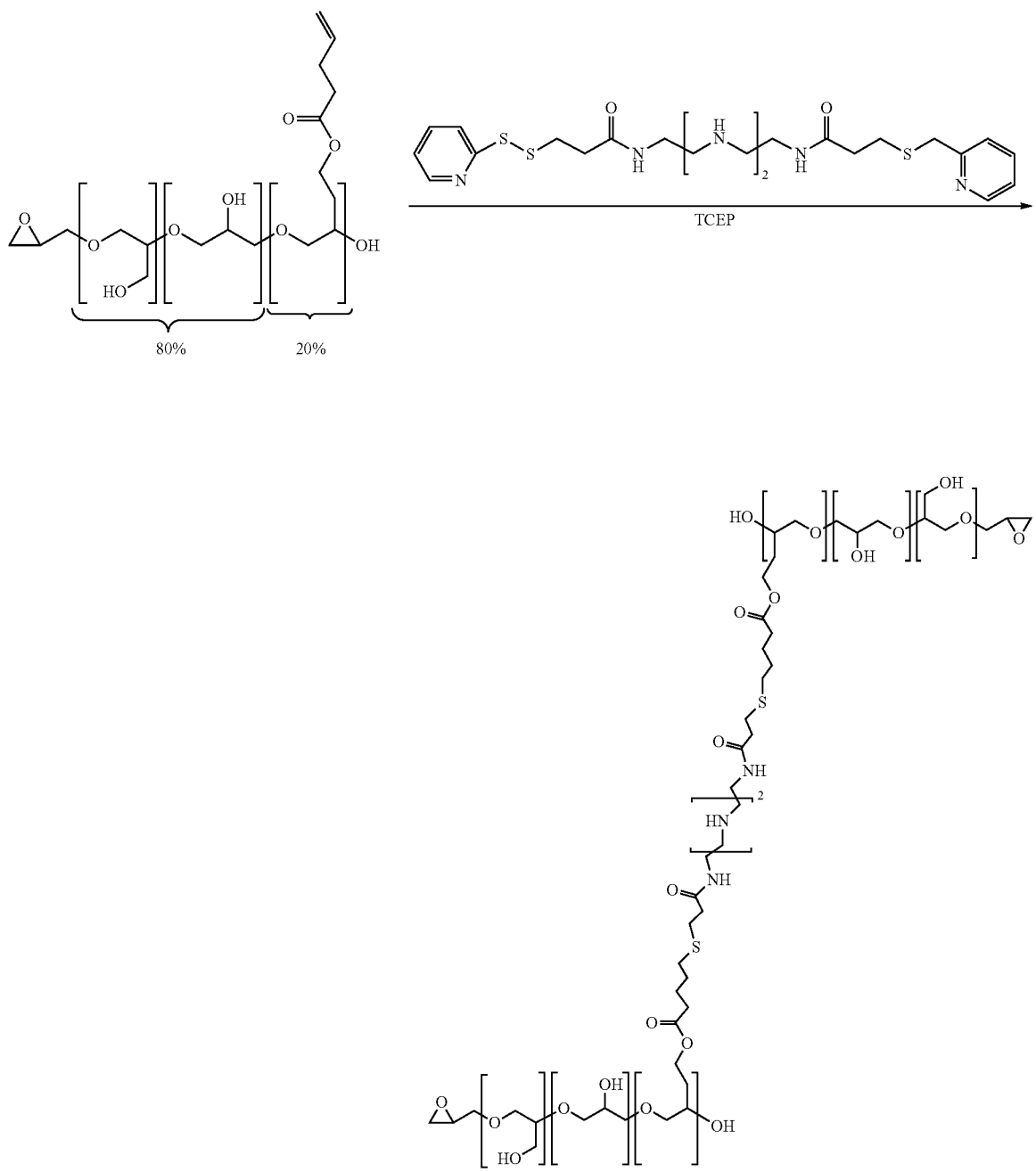

Figure 19:
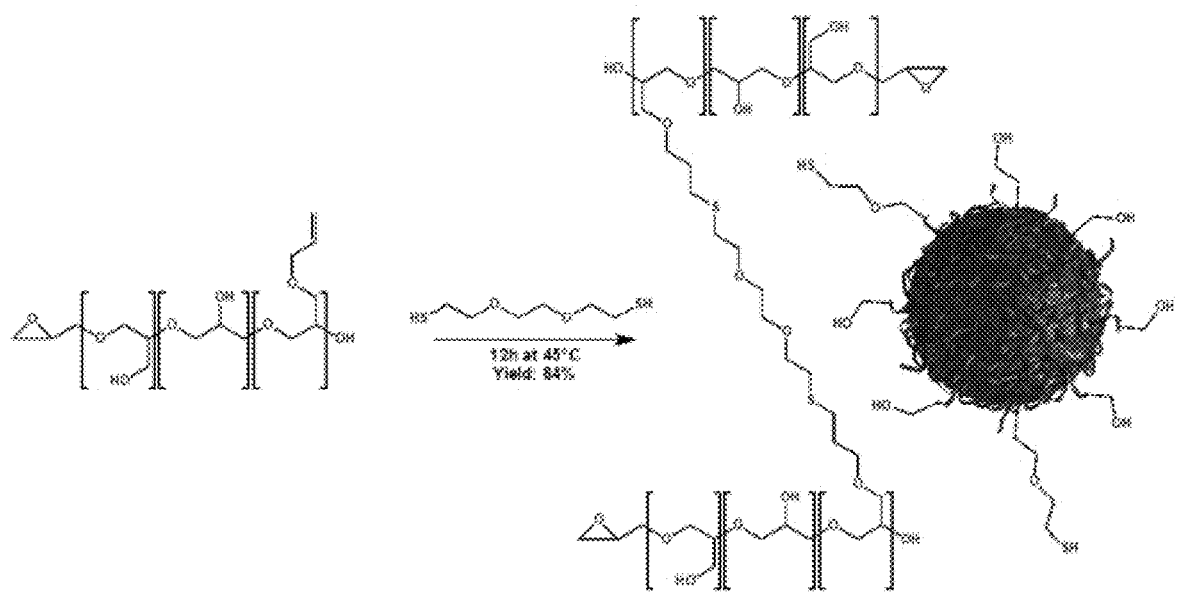
FIG. 19 shows a schematic representation of nanoparticle formation through a controlled thiolene-click reaction of the present invention.
Figure 20:
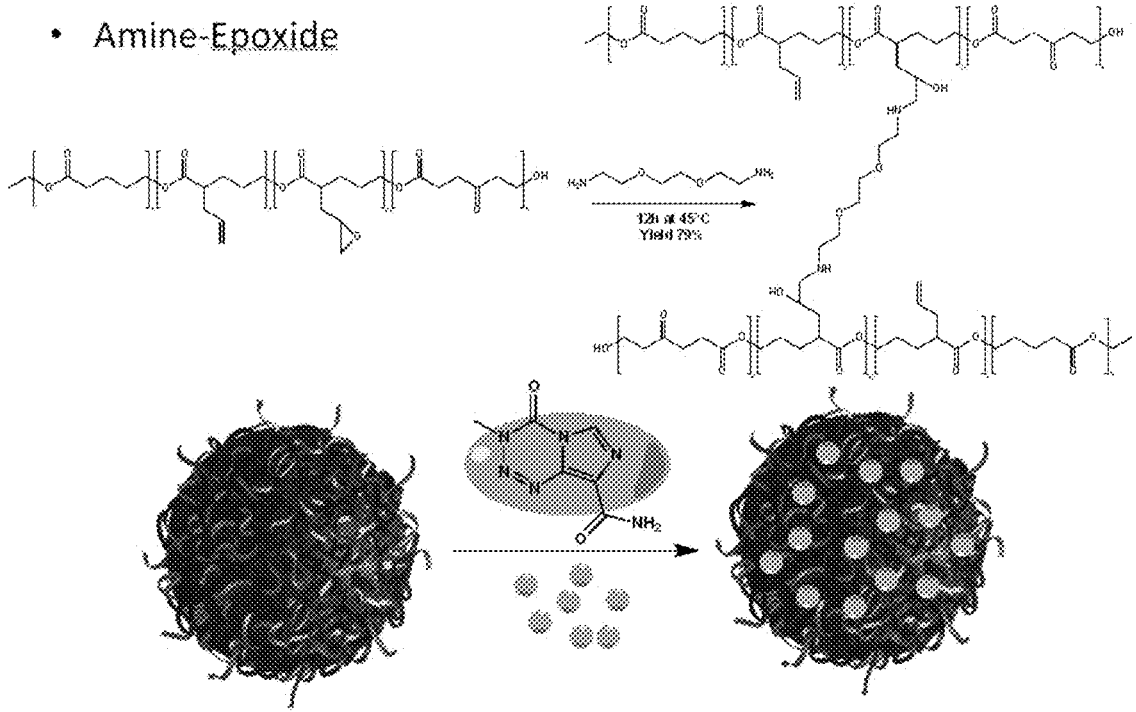
FIG. 20 shows a schematic representation of formation of polyester nanoparticles.
Figure 21:
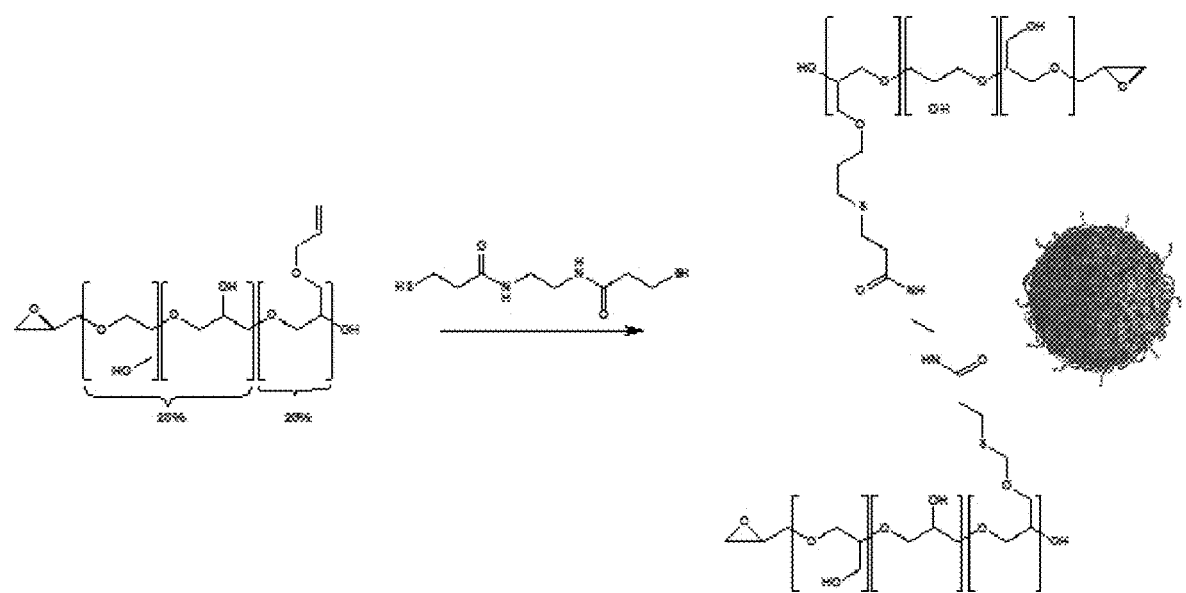
FIG. 21 shows a schematic representation of thiolene-click GLY/AGE nanoparticle formation of the present invention.

The final step in the formation of the nanoparticle drug delivery system is the collapsing of the polymers into nanoparticles. In one aspect, this reaction was conducted by two separate methods. In a further aspect, the methods include thiolene-click reactions[8](FIG. 19) and amine-epoxide reactions[7, 10](FIG. 20). In still further aspect, the two methods can also be employed in the formation of polyester nanoparticles as well as the synthesis of novel polyglycerol structures. The exemplary reaction scheme in FIG. 21 shows thiolene-click GLY/AGE nanoparticle formation.

Figure 22:
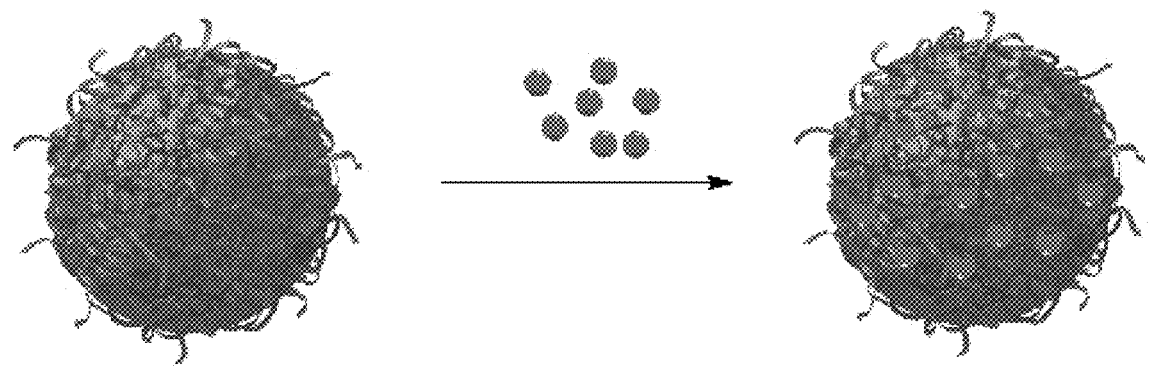
FIG. 22 shows a schematic representation of loading of nanoparticle with small molecule drugs.

Next, to evaluate the viability of the nanoparticle systems, drug loading and release studies were performed. As depicted in FIG. 22, a number of small molecule drugs including Paclitaxel, Bromonidine, and Temozolomide, were chosen to be loaded into the polyester nanoparticles. The percentage of drug incorporation was determined using a nano-drop method based on UV/VIS absorption. The drug release profiles of these systems was studied by dissolving the loaded nanoparticles in a physiological pH buffer and allowing the solution to stir at 37° C. The buffer was changed every 48 hours and the excreted drug was extracted using DCM and quantified using nanoDrop. Similar techniques will be employed in order to study the drug loading and release capabilities of the newly synthesized poly(glycidol) based systems.

Dual Component Delivery System

In various aspects, the present invention also relates to a two component delivery system. In a further aspect, the dual component drug delivery system can deliver 2 classes of therapeutics. For example, in one aspect, a dual component drug delivery system can help achieve bone union following fracture in patients with neurofibromatosis (NF1). These patients cannot heal their bone and require amputation. In a further aspect, mouse models can recapitulate this skeletal complication. Thus, in a still further aspect, in this example the objective was to combine small molecules, such as MEK inhibitors, and BMP2 growth factors to promote bone union (FIG. 27).

In another aspect, the present invention provides a reconfigurable and responsive network system (FIG. 28). In a further aspect, the network systems comprise functionalized polyglycidol-based crosslinking materials for hydrogels with functionalized polyesters or polycarbonates. In a still further aspect, the network systems can comprise functionalized polyglycidols crosslinked with functionalized degradable materials such as linear polyesters and polycarbonates. In one aspect, the networks can be reconfigured and are not thermosets, but rather act as vitrimers.

Figure 29:
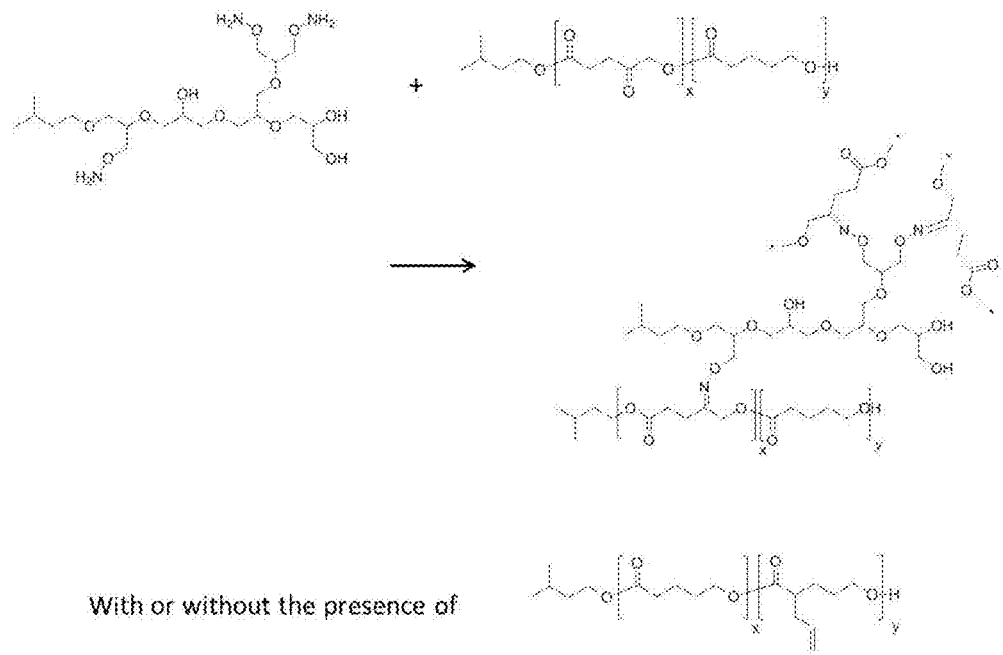
FIG. 29 shows a schematic representation of exemplary reaction schemes for formation of network systems of the present invention.
Figure 29:
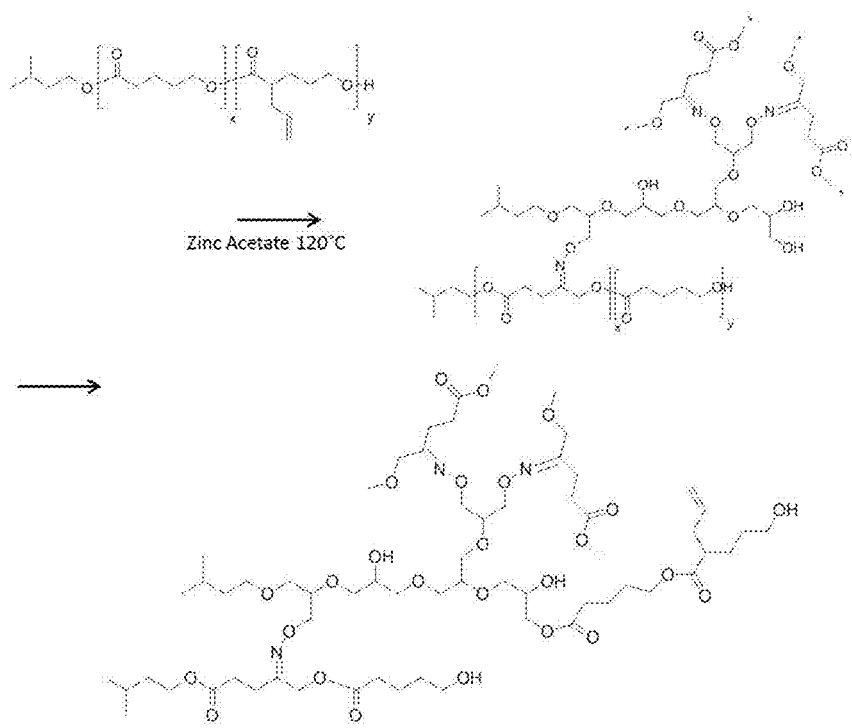

These networks are are not "set" in the presence of the $Zn(Ac)_2$, and the free —OH groups of the polyclidol can react with available esters, making the polymers therefore stimuli responsive. In an even further aspect, the networks systems are reconfigurable and are not set. Exemplary reactions for forming functionalized polyglycidols in a network system are shown in FIG. 29.

I. Experimental Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diasteromeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

All reagent chemicals were purchased from Sigma-Aldrich, Strem Chemicals, or Acros and used as received unless otherwise noted. The m-CPBA (77%) was purified as previously reported in the literature while δ-valerolactone and glycidol was further purified through vacuum distillation. SnakeSkin® Pleated Dialysis Tubing, regenerated cellulose, was purchased from Pierce Biotechnology. Spectra/Por® Dialysis membrane was purchased from Spectrum Laboratories Inc. α-allyl-δ-valerolactone, α-propargyl-δ-valerolactone, and 2-oxepane-1,5-dione were synthesized as previously reported in the literature.

$^1$H and $^3$C NMR were obtained from a Bruker AV-1 400 MHz, a Bruker DRX 500 MHz, or a Bruker AV-II 600 MHz spectrometer. The reported chemical shifts are in ppm and are in reference to the corresponding residual nuclei in deuterated solvents.

Gel-permeation chromatography (GPC) was carried out with a Waters chromatograph system equipped with a Waters 2414 refractive index detector, a Waters 2481 dual λ absorbance detector, a Waters 1525 binary HPLC pump, and four 5 mm Waters columns (300 mm×7.7 mm), connected in series with increasing pore size (100, 1000, 100,000 and 1,000,000 Å respectively). All runs were performed with N—N-dimethylformamide (DMF) as the eluent at a flow rate of 1 mL/min.

Samples for transmission electron microscopy (TEM) imaging were prepared by dissolving 0.5 mg nanoparticles in 1 mL isopropanol, 0.3 mL acetonitrile and 0.2 mL toluene. The samples were sonicated for 5 min and were stained with 3 drops of 3% phosphotungstic acid. The carbon grids were prepared by slowly dipping an Ultrathin Carbon Type-A 400 Mesh Copper Grid (Ted Pella, Inc., Redding, Calif.) into the particle solutions three times and drying the grid at ambient temperature. A Philips CM20T transmission electron microscope operating at 200 kV in bright-field mode was used to obtain TEM micrographs of the polymeric nanoparticles.

Figure 23:
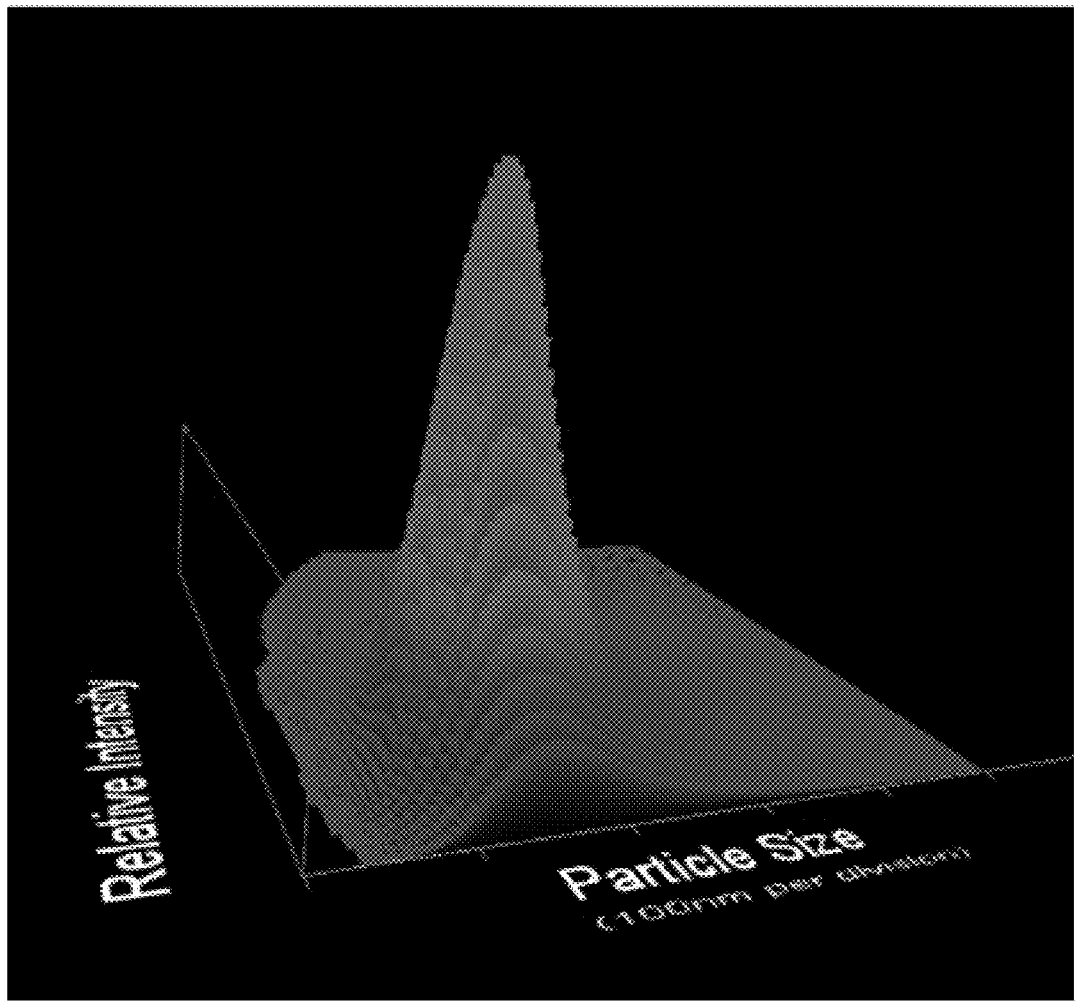
FIG. 23 shows a visual representation of the minimal size dispersity of nanoparticle structures of the present invention.

FIG. 23 shows the DLS (Nanosight instrument), depicting the minimal size dispersity of nanoparticle structures (115 nm).

2. Preparation of Glycidol Polymers a. General Procedure

A 25 mL and a 10 mL round bottom flask were flame-dried under $N_2(g)$, along with a 50 mL 3-neck round bottom flask equipped with a stir bar. In the 25 mL round bottom flask, an 1.7M Iso-Amyl alcohol (IAOH) stock solution was formed using dry THF, while the 10 mL round bottom flask was used to create a $3.7 \times 10^{-2}$M tin triflate stock solution, also using dry THF. The stock solutions were then allowed to sit for 30 minutes before adding $Sn(OTf)_2$ (0.00035 eq) and IOAH (0.066 eq) to the reaction flask. The reaction flask was then brought to the proper reaction temperature before adding the monomers (1.0 and allowing the polymerization to run to completion. Figures are shown using an ethanol initiator (EtOH) instead of the IAOH. The use is optional but the IAOH is preferred because the polymer products can be more accurately characterized. The protons from IAOH do not overlap with polymer peaks and the polymer molecular weight can be determined via $^1$H-NMR.

Preparation of GLY Homopolymer

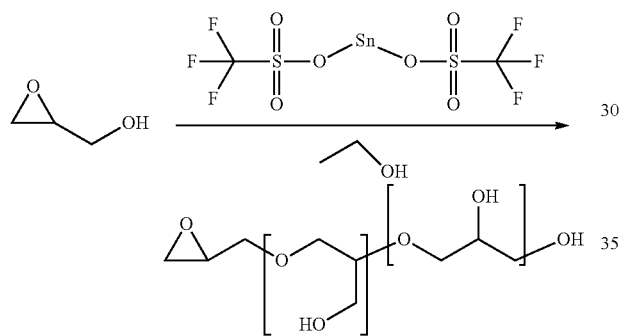

$Sn(OTf)_2$ (0.26 mL; $9.45 \times 10^{-6}$ mol; 0.00035 eq) and IAOH (0.20 mL; $3.33 \times 10^{-4}$ mol; 0.066 eq) were added to the reaction flask, which was then lowered into an acetone/dry ice bath at $-42°$ C. The flask was allowed to cool completely before adding the glycidol (2.00 g; 27.00 mmol; 1.0 eq) monomer. The reaction was then allowed to run for 8 h while maintaining the depressed temperature. After 8 h the resulting viscous polymer product was precipitated into vigorously stirring hexanes affording a clear viscous product. The hexanes were decanted from the product, which was then transferred to a 6-dram vial, using methanol. Yield: 1.896 g (94.82%). $^1$H-NMR (600 MHz, CDCl$_3$) δ: 3.31-3.94 (6H). $^{13}$C-NMR (150 MHz, CDCl$_3$) δ: 81.37, 79.81, 75.12, 73.88, 72.01-72.94, 70.42-71.17, 64.41, 62.53, 62.06.

(1) Preparation of GLY/AGE Polymer (80/20)

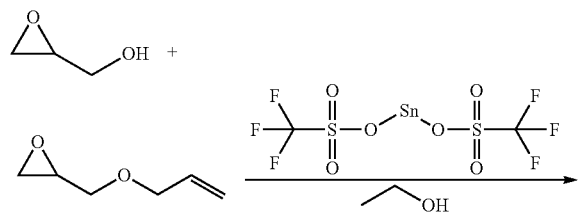

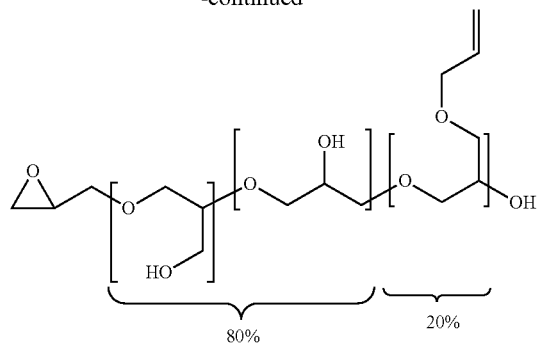

$Sn(OTf)_2$ (0.23 mL; $8.52 \times 10^{-6}$ mol; 0.00035 eq) and EtOH (0.196 mL; $3.33 \times 10^{-4}$ mol; 0.066 eq) were added to the reaction flask, which was then lowered into an acetonitrile/dry ice bath at $-42°$ C. The flask was allowed to cool completely before adding the glycidol (1.44 g; 19.47 mmol; 4.0 eq) and glycidyl ether (0.56 g; 4.87 mmol; 1.0 eq). The reaction was then allowed to run for 8 h while maintaining the depressed temperature. After 8 h the resulting viscous polymer product was precipitated into vigorously stirring hexanes affording a clear viscous product. The hexanes were decanted from the product, which was then transferred to a 6-dram vial, using methanol. Yield: 2.05 g (68.27%). $^1$H-NMR (600 MHz, CDCl$_3$) δ: 5.92 (1H), 5.21 (2H), 4.04 (2H), 3.38-3.94 (27.30H). $^{13}$C-NMR (150 MHz, CDCl$_3$) δ: 136.31, 117.42, 81.56, 80.01, 74.09, 73.43, 72.51, 70.87, 64.60, 62.69.

(2) Preparation of GEA Homopolymer

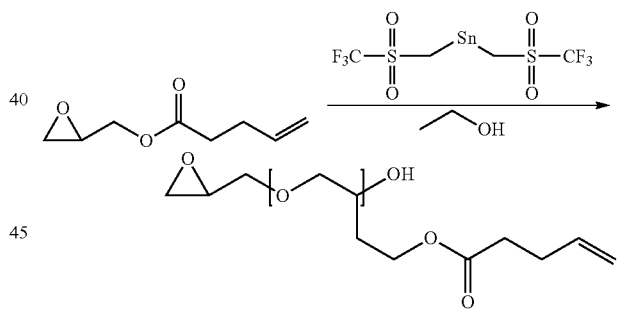

$Sn(OTf)_2$ (0.056 mL; $2.06 \times 10^{-6}$ mol; 0.00035 eq) and IAOH (0.098 mL; $1.67 \times 10^{-4}$ mol; 0.066 eq) were added to the reaction flask, which was then lowered into an acetonitrile/dry ice bath at $-42°$ C. The flask was allowed to cool completely before adding the previously synthesized glycidyl ester allyl (1.0 g; 5.88 mmol; 1.0 eq). The reaction was then allowed to run for 8 h while maintaining the depressed temperature. After 8 h the resulting viscous polymer product was precipitated into vigorously stirring hexanes affording a clear viscous product. The hexanes were decanted from the product, which was then transferred to a 6-dram vial, using methanol. Yield: 230.8 mg (23.08%). $^1$H-NMR (600 MHz, CDCl$_3$) δ: 5.83 (1H), 5.00 (2H) 4.61 (5H), 3.39-3.82 (19.06H), 2.24-2.66 (23.33H) 2.12 (6.17H) 1.56-1.92 (4.87H). $^{13}$C-NMR (150 MHz, CDCl$_3$): 180.40, 174.87, 138.14, 136.53, 135.64, 117.62, 115.98, 81.31, 79.58, 70.84, 67.32, 66.52, 64.62, 60.05, 37.16, 34.39, 31.13, 29.55, 24.51.

(3) Preparation of GLY/GEA Polymer (80/20)

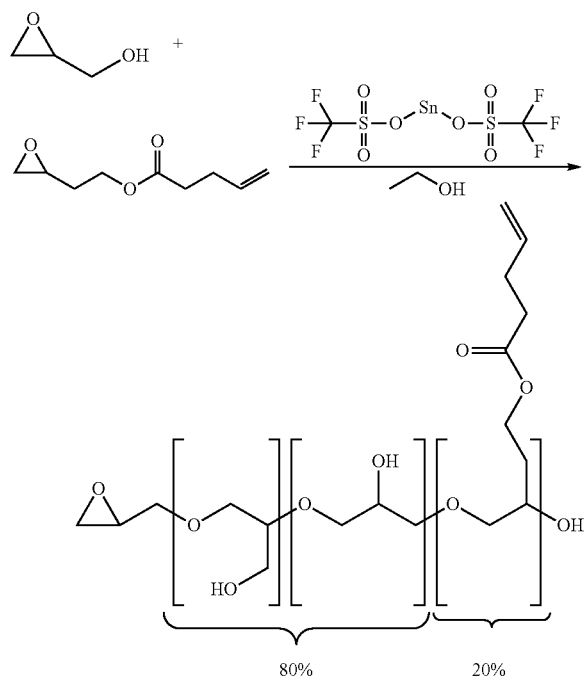

Sn(OTf)$_2$ (0.10 g; 3.75×10$^{-6}$ mol; 0.00035 eq) and EtOH (0.10 mL; 1.67×10$^{-4}$ mol; 0.066 eq) were added to the reaction flask, which was then lowered into an acetonitrile/dry ice bath at −42° C. The flask was allowed to cool completely before adding the glycidol (0.64 g; 8.57 mmol; 4.0 eq) and the previously synthesized glycidyl ester allyl (0.36 g; 2.14 mmol; 1.0 eq). The reaction was then allowed to run for 8 h while maintaining the depressed temperature. After 8 h the resulting viscous polymer product was precipitated into vigorously stirring hexanes affording a clear viscous product. The hexanes were decanted from the product, which was then transferred to a 6-dram vial, using methanol. Yield: 633.7 mg (63.37%). $^1$H-NMR (600 MHz, CDCl$_3$) δ: 5.93 (1H), 5.27 (2.37H), 4.06-4.28 (2.91H) 3.26-3.98 (303.6H), 2.24-2.63 (8.25H), 1.84 (2.57H), 1.65 (18.67H). $^{13}$C-NMR (150 MHz, CDCl$_3$) δ: 138.53, 72.90, 71.32, 63.42, 61.52, 26.55.

(4) Preparation of GLY/MLGEA Polymer (80/20)

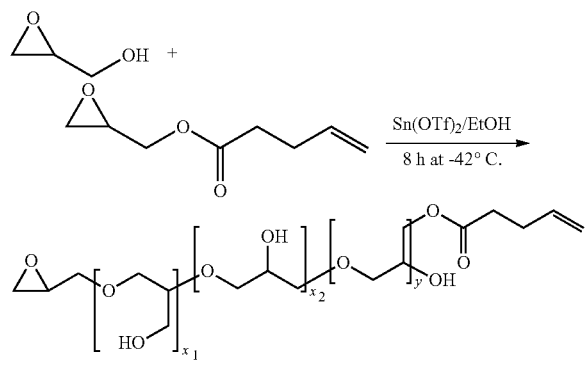

Sn(OTf)$_2$ (0.10 g; 3.75×10$^{-6}$ mol; 0.00035 eq) and EtOH (0.10 mL; 1.67×10$^{-4}$ mol; 0.066 eq) were added to the reaction flask, which was then lowered into an acetonitrile/dry ice bath at −42° C. The flask was allowed to cool completely before adding the glycidol (0.64 g; 8.84 mmol; 4.0 eq) and the previously synthesized mixed-length glycidyl ester allyl (0.35 g; 2.21 mmol; 1.0 eq). The reaction was then allowed to run for 8 h while maintaining the depressed temperature. After 8 h the resulting viscous polymer product was precipitated into vigorously stirring hexanes affording a clear viscous product. The hexanes were decanted from the product, which was then transferred to a 6-dram vial, using methanol. $^1$H-NMR (600 MHz, CDCl$_3$) δ: 5.83 (1H), 5.07 (2.37H), 3.97-4.21 (1.74H) 3.29-3.95 (97.12H), 2.26-2.61 (4.95H), 1.82 (1.61H), 1.65 (7.54H).

(5) Preparation of EEGE Homopolymer

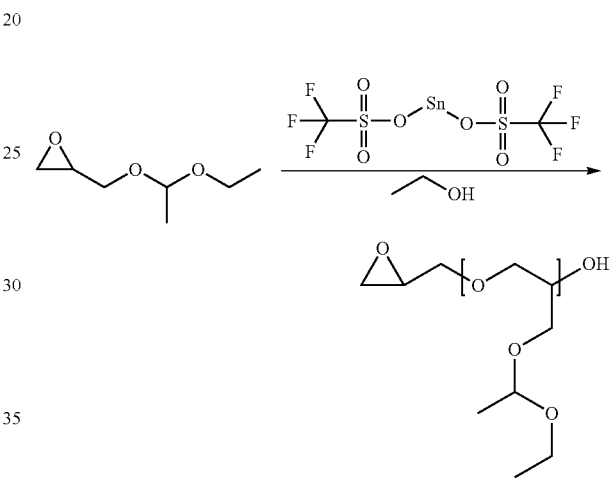

Sn(OTf)$_2$ (0.032 mL; 1.20×10$^{-6}$ mmol; 0.00035 eq) and EtOH (0.049 mL; 8.33×10$^{-5}$ mmol; 0.066 eq) were added to the reaction flask. The synthesized ethoxyethyl glycidyl ether (0.5 g; 3.42 mmol; 1.0 eq) was then added. The reaction was then allowed to run for 24 h at room temperature. After 24 h the resulting viscous polymer product was precipitated into vigorously stirring hexanes affording a whitish viscous product. Yield: 196.5 mg (39.3%). The hexanes were decanted from the product, which was then transferred to a 6-dram vial, using methanol. $^1$H-NMR (500 MHz, CDCl$_3$) δ: 4.16 (1H), 3.87 (1.21H), 3.39-3.81 (19.28H), 1.64 (5.54H), 1.23 (8.08H), 0.86 (2.92H).

(6) Preparation of EEGE/GEA Polymer (80/20)

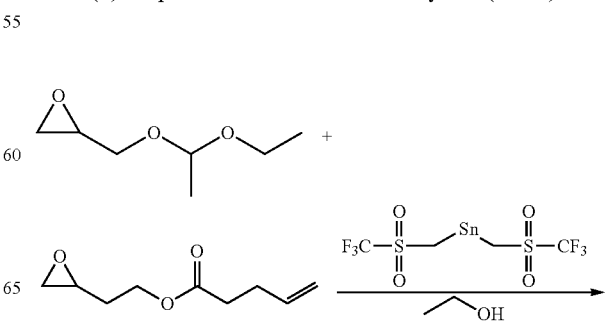

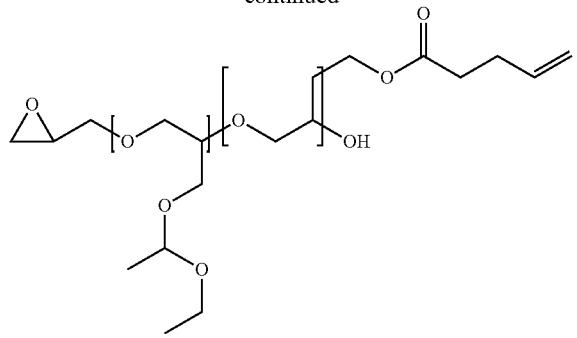

Sn(OTf)$_2$ (0.0313 mL; 1.16×10$^{-6}$ mmol; 0.00035 eq) and EtOH (0.049 mL; 8.33×10$^{-5}$ mmol; 0.066 eq) were added to the reaction flask. The stock solutions were allowed to stir for 10 minutes before adding the δ-valerolactone (1.48 g; 14.80 mmol; 4.0 eq) and α-allyl-δ-valerolactone (0.52 g; 3.70 mmol; 1.0 eq). The reaction was then allowed to run for 24 h at room temperature. After 24 h the resulting viscous polymer product was precipitated into cold diethyl ether to afford the off-white particulate polymer product. The diethyl ether was decanted from the product, which was then transferred to a 6-dram vial, using ethyl acetate. Yield: 374.9 mg (74.98%). $^1$H-NMR (500 MHz, CDCl$_3$) δ: 4.28 (1H), 3.43-3.78 (6.43H), 3.17 (1.32H), 2.35 (3.36H), 2.02 (2.84H), 1.65 (10.42H), 1.29 (69.79H), 0.92 (37.31H).

(7) Preparation of EEGE/MLGEA Polymer (80/20)

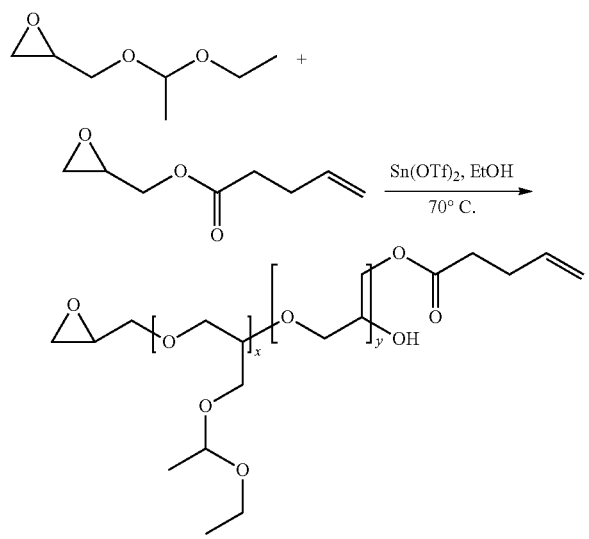

Sn(OTf)$_2$ (0.0313 mL; 1.16×10$^{-6}$ mmol; 0.00035 eq) and EtOH (0.049 mL; 8.33×10$^{-5}$ mmol; 0.066 eq) were added to the reaction flask. The stock solutions were allowed to stir for 30 minutes before adding the EEGE (1.36 g; 14.54 mmol; 4.0 eq) and MLGEA (0.47 g; 3.36 mmol; 1.0 eq). The reaction was then allowed to run for 24 h at 70° C. After 24 h the resulting viscous polymer product was precipitated into methanol to afford the off-white particulate polymer product. The methanol was decanted from the product, which was then transferred to a 6-dram vial, using ethyl acetate.

(8) Preparation of GLY/VL Polymer (80/20)

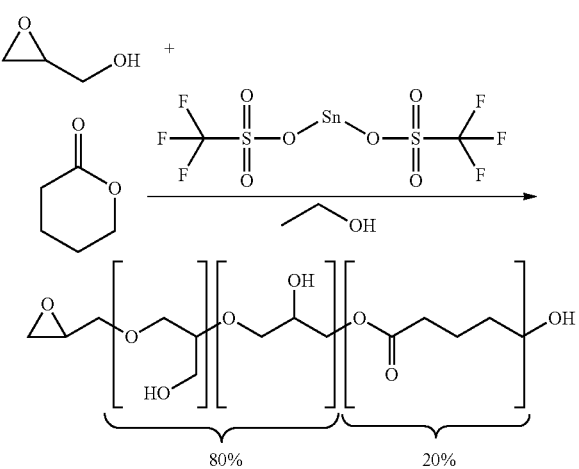

Sn(OTf)$_2$ (024 mL; 8.82×10$^{-6}$ mmol; 0.00035 eq) and EtOH (0.20 mL; 3.33×10$^{-4}$ mmol; 0.066 eq) were added to the reaction flask, which was then lowered into a salt water/ice bath at −20° C. The flask was allowed to cool completely before adding the glycidol (1.49 g; 20.16 mmol; 4.0 eq) and δ-valerolactone (0.50 g; 5.04 mmol; 1.0 eq). The reaction was then allowed to run for 8 h while maintaining the depressed temperature. After 8 h the resulting viscous polymer product was precipitated into vigorously stirring hexanes affording a whitish viscous product. The hexanes were decanted from the product, which was then transferred to a 6-dram vial, using methanol. Yield: 1.54 g (77%). $^1$H-NMR (600 MHz, CDCl$_3$) δ: 4.10 (1H), 3.89 (1.17H), 3.41-3.82 (18.48H), 3.33 (7.66H), 2.37 (1.36H, 1.51-1.76 (4.29H). $^{13}$C-NMR (150 MHz, CDCl$_3$) δ: 138.52, 72.96, 71.38, 69.70, 64.07, 33.50, 28.15, 21.59.

(9) Preparation of GLY/VL/AVL Polymer (60/20/20)

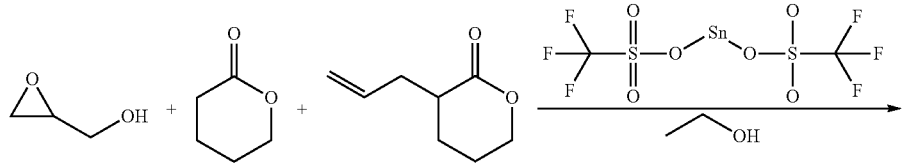

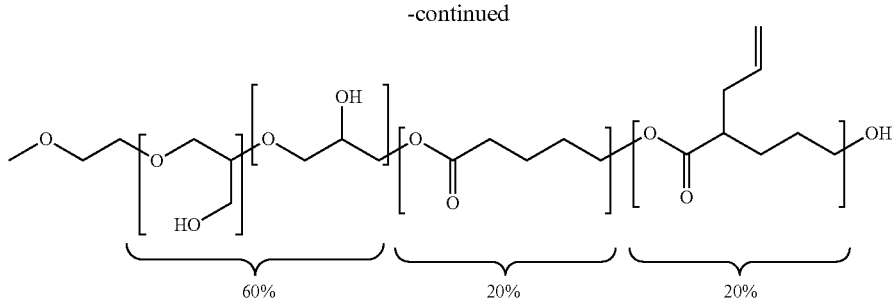

Sn(OTf)$_2$ (0.20 mL; 7.56×10$^{-6}$ mmol; 0.00035 eq) and EtOH (0.20 mL; 3.33×10$^{-4}$ mmol; 0.066 eq) were added to the reaction flask, which was then lowered into a salt water/ice bath at −20° C. The flask was allowed to cool completely before adding the glycidol (0.96 g; 12.96 mmol; 3.0 eq), δ-valerolactone (0.61 g; 4.32 mmol; 1.0 eq), and α-allyl-δ-valerolactone (0.43 g; 4.32 mmol; 1.0 eq). The reaction was then allowed to run for 8 h while maintaining the depressed temperature. After 8 h the resulting viscous polymer product was precipitated into vigorously stirring hexanes affording a whitish viscous product. The hexanes were decanted from the product, which was then transferred to a 6-dram vial, using methanol. Yield: 528.4 mg (35.23%). $^1$H-NMR (600 MHz, CDCl$_3$) δ: 5.77 (1H), 5.05 (2H), 4.13 (7.46H), 3.29-4.03 (171.73H), 2.38 (14.37H), 1.66 (34.73H), 1.22 (7.25H). $^{13}$C-NMR (150 MHz, CDCl$_3$) δ: 175.82, 136.74, 117.21, 83.16, 81.40, 79.83, 73.85, 72.25, 64.44, 62.45, 37.65, 34.53, 32.94, 31.29, 30.04, 29.24, 27.44, 22.46, 15.49, 14.63.

(10) Preparation of GLY/VL/PO/AGE Polymer (50/20/20/10)

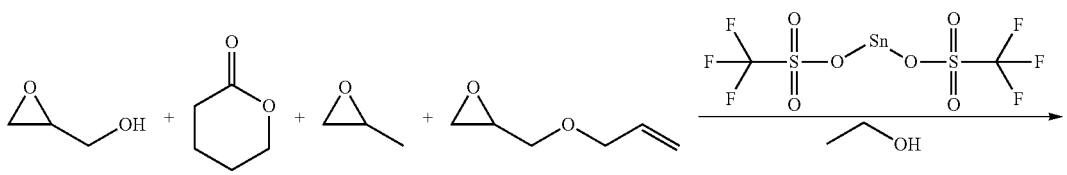

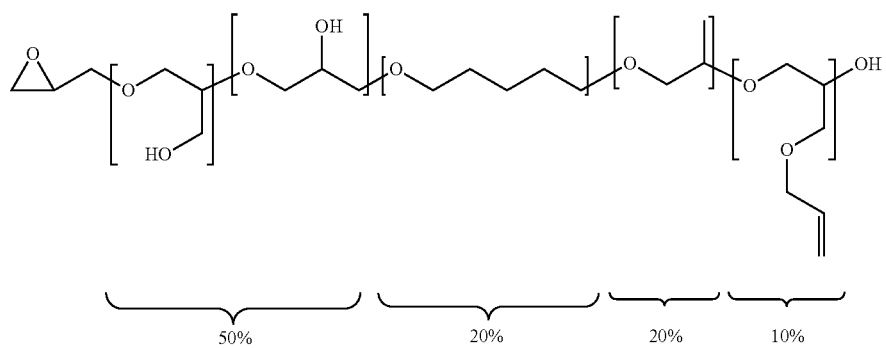

Sn(OTf)$_2$ (5.83 mg; 1.28×10$^{-5}$ mol; 0.00035 eq) and EtOH (0.012 mL; 2.07×10$^{-4}$ mol; 0.066 eq) were added to the reaction flask, which was then lowered into a salt water/ice bath at −20° C. The flask was allowed to cool completely before adding the glycidol (0.47 g; 6.38 mmol; 5.0 eq), δ-valerolactone (0.26 g; 2.56 mmol; 2.0 eq), propylene oxide (0.15 g; 2.56 mmol; 2.0 eq), and allyl glycidyl ether (0.15 g; 1.28 mmol; 1.0 eq). The reaction was then allowed to run for 8 h while maintaining the depressed temperature. After 8 h the resulting viscous polymer product was precipitated into vigorously stirring hexanes affording a whitish viscous product. The hexanes were decanted from the product, which was then transferred to a 6-dram vial, using methanol. Yield: 218.2 mg (21.82%). $^1$H-NMR (600 MHz, CDCl$_3$) δ: 5.92 (1H), 5.22 (2.05H), 4.03 (2.36H), 3.29-3.96 (54.76H), 2.16 (1.09H), 1.68 (1.81H), 1.30 (3.74H), 1.15 (10.64H). $^{13}$C-NMR (150 MHz, CDCl$_3$) δ: 207.26, 176.02, 136.26, 117.50, 7.70, 74.01, 73.39, 72.28, 70.73, 62.51, 52.22, 34.59, 33.02, 22.53.

(11) Oxidation of GLY/AGE Polymer (80/20)

To a round bottom flask equipped with a stir bar, was added the GLY/AGE polymer (1.0 eq), m-CPBA (0.1 eq), and methanol (5.4×10$^{-2}$ g/mL). The round bottom flask was then capped with a septum and allowed to stir for 72 h at room temperature. The resulting product solution was then concentrated and precipitated into vigorously stirring hexanes. The hexane was decanted from the product, which was then transferred to a 6-dram vial using methanol. Yield: 128.2 mg (24.97%). $^1$H-NMR (600 MHz, CDCl$_3$) δ: 5.93 (1H), 5.26 (2.01H), 4.03 (1.96H), 3.89 (4.00H), 3.38-3.81 (53.76H), 3.31 (1.07H), 1.65 (5.33H). $^{13}$C-NMR (150 MHz, CDCl$_3$) δ: 136.26, 117.40, 81.47, 79.92, 79.27, 74.02, 72.41, 70.72, 64.54, 62.63, 27.73.

3. Preparation of Monomers (1) Purification of m-CPBA m-CPBA (70 g; 77%) was dissolved in diethyl ether (500 mL) and transferred to a separatory funnel. The ether layer was then washed 3× with 300 mL aliquots of buffer solution (410 mL 0.1M NaOH, 250 mL 0.2M KH$_2$PO$_4$, made up to 1 L; pH≈7.5). The ether layer was dried over MgSO$_4$ and

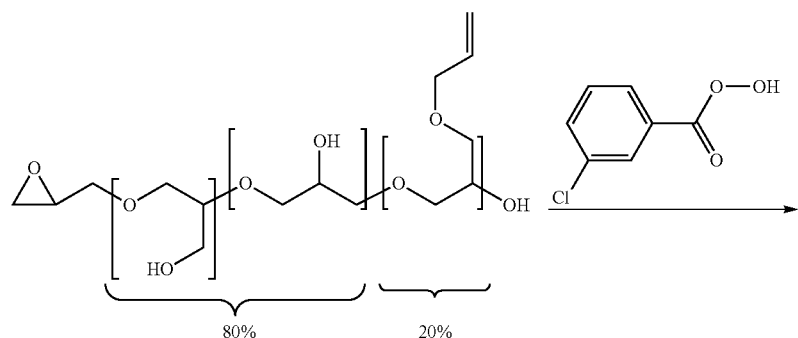

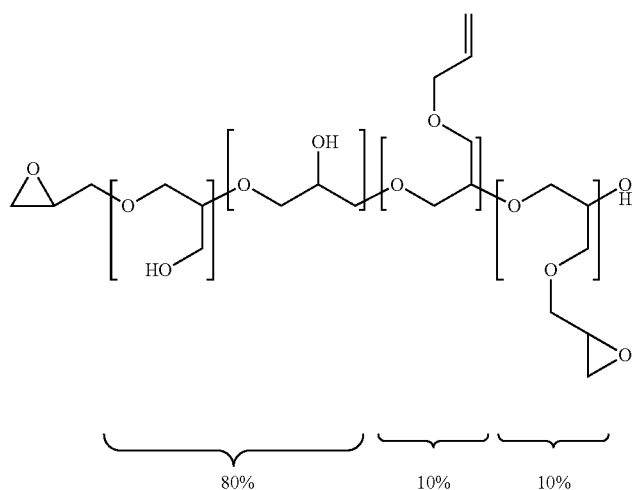

then evaporated on the rotovap to yield the pure white m-CPBA product.[41] $^1$H-NMR (400 MHz, CDCl$_3$) δ: 8.14-8.08 (2H, m, CH, CH), 7.82 (1H, d, CH), 7.59 (1H, m, CH).

(2) Preparation of a-allyl-Δ-valerolactone

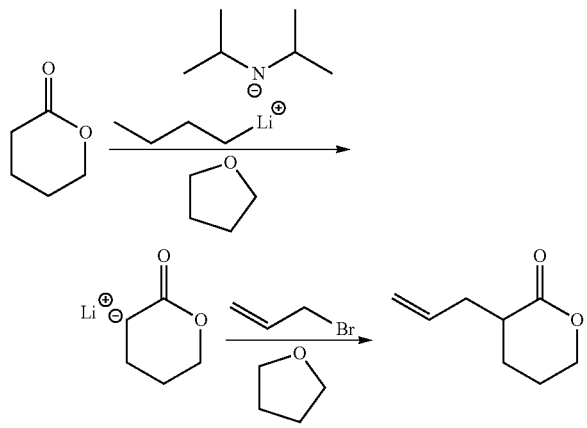

This reaction was performed as previously described in literature with the added use of vacuum distilled δ-valerolactone rather than using the purchased purity.[7, 9, 10] Yield: 2.56 g (46.12%)) $^1$H-NMR (400 MHz, CDCl$_3$) δ: 5.80 (1H, m, CH) 5.04 (2H, m, CH$_2$), 4.27 (2H, m, CH$_2$), 2.42 (2H, m, CH$_2$, CH), 2.18 (1H, m, CH$_2$), 2.00-1.72 (4H, m, CH$_2$). $^{13}$C-NMR (100 MHz, CDCl$_3$) δ: 173.98, 135.03, 117.54, 68.84, 39.13, 35.42, 22.13, 21.05.

(3) Preparation of a-propargyl-Δ-valerolactone

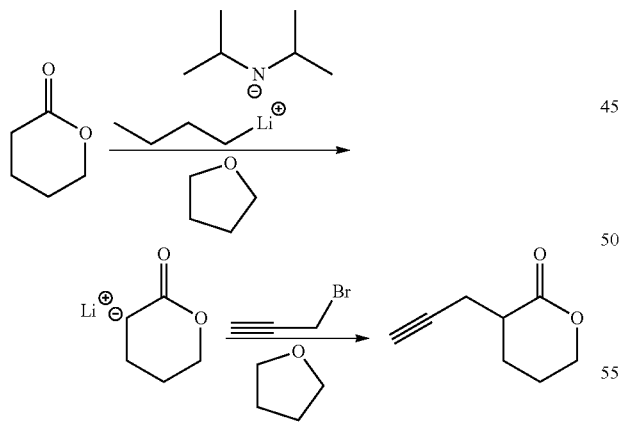

This reaction was performed as previously described in literature with the added use of vacuum distilled δ-valerolactone rather than using the purchased purity.[7, 9, 10] Yield: 2.08 g (53.64%). $^1$H-NMR (400 MHz, CDCl$_3$) δ: 4.34 (2H, m, CH$_2$), 2.71 (1H, m, CH), 2.51 (1H, m, CH$_2$), 2.37 (1H, m, CH), 2.24 (1H, m, CH$_2$), 2.00-1.73 (4H, m, CH$_2$). $^{13}$C-NMR (125 MHz, CDCl$_3$) δ: 171.96, 81.75, 70.14, 68.98, 39.02, 24.21, 21.87, 20.43.

(4) Preparation of 2-oxepane-1,5-dione

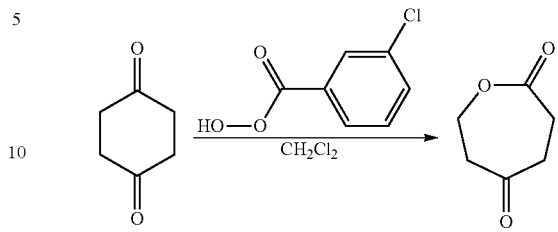

This reaction was performed as previously described in literature with the added use of purified m-CPBA rather than using the purchased purity.[7, 9, 10] Yield: 1.89 g (54.31%). $^1$H-NMR (400 MHz, CDCl$_3$) δ: 4.36 (2H, t, CH$_2$), 2.76 (2H, m, CH$_2$), 2.65 (2H, m, CH$_2$), 2.59 (2H, m, CH$_2$). $^{13}$C-NMR (125 MHz, CDCl$_3$) δ: 205.14, 173.57, 63.74, 44.86, 38.94, 28.31.

(5) Preparation of Diallyl Ester

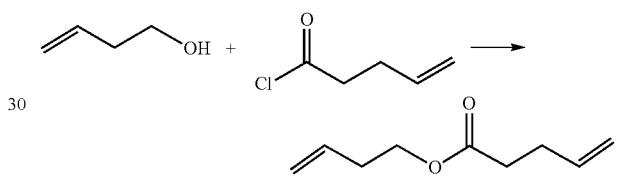

To a round bottom flask equipped with a stir bar, was added 3-buten-1-ol (3.27 g; 45.29 mmol; 1.0 eq) and DCM (25 mL; excess). A diluted solution of 4-pentenoyl chloride (5.37 g; 45.29 mmol; 1.0 eq) and DCM (25 mL; excess) was created in an addition funnel. The 4-pentenoyl chloride solution was then added drop wise to the stirring reaction mixture over 30 minutes and the reaction was allowed to run for 3 h until TLC indicated the reaction was complete. The excess solvent was then removed on the rotovap to afford the crude product. The resulting crude liquid product was on the Biotage column system using a gradient of 8%-70% ethyl acetate in hexanes to yield the pure clear liquid product. Yield: 10.33 g (73.95%). $^1$H-NMR (500 MHz, CDCl$_3$/TMS) δ 5.78 (2H, m, CH), 5.07 (4H, m, CH$_2$), 4.12 (2H, t, CH$_2$O), 2.38 (6H, m, 3CH$_2$). $^{13}$C-NMR (125 MHz, CDCl$_3$) δ 173.22, 136.89, 134.22, 117.38, 115.65, 63.61, 33.73, 33.28, 29.07.

(6) Preparation of Glycidyl Ester Allyl

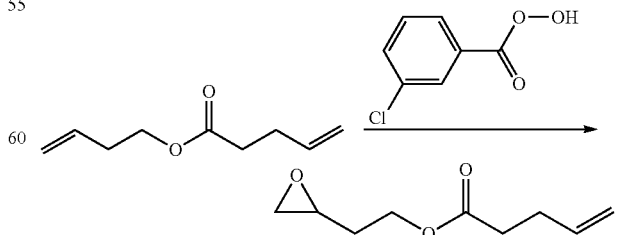

To a round bottom flask equipped with a stir bar, was added the previously synthesized diallyl ester (2.90 g; 18.79 mmol; 1.0 eq), m-CPBA (3.24 g; 18.79 mmol; 1.0 eq), and DCM (53.66 mL; 5.4×10⁻² g/mL). The oxidation reaction was then allowed to run for 48 h. The crude product was then vacuum filtered to remove the white precipitate before extracting the filtrate with saturated sodium bicarbonate to remove any unreacted m-CPBA. The excess DCM was then removed on the rotovap to afford the clear crude liquid product. The resulting crude liquid product was purified on the Biotage column system using a gradient of 8%-70% ethyl acetate in hexanes to yield the pure clear liquid product. Yield: 6.83 g (60.47%). $^1$H-NMR (500 MHz, CDCl$_3$) δ 5.82 (1H, m, CH), 5.09 (2H, m, CH$_2$), 4.41 (1H, dd, CH$_2$), 3.93 (1H, q, CH$_2$), 3.21 (1H, sext, CH), 2.85 (1H, t, CH$_2$), 2.65 (1H, q, CH$_2$), 2.47 (2H, m, CH$_2$), 2.40 (2H, m, CH$_2$). $^{13}$C-NMR (125 MHz, CDCl$_3$) δ 174.27, 138, 116.06, 66.23, 50.42, 45.13, 34.27, 29.96.

(7) Preparation of Mixed Length Diallyl Ester

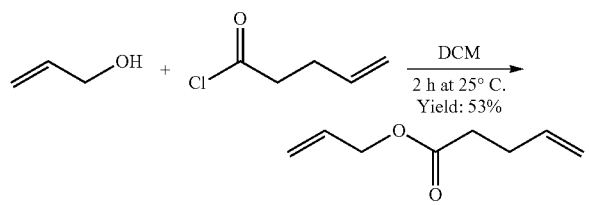

To a round bottom flask equipped with a stir bar, was added allyl alcohol (3.27 g; 45.29 mmol; 1.0 eq) and DCM (25 mL; excess). A diluted solution of 4-pentenoyl chloride (5.37 g; 45.29 mmol; 1.0 eq) and DCM (25 mL; excess) was created in an addition funnel. The 4-pentenoyl chloride solution was then added drop wise to the stirring reaction mixture over 30 minutes and the reaction was allowed to run for 3 h until TLC indicated the reaction was complete. The excess solvent was then removed on the rotovap to afford the crude product. The resulting crude liquid product was purified on the Biotage column system using a gradient of 8%-70% ethyl acetate in hexanes to yield the pure clear liquid product. $^1$H-NMR (500 MHz, CDCl$_3$/TMS) δ 5.78 (2H, m, CH), 5.09 (4.11H, m, CH$_2$), 4.12 (2H, t, CH$_2$O), 2.39 (6.4H, m, 3CH$_2$).

(8) Preparation of Mixed Length Glycidyl Ester Allyl

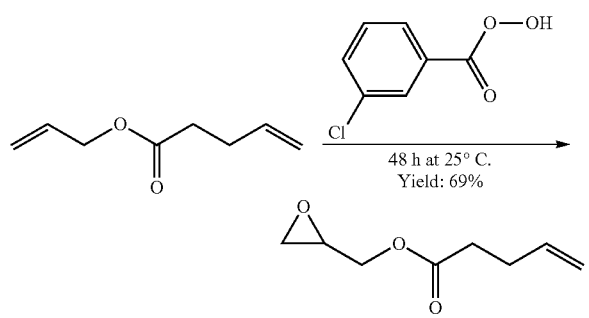

To a round bottom flask equipped with a stir bar, was added the previously synthesized mixed length diallyl ester (2.90 g; 18.79 mmol; 1.0 eq), m-CPBA (3.24 g; 18.789 mmol; 1.0 eq), and DCM (53.657 mL; 5.4×10⁻² g/mL). The oxidation reaction was then allowed to run for 48 h. The crude product was then vacuum filtered to remove the white precipitate before extracting the filtrate with saturated sodium bicarbonate to remove any unreacted m-CPBA. The excess DCM was then removed on the rotovap to afford the clear crude liquid product. The resulting crude liquid product was purified on the Biotage column system using a gradient of 8%-70% ethyl acetate in hexanes to yield the pure clear liquid product. $^1$H-NMR (500 MHz, CDCl$_3$) δ 5.88 (2H, m, CH), 5.22 (4.54H, m, CH$_2$), 2.95 (2.19H, m), 2.72 (2.58H, t), 1.94 (3.06H, m), 1.75, 2.87H).

(9) Preparation of Ethoxyethyl Glycidol Ether

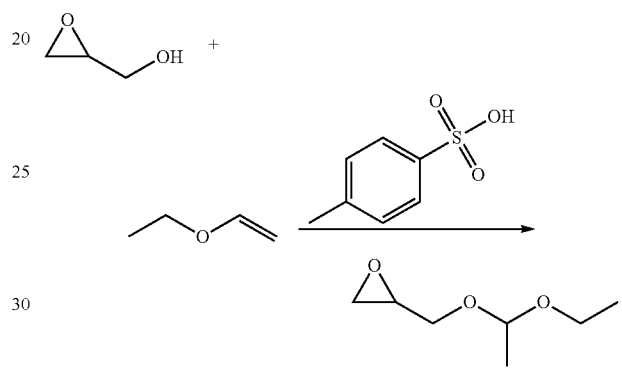

To a round bottom flask equipped with a stir bar was added glycidol (7.41 g; 100 mmol; 1.0 eq) and ethyl vinyl ether (27.88 g; 386.67 mmol; 3.87 eq). The reaction flask was then lowered into a salt water/ice bath at 0° C. and began stirring. P-toluene sulfonic acid (185.2 mg; 0.97 mmol; 0.0097 eq) was then added slowly portionwise in order to maintain the low reaction temperature. The mixture was then allowed to stir at the depressed temperature for 7 h. The reaction was then quenched with saturated NaHCO$_3$ (excess). The organic layer was then separated, dried and evaporated on the rotovap to yield to monomer product. Yield: 182.6 mg (32.47%). $^1$H-NMR (400 MHz, CDCl$_3$) δ: 4.73 (1.95H), 4.09 (1H), 3.78 (1H), 3.66 (3.15H), 3.51 (2.95H), 2.77 (2.01H), 2.61 (1.98H), 1.29 (6.18H), 1.17 (7.97H). $^{13}$C-NMR (100 MHz, CDCl$_3$) δ: 171.21, 99.76, 65.86, 65.19, 60.98, 50.89, 44.64, 21.12, 19.72, 15.35, 14.29.

4. Preparation of Polyesters a. General Procedure for VL Based Polymers

A 25 mL and a 10 mL round bottom flask were flame-dried under N$_2$(g), along with a 50 mL 3-neck round bottom flask equipped with a stir bar. In the 25 mL round bottom flask, an 1.7M EtOH stock solution was formed using dry THF, while the 10 mL round bottom flask was used to create a 3.7×10⁻² M tin triflate stock solution, also using dry THF. The stock solutions were then allowed to sit for 30 minutes before adding Sn(OTf)$_2$ (0.00035 eq) and EtOH (0.066 eq) to the reaction flask. The reaction flask was then brought to the proper reaction temperature before adding the monomers and allowing the polymerization to run to completion.

(1) Preparation of VL Homopolymer

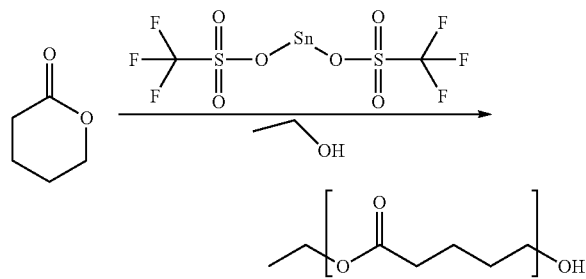

Sn(OTf)$_2$ (0.19 mL; 6.99×10$^{-6}$ mmol; 0.00035 eq) and EtOH (0.29 mL; 5×10$^{-4}$ mmol; 0.066 eq) were added to the reaction flask. The stock solutions were allowed to stir for 10 minutes before adding the δ-valerolactone (2.70 g; 19.98 mmol; 1.0 eq) monomer. The reaction was then allowed to run for 24 h at room temperature. After 24 h the resulting viscous polymer product was precipitated into cold diethyl ether to afford the off-white particulate polymer product. The diethyl ether was decanted from the product, which was then transferred to a 6-dram vial, using ethyl acetate. Yield: 1.83 g (91.5%). $^1$H-NMR (400 MHz, CDCl$_3$) δ: 4.07 (82.79H), 3.63 (6.44H), 3.46 (101.51H), 2.33 (93.10H), 2.21 (33.20H), 1.67 (168.64H), 1.25 (3H). $^{13}$C-NMR (100 MHz, CDCl$_3$) δ: 173.62, 63.89, 62.18, 50.60, 33.62, 32.06, 27.98, 21.34.

(2) Preparation of VL/AVL Linear Polymer (80/20)

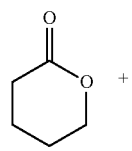 +

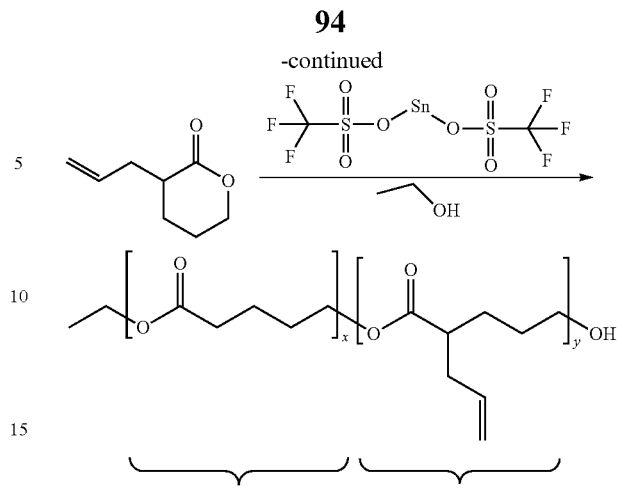

Sn(OTf)$_2$ (0.19 mL; 6.99×10$^{-6}$ mmol; 0.00035 eq) and EtOH (0.29 mL; 5×10$^{-4}$ mmol; 0.066 eq) were added to the reaction flask. The stock solutions were allowed to stir for 10 minutes before adding the δ-valerolactone (1.48 g; 14.80 mmol; 4.0 eq) and α-allyl-δ-valerolactone (0.52 g; 3.70 mmol; 1.0 eq). The reaction was then allowed to run for 24 h at room temperature. After 24 h the resulting viscous polymer product was precipitated into cold diethyl ether to afford the off-white particulate polymer product. The diethyl ether was decanted from the product, which was then transferred to a 6-dram vial, using ethyl acetate. Yield: 1.3815 g (69.08%). $^1$H-NMR (400 MHz, CDCl$_3$) δ: 5.72 (1H), 5.03 (2H), 4.08 (11.52H), 2.35 (11.77H), 1.67 (24.01H), 1.27 (1.85H). $^{13}$C-NMR (100 MHz, CDCl$_3$) δ: 175.30, 173.42, 135.36, 117.11, 64.07, 62.37, 60.50, 44.98, 36.59, 33.93, 32.23, 28.23, 26.57, 21.57, 21.28, 14.39.

(3) Preparation of VI/OPD/AVL Linear Polymer (60/20/20)

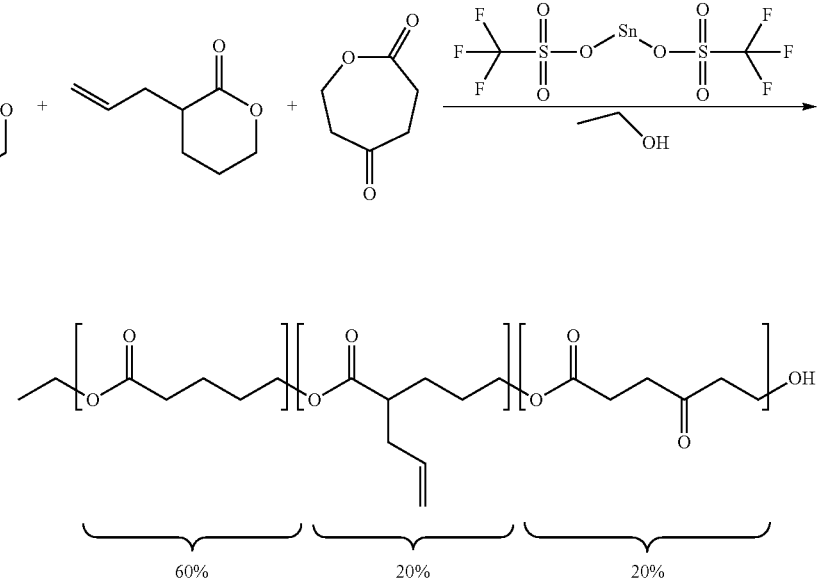

Sn(OTf)$_2$ (0.30 mL; 8.83×10$^{-6}$ mmol; 0.00035 eq) and EtOH (0.29 mL; 3.33×10$^{-4}$ mmol; 0.066 eq) were added to the reaction flask. The stock solutions were allowed to stir for 10 minutes before adding the δ-valerolactone (1.92 g; 19.20 mmol; 3.0 eq), 2-oxepane-1,5-dione (0.82 g; 6.40 mmol; 1.0 eq), and the previously synthesized α-allyl-δ-valerolactone (0.90 g; 6.40 mmol; 1.0 eq). The reaction was then allowed to run for 24 h at room temperature. After 24 h the resulting viscous polymer product was precipitated into cold diethyl ether to afford the off-white particulate polymer product. The diethyl ether was decanted from the product, which was then transferred to a 6-dram vial, using ethyl acetate. Yield: 2.912 g (97.07%). $^1$H-NMR (400 MHz, CDCl$_3$) δ: 5.71 (1H, m, CH), 5.03 (2H, m, CH$_2$), 4.34 (2H), 4.08 (10.79H), 3.67 (1.04H), 2.52-2.86 (6.68H), 2.15-2.51 (13.22H), 1.67 (22.63H). $^{13}$C-NMR (100 MHz, CDCl$_3$) δ: 135.33, 117.73, 69.64, 68.76, 64.11, 39.57, 35.71, 33.89, 30.05, 28.26, 24.36, 22.53, 21.61, 19.33.

(4) Preparation of VL/PVL/OPD Linear Polymer (70/20/10)

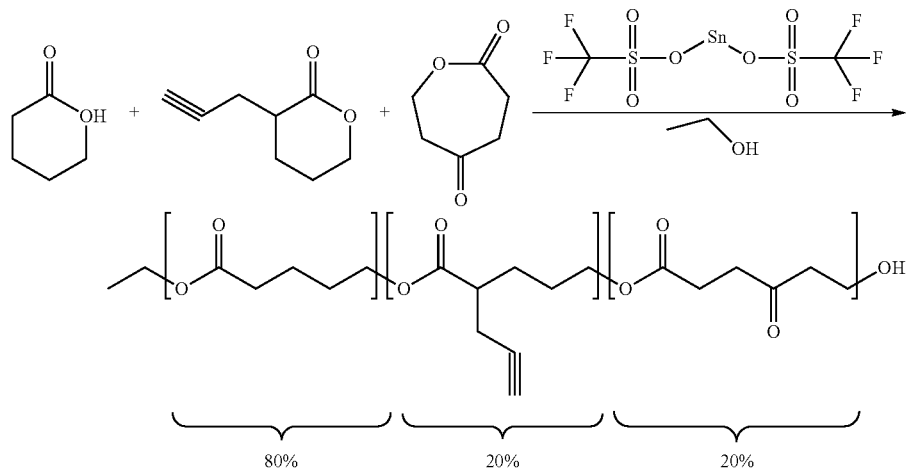

Sn(OTf)$_2$ (0.26 mL; 9.50×10$^{-6}$ mmol; 0.00035 eq) and EtOH (0.29 mL; 5×10$^{-4}$ mmol; 0.066 eq) were added to the reaction flask. The stock solutions were allowed to stir for 10 minutes before adding the δ-valerolactone (1.90 g; 19.00; 7.0 eq), the previously synthesized α-propargyl-δ-valerolactone (0.75 g; 5.43 mmol; 2.0 eq), and the previously synthesized α-propargyl-δ-valerolactone 2-oxepane-1,5-dione (0.35 g; 2.71 mmol; 1.0 eq). The reaction was then allowed to run for 24 h at room temperature. After 24 h the resulting viscous polymer product was precipitated into cold diethyl ether to afford the off-white particulate polymer product. The diethyl ether was decanted from the product, which was then transferred to a 6-dram vial, using ethyl acetate. Yield: 1.58 g (52.58%). $^1$H-NMR (400 MHz, CDCl$_3$) δ: 4.34 (1.91H), 4.07 (32.58H), 3.67 (1.76H), 3.41 (1.32H), 2.24-2.83 (42.88H), 2.02 (3.03H), 1.67 (63.84H), 1.25 (3H). $^{13}$C-NMR (100 MHz, CDCl$_3$) δ: 173.42, 70.36, 64.06, 60.54, 53.59, 44.11, 42.98, 41.58, 33.83, 28.21, 25.25, 21.56, 14.33.

(5) Oxidation of VL/AVL Linear Polymer (80/20)

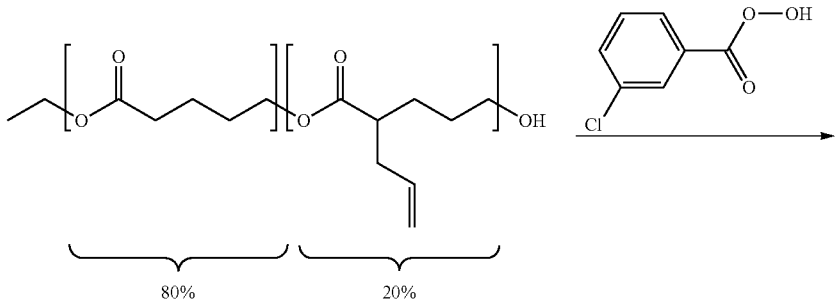

-continued

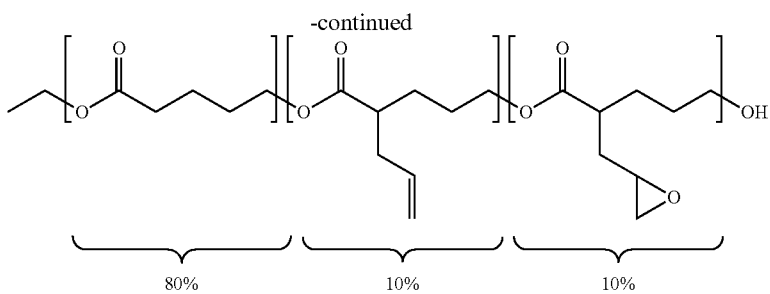

To a round bottom flask equipped with a stir bar, was added the VL/AVL polymer (2.55 g; 3.87 mmol; 2.0 eq), m-CPBA (0.44 g; 2.15 mmol; 1.0 eq), and dichloromethane (47.2 mL; 5.4×10$^{-2}$ g/mL). The round bottom flask was then capped with a septum and allowed to stir for 72 h at room temperature. The resulting product solution was then concentrated and precipitated into cold methanol. The methanol was decanted from the product, which was then transferred to a 6-dram vial using dichloromethane. Yield: 835.6 mg (64.28%). $^1$H-NMR (400 MHz, CDCl$_3$) δ: 5.72 (1H), 5.04 (2.07H), 4.08 (41.05H), 3.66 (2.77H), 2.93 (0.84H), 2.75 (0.95H), 2.29-2.53 (42.04), 1.69 (92.19H), 1.26 (2.15H). $^{13}$C-NMR (100 MHz, CDCl$_3$) δ: 173.47, 135.26, 117.16, 64.97, 62.35, 60.49, 44.97, 36.58, 33.83, 32.20, 28.19, 26.56, 21.58, 21.27, 14.38.

(6) Oxidation of VL/OPD/AVL Linear Polymer (60/20/20)

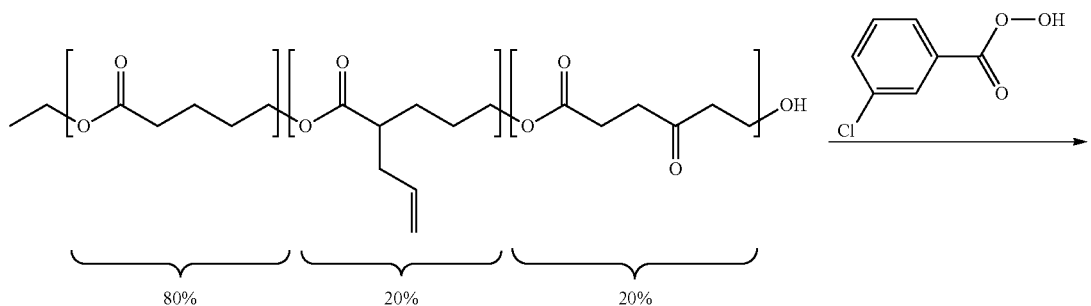

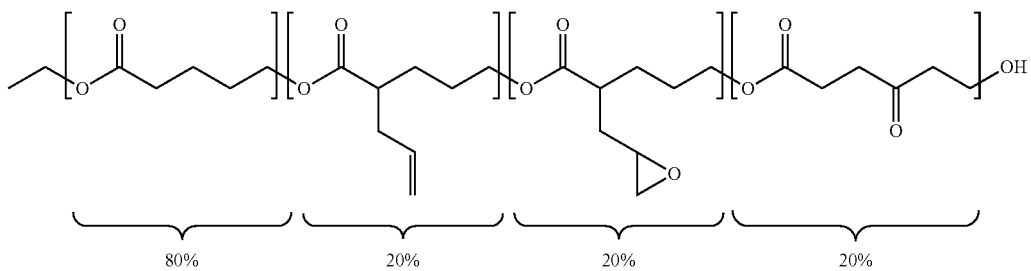

To a round bottom flask equipped with a stir bar, was added the VL/OPD/AVL polymer (0.35 g; 0.52 mmol; 2.0 eq), m-CPBA (51.89 mg; 0.26 mmol; 1.0 eq), and dichloromethane (6.511 mL; 5.4×10⁻² g/mL). The round bottom flask was then capped with a septum and allowed to stir for 72 h at room temperature. The resulting product solution was then concentrated and precipitated into cold methanol. The methanol was decanted from the product, which was then transferred to a 6-dram vial using dichloromethane. Yield: 367 mg (84.95%). $^1$H-NMR (400 MHz, CDCl$_3$) δ: 5.73 (1H), 5.05 (2.15H), 4.36 (4.29H), 4.11 (14.01H), 3.90 (2.04H), 3.67 (5.04H), 3.43 (1.13H), 2.52-2.86 (21.18H), 2.16-2.52 (18.28H), 1.69 (34.37H), 1.27 (1.59H). $^{13}$C-NMR (150 MHz, CDCl$_3$) δ: 169.68, 134.83, 133.87, 131.26, 129.99, 128.42, 64.12, 53.60, 33.88, 28.24, 21.60.

5. Preparation of New Crosslinkers (1) Preparation of Disulfide Linker

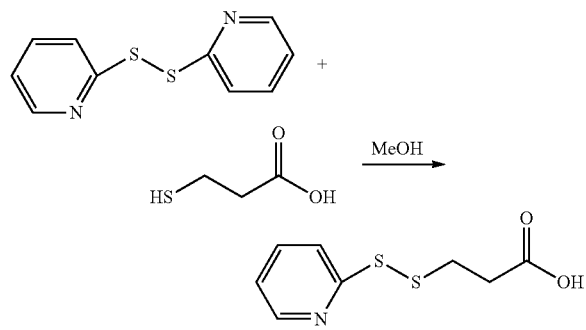

To a round bottom flask equipped with a stir bar, was added aldrithiol-2 (10.00 g; 1.5 eq), 3-mercaptopropionic acid (3.212 g; 1.0 eq), and MeOH (excess). The yellow reaction was then allowed to stir for 72 h. The resulting yellow solution was concentrated and the yellow product was resuspended in dichloromethane and dried onto silica gel. The product was then purified through column chromatography using a gradient of 10%-30% ethyl acetate in hexanes to yield the pure, slightly off-white solid product. Yield: 2.23 g (34.17%). $^1$H-NMR (400 MHz, CDCl$_3$) δ: 8.39 (1H), 7.81 (2H), 7.22 (1H), 3.03 (2H), 2.71 (2H). $^{13}$C-NMR (100 MHz, CDCl$_3$) δ: 175.56, 159.39, 149.60, 137.64, 121.46, 120.85, 34.37, 34.24.

(2) Preparation of Disulfide Amine Crosslinker

To a round bottom flask equipped with a stir bar, in an ice bath, was added the previously synthesized disulfide linker (0.50 g; 2.32 mmol; 6.0 eq), THF (excess), and triethylamine (0.33 g; 3.25 mmol; 8.4 eq), followed by the slow addition of isobutyl chloroformate (0.40 g; 2.90 mmol; 7.5 eq). The reaction was then allowed to stir for 3 hours. To the stirring reaction mixture was then added pentaethylenehexamine (0.09 g; 0.39 mmol; 1.0 eq) slowly drop wise. The reaction was then removed from the ice bath and allowed to run for an additional 24 hours at room temperature. The excess solvent was then removed on the rotovap to afford the crude, deep red product. The resulting crude product was purified on the Biotage column system using a gradient of 2%-20% ethyl acetate in hexanes to yield the pure, slightly off-white solid product. $^1$H-NMR (400 MHz, CDCl$_3$) δ: 8.42 (2H), 7.48 (2H), 7.18 (2.01H), 6.98 (2.15H) 3.90 (4.56H), 3.45 (4.17H), 3.34 (1.16H), 2.89 (1.06H), 2.80 (4.35H), 1.13 (0.96H), 0.94 (15.11H). $^{13}$C-NMR (100 MHz, CDCl$_3$) δ: 172.33, 158.41, 149.57, 136.17, 122.62, 119.65, 53.61, 42.93, 34.93, 27.88, 25.18, 19.27.

6. Preparation of Nanoparticles (1) Nanoparticle Formation Through Thiolene-Click Reactions Using VL/OPD/AVL Copolymers (50 nm)

To a round bottom flask equipped with a stir bar, was added the VL/OPD/AVL polymer (111.5 mg; 5.431×10⁻² mmol; 1 eq), 3,6-dioxa-1,8-octanedithiol (9.90 mg; 5.431× 10⁻² mmol; 1 eq), and dichloromethane (16.76 mL; 3.24× 10⁻³M). The flask was then fitted with a reflux condenser and lowered into an oil bath at 45° C. to reflux for 12 h. The resulting solution was then transferred to 10K dialysis tubing and dialyzed for 72 h against dichloromethane to remove any unreacted starting material. The remaining product solution was then concentrated into a preweighed vial and stored in the fridge. Yield: 81.8 mg (66.17%). $^1$H-NMR (600 MHz, CDCl$_3$) δ: The significant change is the reduction of the allyl peaks at 5.72 and 5.04 ppm and the appearance of signals at 3.65 and 2.69 ppm corresponding to the protons neighboring the thiols of the PEG linker after cross-linking. All other aspects of the spectrum remain similar to the polymer spectrum.

(2) Nanoparticle Formation Through Thiolene-Click Reactions Using GLY/VL/AVL Copolymers (50 nm)

To a round bottom flask equipped with a stir bar, was added the GLY/VL/AVL polymer (118.75 mg; 2.74×10⁻² mmol; 1 eq), 3,6-dioxa-1,8-octanedithiol (5.00 mg; 2.74× 10⁻² mmol; 1 eq), and methanol (8.47 mL; 3.24×10⁻³M).

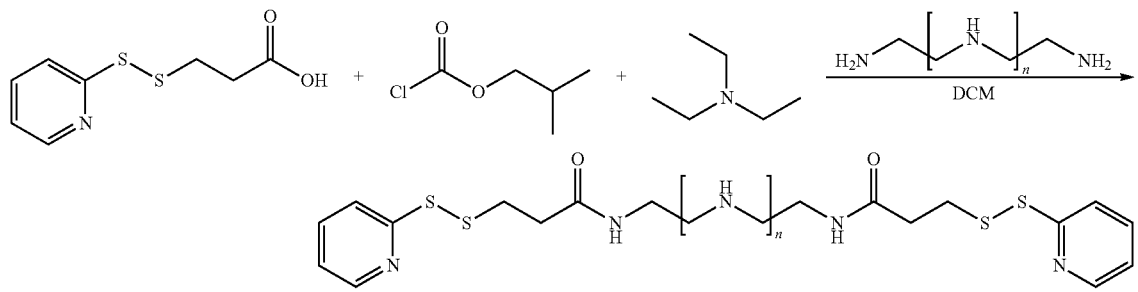

The flask was then fitted with a reflux condenser and lowered into an oil bath at 45° C. to reflux for 12 h. The resulting solution was then transferred to 10K dialysis tubing and dialyzed for 72 h against dichloromethane to remove any unreacted starting material. The remaining product solution was then concentrated into a preweighed vial and stored in the fridge. Yield: 115.6 mg (93.41%). $^1$H-NMR (600 MHz, CDCl$_3$) δ: The significant change is the reduction of the allyl peaks at 5.72 and 5.04 ppm and the appearance of signals at 3.65 and 2.69 ppm corresponding to the protons neighboring the thiols of the PEG linker after cross-linking. All other aspects of the spectrum remain similar to the polymer spectrum.

(3) Nanoparticle Formation Through Thiolene-Click Reactions Using GLY/AGE Copolymers (50 Nm)

Figure 24:
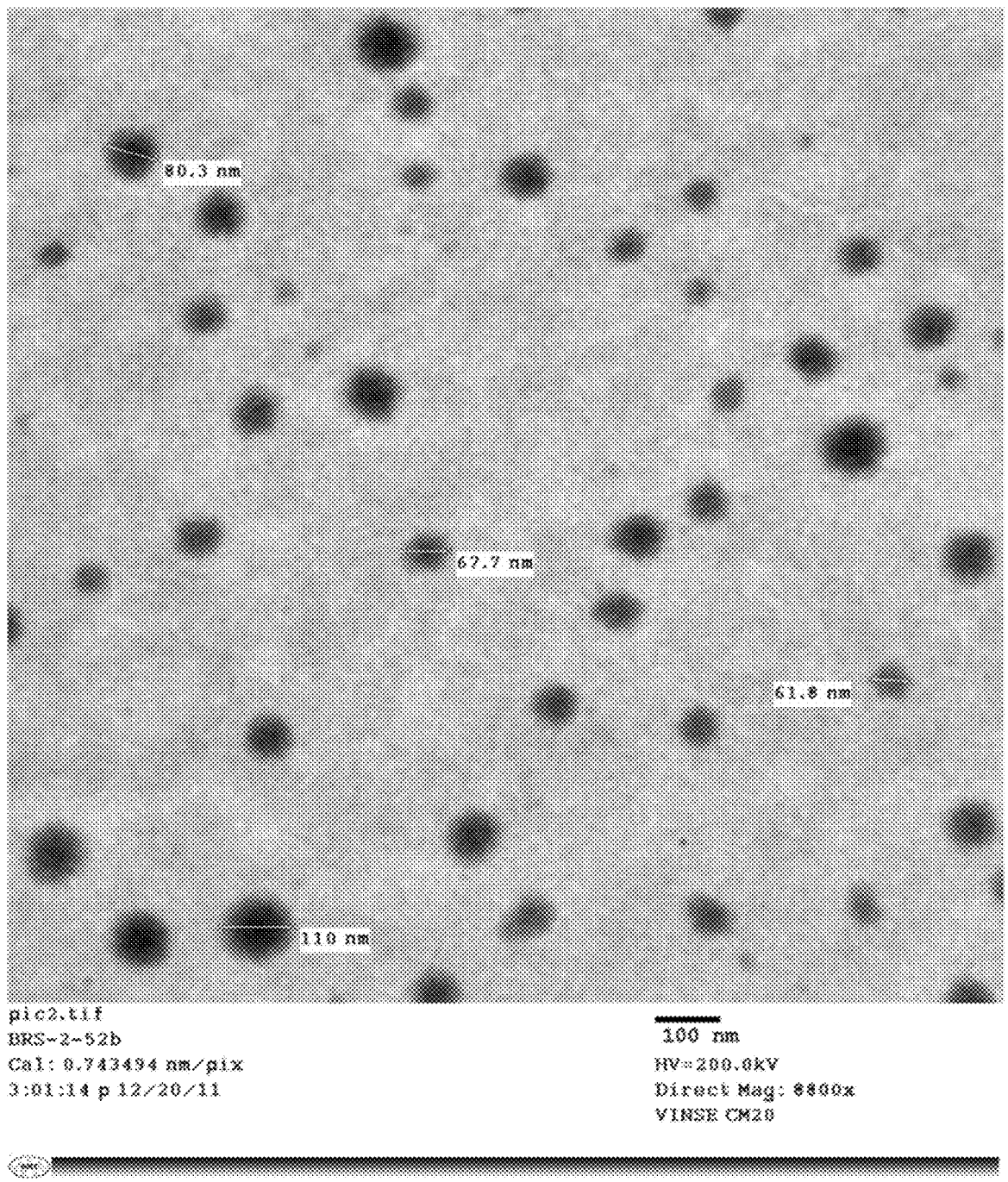
FIG. 24 shows a transmission electron microscopy (TEM) image for GLY/AGE nanoparticles of the present invention.
Figure 25:
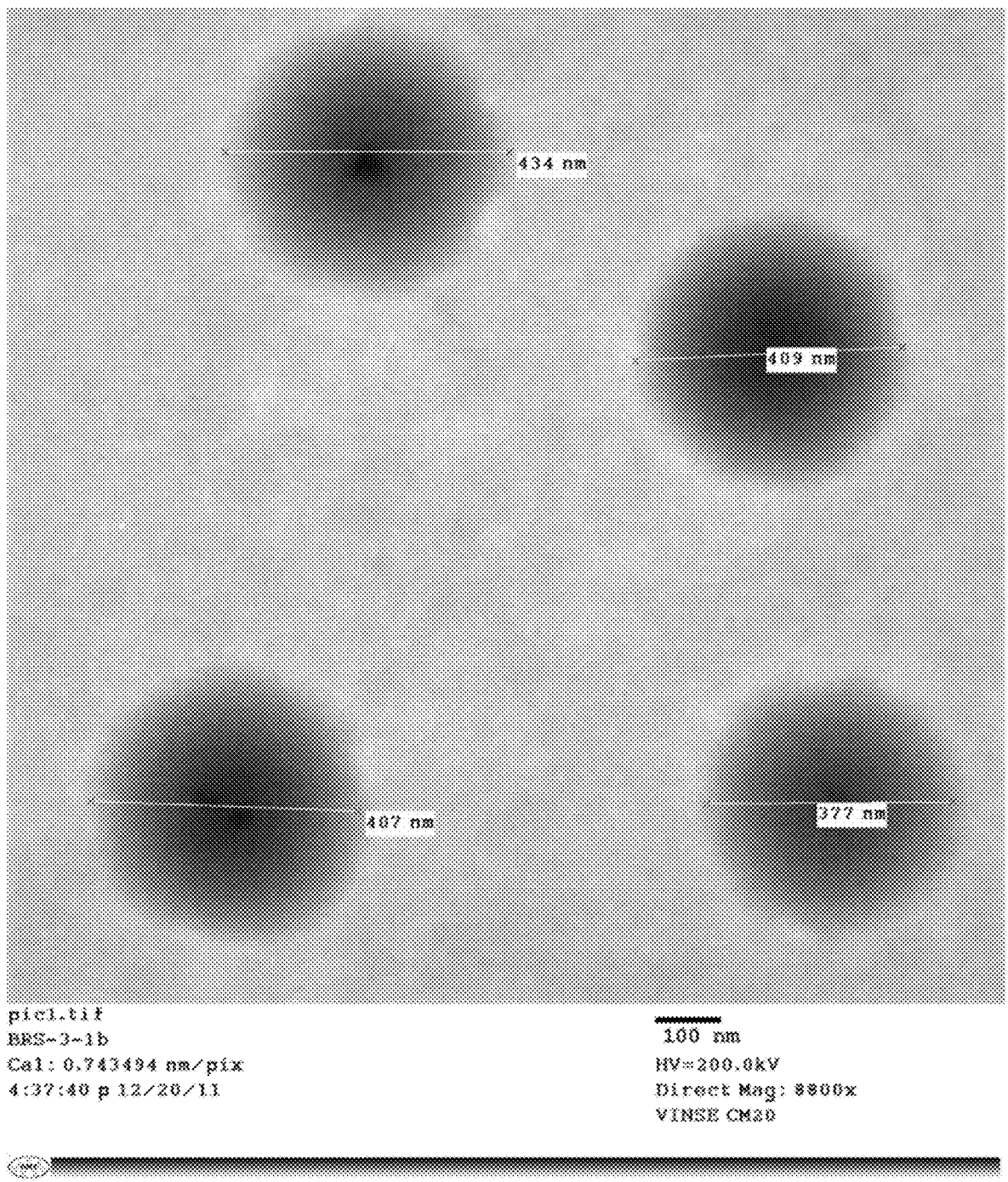
FIG. 25 shows a transmission electron microscopy (TEM) image for GLY/AGE nanoparticles of the present invention.
Figure 26:
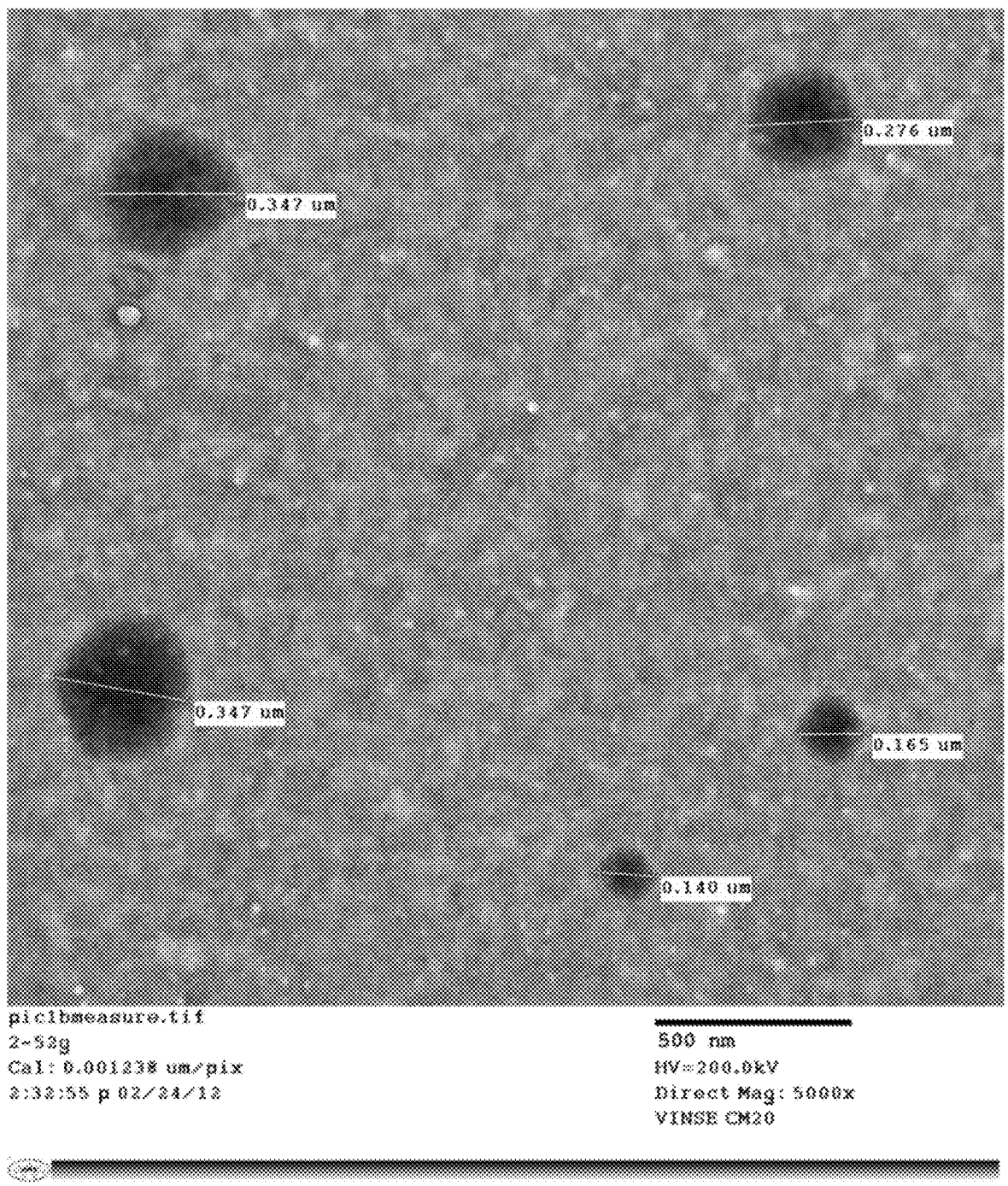
FIG. 26 shows a transmission electron microscopy (TEM) image for GLY/AGE nanoparticles of the present invention.

To a round bottom flask equipped with a stir bar, was added the GLY/AGE polymer (111 mg; $1.79 \times 10^{-1}$ mmol; 2 eq), 3,6-dioxa-1,8-octanedithiol (16.35 mg; $8.97 \times 10^{-2}$ mmol; 1 eq), and methanol (55.36 mL; $3.24 \times 10^{-3}$M). The flask was then fitted with a reflux condenser and lowered into an oil bath at 45° C. to reflux for 12 h. The resulting solution was then transferred to 10K dialysis tubing and dialyzed for 72 h against methanol to remove any unreacted starting material. The remaining product solution was then concentrated into a preweighed vial and stored in the fridge. Yield: 103.1 mg (84.14%). $^1$H-NMR (600 MHz, CDCl$_3$) δ: The significant change is the reduction of the allyl peaks at 5.72 and 5.04 ppm and the appearance of signals at 3.65 and 2.69 ppm corresponding to the protons neighboring the thiols of the PEG linker after cross-linking. All other aspects of the spectrum remain similar to the polymer spectrum. FIG. 24 shows transmission electron microscopy (TEM) image for GLY/AGE nanoparticles with 3.5% crosslinking, after running reaction for 12 hours in methanol at 45° C. FIG. 25 shows transmission electron microscopy (TEM) image for GLY/AGE nanoparticles with 7% crosslinking, after running reaction for 12 hours in methanol at 65° C. FIG. 26 shows transmission electron microscopy (TEM) image for GLY/AGE nanoparticles with 7% crosslinking, after running reaction for 12 hours in methanol at 45° C.

(4) Nanoparticle Formation Through Thiolene-Click Reactions Using GLY/GEA Copolymers (50 nm)

To a round bottom flask equipped with a stir bar, was added the GLY/GEA polymer (108.5 mg; $6.09 \times 10^{-2}$ mmol; 1 eq), 3,6-dioxa-1,8-octanedithiol (11.1 mg; $6.09 \times 10^{-2}$ mmol; 1 eq), and methanol (18.80 mL; $3.24 \times 10^{-3}$M). The flask was then fitted with a reflux condenser and lowered into an oil bath at 45° C. to reflux for 12 h. The resulting solution was then transferred to 10K dialysis tubing and dialyzed for 72 h against methanol to remove any unreacted starting material. The remaining product solution was then concentrated into a preweighed vial and stored in the fridge. Yield: 28.9 mg (23.92%). $^1$H-NMR (600 MHz, CDCl$_3$) δ: The significant change is the reduction of the allyl peaks at 5.72 and 5.04 ppm and the appearance of signals at 3.65 and 2.69 ppm corresponding to the protons neighboring the thiols of the PEG linker after cross-linking. All other aspects of the spectrum remain similar to the polymer spectrum.

(5) Nanoparticle Formation Through Amine-Epoxide Reactions Using VL/AVL/EVL Copolymers To a round bottom flask equipped with a stir bar, was added the VL/AVL/EVL polymer (30.1 mg; $2.45 \times 10^{-2}$ mmol; 2 eq), 2,2'-(Ethylenedioxy)bis-(ethylamine) (2.717 mg; $1.83 \times 10^{-2}$ mmol; 1.5 eq), and dichloromethane (7.54 mL; $3.24 \times 10^{-3}$M). The flask was then fitted with a reflux condenser and lowered into an oil bath at 45° C. to reflux for 12 h. The resulting solution was then transferred to 10K dialysis tubing and dialyzed for 72 h against dichloromethane to remove any unreacted starting material. The remaining product solution was then concentrated into a preweighed vial and stored in the fridge. Yield: 15.5 mg (47.4%). $^1$H-NMR (600 MHz, CDCl$_3$) δ: The significant change is the reduction of the allyl peaks at 2.96, 2.75, and 2.47 ppm and the appearance of signals at 3.5 and 2.89 ppm corresponding to the protons neighboring the secondary amine of the PEG linker after cross-linking. All other aspects of the spectrum remain similar to the polymer spectrum.

(6) Nanoparticle Formation Through Amine-Epoxide Reactions Using VL/AVL/EVL/OPD Copolymers To a round bottom flask equipped with a stir bar, was added the VL/AVL/EVL/OPD polymer (83.6 mg; $5.67 \times 10^{-2}$ mmol; 2 eq), 2,2'-(Ethylenedioxy)bis-(ethylamine) (6.30 mg; $4.25 \times 10^{-2}$ mmol; 1.5 eq), and dichloromethane (17.49 mL; $3.24 \times 10^{-3}$M). The flask was then fitted with a reflux condenser and lowered into an oil bath at 45° C. to reflux for 12 h. The resulting solution was then transferred to 10K dialysis tubing and dialyzed for 72 h against dichloromethane to remove any unreacted starting material. The remaining product solution was then concentrated into a preweighed vial and stored in the fridge. Yield: 72.6 mg (79.06%). $^1$H-NMR (600 MHz, CDCl$_3$) δ: The significant change is the reduction of the allyl peaks at 2.96, 2.75, and 2.47 ppm and the appearance of signals at 3.5 and 2.89 ppm corresponding to the protons neighboring the secondary amine of the PEG linker after cross-linking. All other aspects of the spectrum remain similar to the polymer spectrum.

7. Preparation of Combination of the Dual Two Component Drug Delivery System a. General Procedure (for 17 Injections (20 μL Per Injection))

Bone morphogenetic protein (BMP2, 17 μL, 10 mg/mL in 20 mM acetic acid) was added to 159 mg polyglycidol. Nanoparticles containing MEK inhibitor (6.4% wt/wt) were dissolved in 244 μL sterile PBS to make 0.236 mg/mL solution with respect to MEK inhibitor. Nanoparticle-MEK (4% crosslinked nanoparticle and 13% loading of inhibitor) inhibitor solution was added to the polyglycidol and BMP2 mixture and sonicated to yield a viscous, but injectable solution (final polyglycidol concentration is 0.466 g/mL, each injection contains 10 μg BMP2 and 3.4 μg MEK inhibitor).

8. Preparation of Reconfigurable and Responsive Network Systems (1) Non-Functionalized Polyglycidol-Based Crosslinking Materials for Hydrogels: As Fillers in Hydrogels and as Component in Reconfigurable and Responsive Network Systems

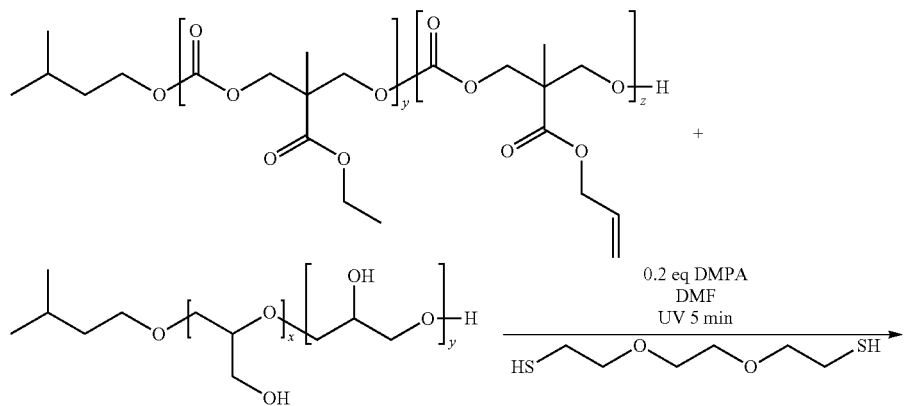

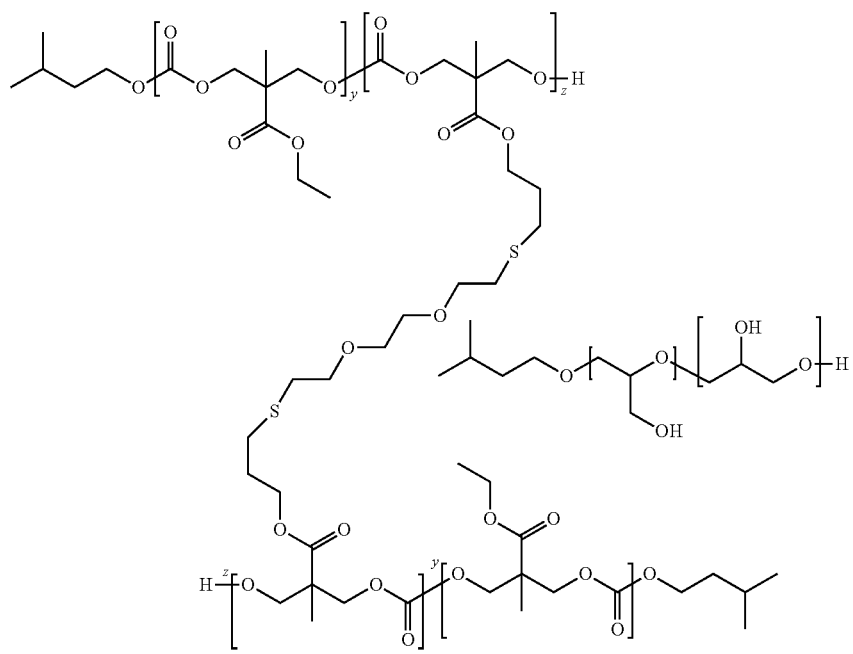

A mixture of poly(MEC, MAC) (100 mg, $M_n$=4,700 g/mol, 0.10 mmol alkene), polyglycidol (100 mg, $M_n$=6,000 g/mol), and 2,2-dimethoxy-2-phenylacetophenone (DMPA, 5.4 mg, 0.02 mmol) was dissolved in DMF (0.10 mL) and allowed to stir at room temperature. 3,6-dioxa-1,8-octanedithiol (17 µL, 0.10 mmol) was added and reaction was exposed to UV light (365 nm) for 5 minutes. The resulting gel was washed in sequence with water, methanol, and dichloromethane and allowed to dry overnight in vacuo to yield a slightly opaque gel.

(2) Preparation of Polycarbonate/Polyglycidol Hydrogel Formation Via Thiolene Click and Zinc Acetate Rearrangement
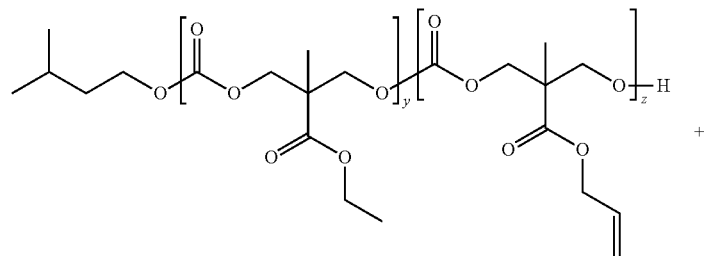
+
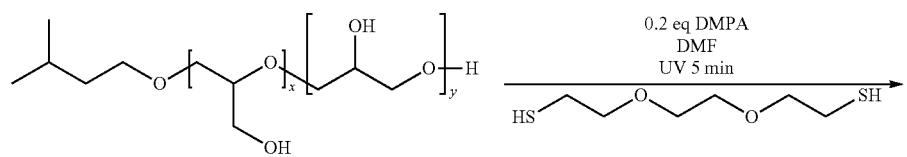
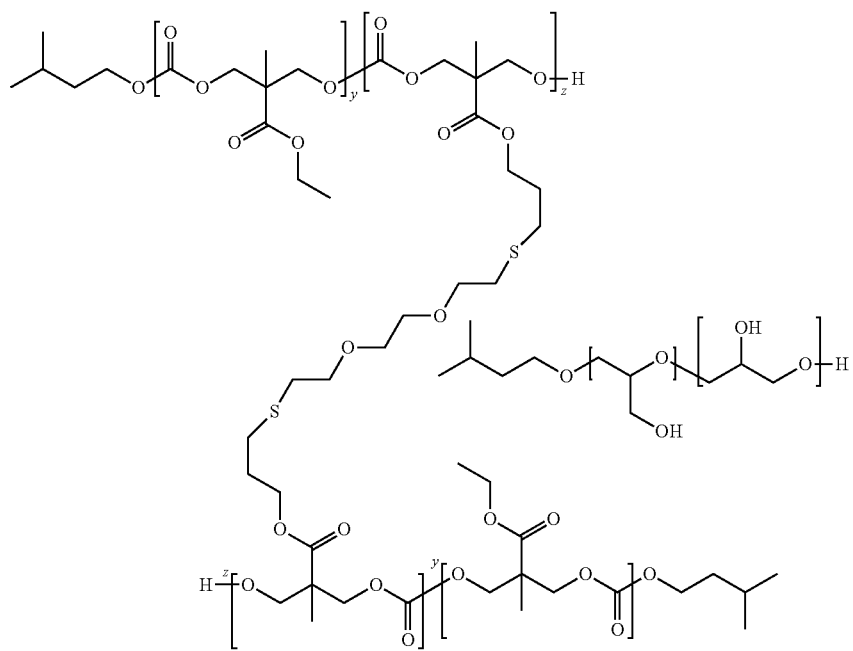

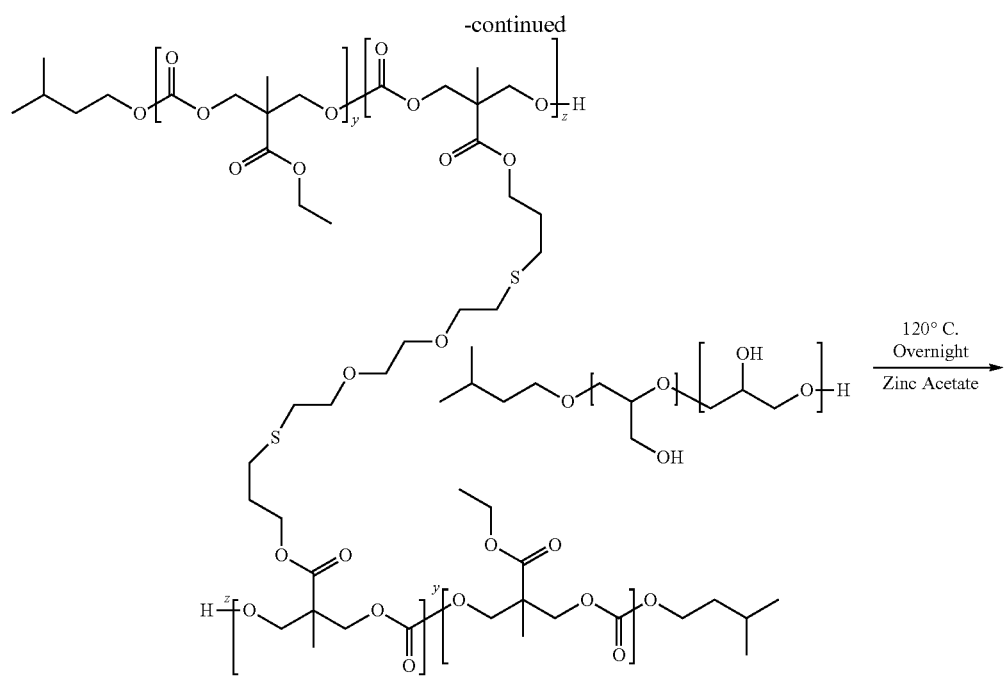

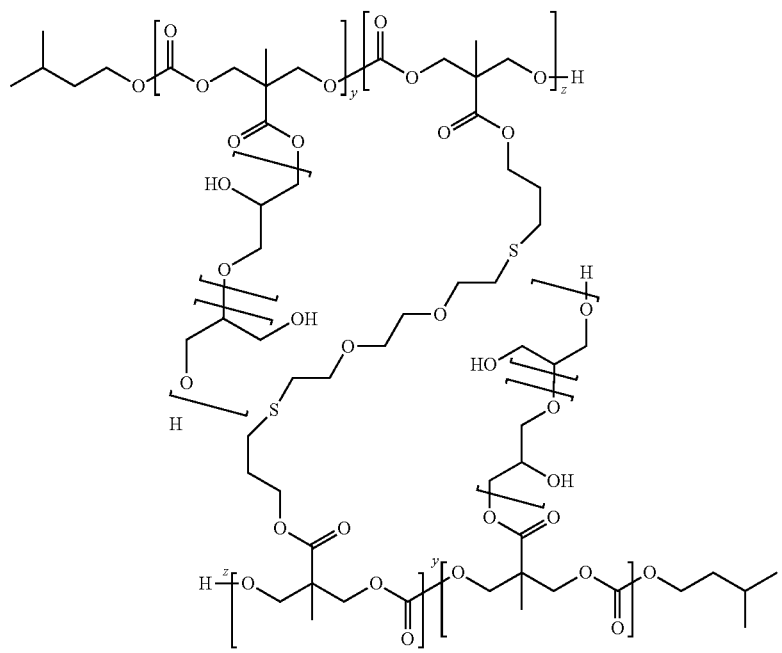

A mixture of poly(MEC, MAC) (100 mg, Mn=4,700 g/mol, 0.10 mmol alkene), polyglycidol (100 mg, Mn=6,000 g/mol), and 2,2-dimethoxy-2-phenylacetophenone (DMPA, 5.4 mg, 0.02 mmol) was dissolved in DMF (0.10 mL) and allowed to stir at room temperature. 3,6-dioxa-1,8-octane- dithiol (17 µL, 0.10 mmol) was added via microsyringe, followed by the addition of zinc acetate (5.8 mg, 0.03 mmol). The reaction was exposed to UV light (365 nm) for 5 minutes. The resulting gel was then placed in a 120° C. oil bath overnight. The product washed in sequence with water, methanol, and dichloromethane and allowed to dry overnight in vacuo to yield a light yellow gel.

9. Preparation of Functionalized Polyglycidols a. General Procedure

All reagents and solvents were commercial grade and purified prior to use when necessary. Tetrahydrofuran was dried by passage through a column of activated alumina as described by Grubbs (Pangborn, A. B *Organometallics* 1996, 15, 1518-1520). Dimethylformamide was distilled over $CaH_2$ and stored over molecular sieves. Glycidol was distilled under vacuum and stored over molecular sieves. Thin layer chromatography (TLC) was performed using glass-backed silica gel (250 μm) plates and flash chromatography utilized 230-400 mesh silica gel from Sorbent Technologies. Size exclusion chromatography was utilized Sephadex LH-20 from Sigma Aldrich. UV light, and/or the use of CAM and potassium permanganate solutions were used to visualize products.

Nuclear magnetic resonance spectra (NMR) were acquired on a Bruker DRX-500 (500 MHz), Bruker AV-400 (400 MHz) or Bruker AV II-600 (600 MHz) instrument. Chemical shifts are measured relative to residual solvent peaks as an internal standard set to δ 7.26 and δ 77.0 ($CDCl_3$), δ 3.31 and δ 49.0 ($CD_3OD$). IR spectra were recorded on a Thermo Nicolet IR100 spectrophotometer and are reported in wavenumbers ($cm^{-1}$). Compounds were analyzed as neat films on a NaCl plate (transmission).

(1) Preparation of N-oxyphthalimide Polyglycidol Derivative

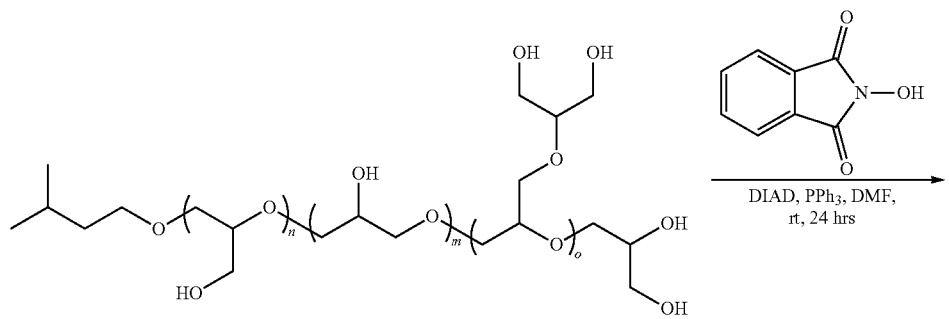

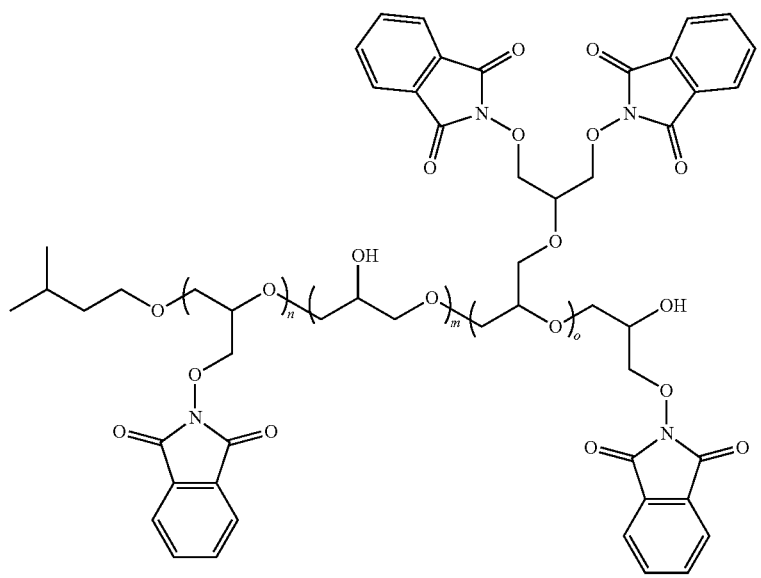

Polyglycidol was synthesized according to known literature procedure (Spears, B. R. *Chem. Commun.* 2013, 49, 2394-2396). To a 50 mL round bottom flask fitted with an argon balloon and containing a solution of polyglycidol ($M_n$=2-3 kDa, 2.0 g) in DMF (25 mL) was added N-Hydroxyphthalimide (2.3 g, 14 mmol) followed by triphenylphosphine (3.7 g, 14 mmol) at rt. Diisopropylazodicarboxylate (2.7 mL, 14 mmol) was then added dropwise and the resulting mixture was stirred at rt for 24 hrs. The reaction was concentrated under reduced pressure and precipitated twice in ether:ethyl acetate (1:1) to obtain 2.6 g of the desired polymer as an off-white solid. IR (film) 3455, 3061, 2919, 1789, 1730, 1373, 1127, 731 cm$^{-1}$; $^1$H NMR (600 MHz, CDCl$_3$) δ 7.74-7.48 (br m, 4H), 3.06-4.49 (br m, 6H); $^{13}$C NMR (600 MHz, CDCl$_3$) ppm 162.8, 134.7, 128.0, 123.4, 79.2, 77.8, 76.6, 74.9, 72.1, 71.4, 71.5-68.0 (br overlapping), 67.3, 65.2, 63.1, 61.2.

(2) Preparation of Aminooxy Polyglycidol Derivative

To a 50 mL round bottom flask equipped with a stir bar and an argon balloon was added a solution of N-oxyphthalimide polyglycidol (1.0 g) in 1:1 mixture of methanol and dichloromethane (25 mL). A 10 fold excess (based on measurements from the synthesis of N-oxyphthalimide polyglycidol) of anhydrous hydrazine (4.5 mL, 140 mmol) was added and the reaction was allowed to stir for 12 hrs at rt. The reaction mixture was filtered through 0.2 μm PTFE filter to remove the white solid byproduct. Further purification by precipitation in ether followed by size exclusion chromatography (sephadex LH-20 in methanol) yielded 800 mg of the desired polymer. IR (film) 3407, 2873, 1373, 1113 cm$^{-1}$; $^1$H NMR (600 MHz, CD$_3$OD) δ 3.50-4.49 (br m, 6H); $^{13}$C NMR (600 MHz, CD$_3$OD) ppm 79.9, 79.4, 78.6, 77.7, 74.7, 72.6, 72.0, 71.9-70.4 (br overlapping peaks), 70.0-68.8 (br, overlapping peaks), 66.2, 63.0, 61.9, 61.3.

As would be appreciated by those of skill, the percentage of the amino-oxy can be readily adjusted and has been done for other examples.

(3) Azide-Functionalized Polyglycidols and Allyl-Functionalized Polyglycidols (A) Preparation of Alkyne Functionalization of Polyglycidol (Method 1)

A mixture of the appropriate propargyl bromide (1.00 equiv), polyglycidol secondary hydroxyl group (1.00 equiv), dried potassium carbonate (1.25 equiv), and 18-crown-6 (0.2 equiv) in DMF was heated at 60° C. and stirred vigorously under nitrogen for 24 h. The mixture was allowed to cool

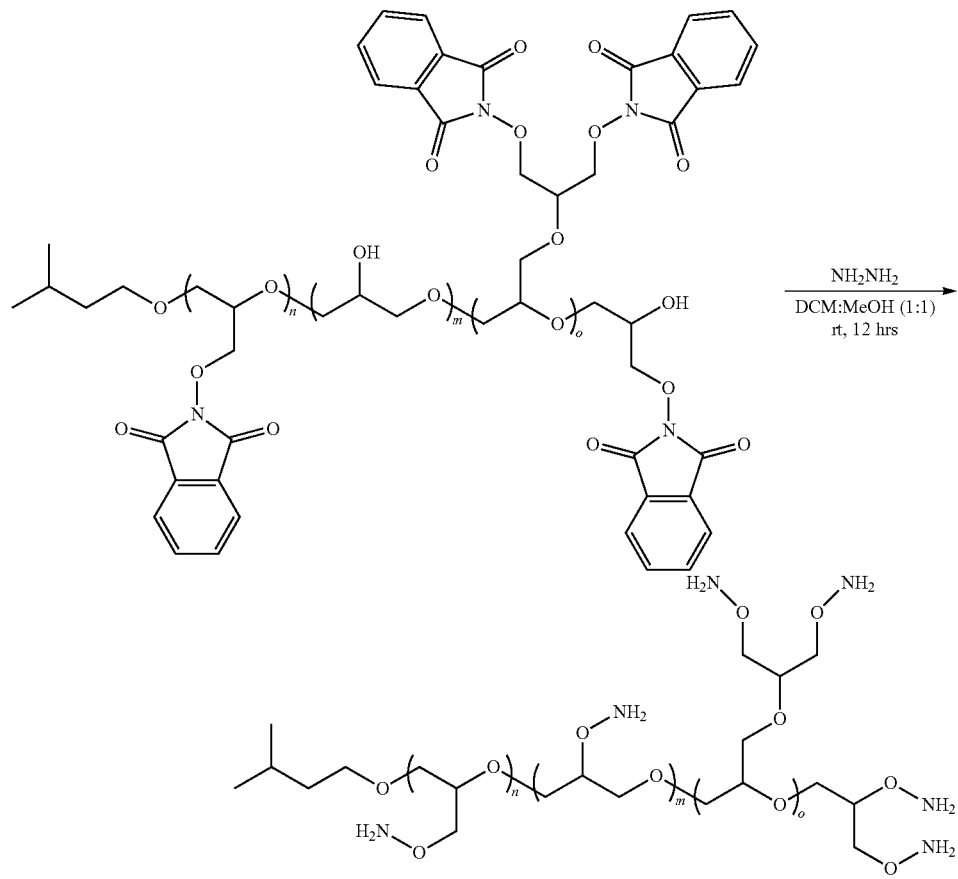

and add 50 mL methanol and then remove the solid compound by vacuum filtration. The residue crude product was precipitated in vigorously stirred acetone, which was then decanted to afford the pure viscous product.

(b) Preparation of Alkyne Functionalization of Polyglycidol (Method 2)

A dry flask was charged with propargyl bromide (0.36 equiv), polyglycidol hydroxyl group (1.00 equiv), dried potassium hydroxide pellets (1.08 equiv) in DMSO was stirred vigorously under nitrogen at room temperature for 12 h. The mixture was diluted with 50 mL methanol and the solid compound was removed by filtration. The residue crude product was precipitated in vigorously stirred acetone, which was then decanted to afford the pure viscous product. As would be appreciated by those of skill, the percentage of the amount of the azide group can be readily adjusted.

Figure 30:
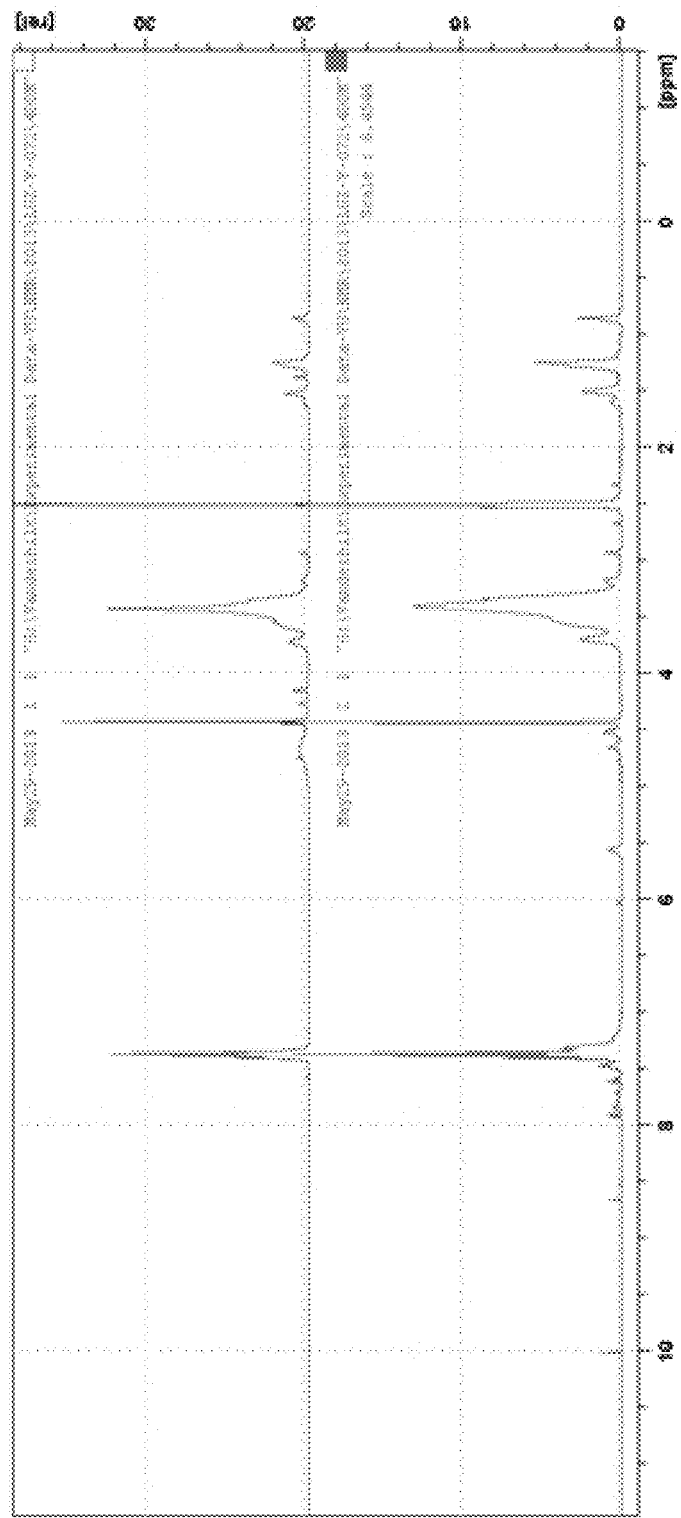
FIG. 30 shows a visual representation of NMR spectra of an exemplary glycidol polymer of the present invention.

(4) Preparation of Glycidol-Alkyne-Azide (A) Alkyne-Azide Click Reaction Catalyzed by Copper Foil Polyglycidol-alkyne (0.11 g) was dissolved in 1 mL DMSO in a microwave vial. Benzyl azide (0.061 mL) and Cu foil (0.25 g) was added into the vial followed by irradiation at 160° C. for 15 min. After completion of reaction, the reaction mixture was twice precipitated into acetone and subsequently dried for 12 hours under vacuum. The product was obtained as a highly viscous brown liquid. FIG. 30 shows the Click reaction via NMR.

(5) Preparation of Random Copolyesters of Δ-Valerolactone and 2-Oxepane-1,5-Dione

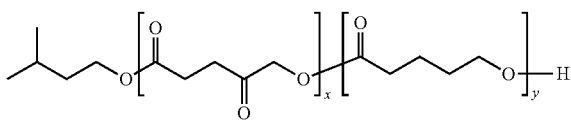

To a 10 mL round bottom flask equipped with a stir bar and an argon balloon was added isoamyl alcohol (37 µL, 300 µmol) and tin(II) trifluoromethanesulfonate (1.3 mg, 3 µmol). The mixture was stirred for 10 min. In a vial, flamed dried under vacuum, was added 2-oxepane-1,5-dione (242 mg, 1.89 mmol, synthesized according to literature procedure (Van der Ende, A. E. *J. Am Chem. Soc.* 2008, 130, 8706-13)), δ-valerolactone (702 µL, 7.57 mmol) and 2 mL of N,N-dimethylformamide. Once all the 2-oxepane-1,5-dione had dissolved, the solution was added to the reaction in one portion, and stirred at rt for 24 hrs. The reaction was then quenched with methanol and precipitated from hexanes to give the desired golden brown polymer (806 mg, 80%). $M_w$=1499 Da. $^1$H NMR (400 MHz, CDCl$_3$) δ 4.42-4.24 (br m, —C(O)CH$_2$CH$_2$O—), 4.14-3.95 (br m, —CH$_2$CH$_2$CH$_2$O—), 2.82-2.67 (br m, —CH$_2$C(O)CH$_2$—), 2.63-2.46 (br m, —OC(O)CH$_2$CH$_2$C(O)—), 2.38-2.18 (br m, —OC(O)CH$_2$CH$_2$CH$_2$—), 1.91-1.79 (br m, (CH$_3$)$_2$CH—), 1.72-1.52 (br m, —C(O)CH$_2$CH$_2$CH$_2$CH$_2$O—), 1.52-1.42 (br m, (CH$_3$)$_2$CHCH$_2$—), 0.91-0.82 (br m, (CH$_3$)$_2$CH—).

(6) Preparation of 4-Pentenoyl Polyglycidol

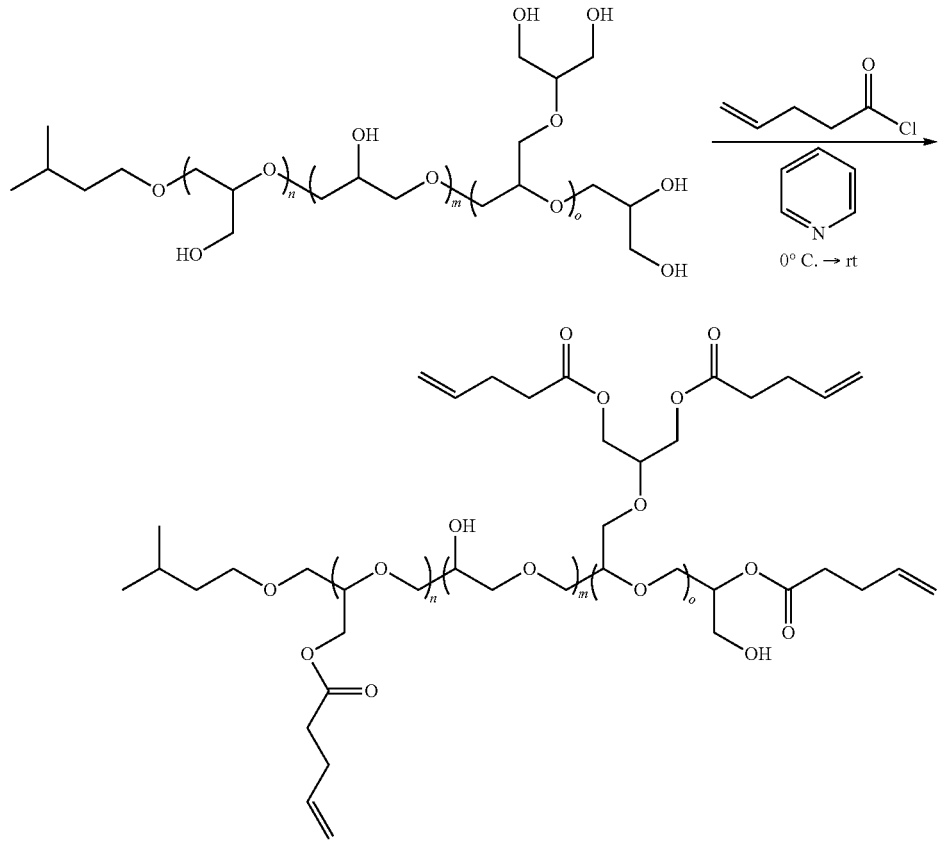

To a flame dried 25 mL round bottom flask equipped with a stir bar and argon balloon was added polyglycidol (1 g) and pyridine (2 mL, 25 mmol). The reaction mixture was stirred at rt for 10 min then cooled to 0° C. Pentenoyl chloride (607 μL, 5.50 mmol) was added dropwise to the reaction. The reaction was allowed to warm up to rt and stirred for 12 hrs. Reaction was then diluted with N,N-dimethylformamide (2 mL) and precipitated in a mixture of diethyl ether and ethyl acetate (1:1) to give the desired product as a pale yellow oil (520 mg, 52%). $^1$H NMR (400 MHz, CD$_3$OD) δ 6.07-5.70 (br m, CH$_2$=CH—), 5.21-5.01 (br m, CH$_2$=CH—), 4.96-4.50 (br s, —OH), 4.40-4.03 (br m, —CHCH$_2$OC(O)CH$_2$—), 4.02-3.86 (br m, —CHCH$_2$OH), 3.82-3.22 (br m, —OCHCH$_2$CHO—), 2.60-2.23 (br m, —C(O)CH$_2$CH$_2$CH=CH$_2$), 1.71-1.66 (br m, (CH$_3$)$_2$CH—), 1.50-1.39 (br m, (CH$_3$)$_2$CHCH$_2$—), 0.95-0.81 (br m, (CH$_3$)$_2$CH—). As would be appreciated by those of skill, the amount and type of allyl group can be readily adjusted.

(7) Preparation of 3-Mercaptopropanoyl Polyglycidol

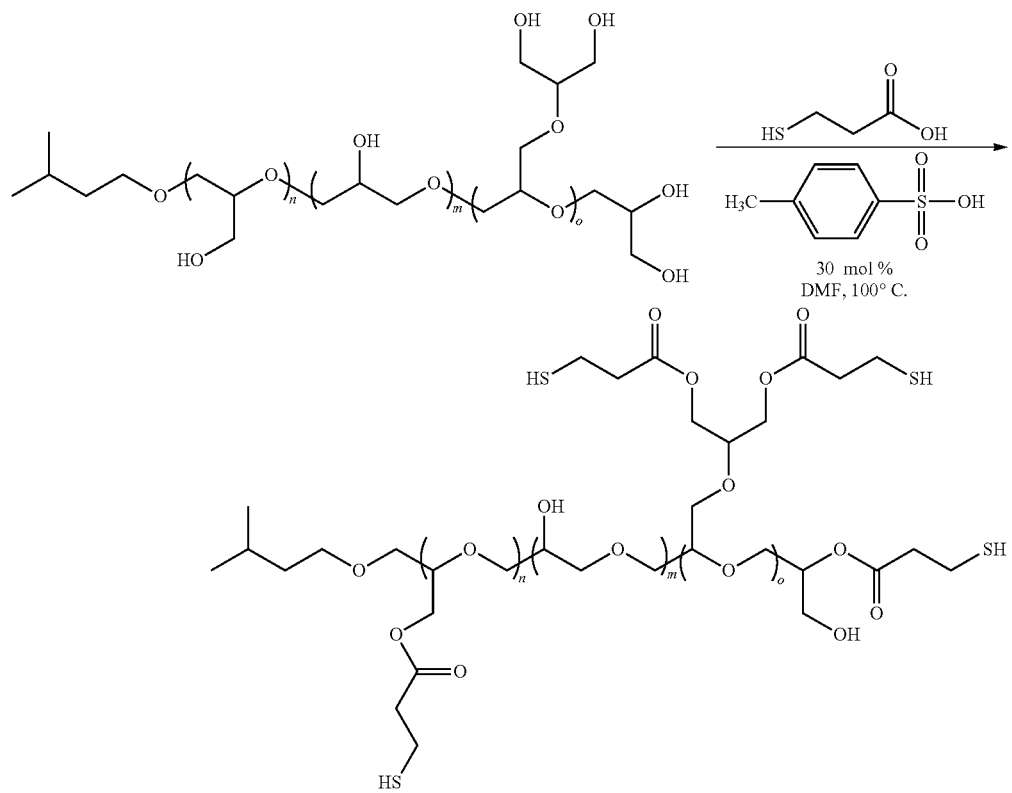

To a 25 mL round bottom flask, flame dried and equipped with a stir bar and argon balloon, was added a solution of polyglycidol (1 g) in N,N-dimethylformamide (1 mL), 3-mercaptopropionic acid (1.4 mL, 16.6 mmol), and p-Toluenesulfonic acid (34 mg, 0.2 mmol). The mixture was stirred at 100° C. for 24 hrs. The mixture was diluted with N,N-dimethylformamide (2 mL), and precipitated in ether. The product was further purified by size exclusion chromatography (sephadex LH-20 in methanol) to yield the desired polymer (200 mg). $^1$H NMR (400 MHz, CD$_3$OD) δ 4.93 (br s, —OH), 4.46-4.08 (br m, —CHCH$_2$OC(O)CH$_2$—), 4.01-3.81 (br m, —CHCH$_2$OH), 3.85-3.41 (br m, —OCHCH$_2$CHO—), 2.81-2.63 (br m, —C(O)CH$_2$CH$_2$SH), 1.78-1.66 (br m, (CH$_3$)$_2$CH—), 1.52-1.42 (br m, (CH$_3$)$_2$CHCH$_2$—), 0.98-0.87 (br m, (CH$_3$)$_2$CH—). As would be appreciated by those of skill, the amount and type of mercapto group can be readily adjusted.

REFERENCES

1. Wilms, D. and H. Frey, *Advanced control over glycidol polymerization: Hyperbranched polyglycerols via macro-initiators.* Abstracts of Papers of the American Chemical Society, 2009. 237.
2. Haag, R., A. Sunder, and J. F. Stumbe, *An approach to glycerol dendrimers and pseudo-dendritic polyglycerols.* Journal of the American Chemical Society, 2000. 122(12): p. 2954-2955.
3. Zhang, J. G., et al., *Conjugation to hyperbranched polyglycerols improves RGD-mediated inhibition of platelet function in vitro.* Bioconjugate Chemistry, 2008. 19(6): p. 1241-1247.
4. Sunder, A., et al., *Controlled synthesis of hyperbranched polyglycerols by ring-opening multibranching polymerization.* Macromolecules, 1999. 32(13): p. 4240-4246.
5. Calderon, M., et al., *Dendritic Polyglycerols for Biomedical Applications.* Advanced Materials, 2010. 22(2): p. 190-218.
6. Mendrek, A., et al., *Amphiphilic behaviour of poly(glycidol)-based macromonomers and its influence on homopolymerisation in water and in water/benzene mixture.* Polymer, 2010. 51(2): p. 342-354.
7. van der Ende, A. E., E. J. Kravitz, and E. Harth, *Approach to formation of multifunctional polyester particles in controlled nanoscopic dimensions.* Journal of the American Chemical Society, 2008. 130(27): p. 8706-8713.

8. van der Ende, A. E., et al., *"Click" Reactions: Novel Chemistries for Forming Well-defined Polyester Nanoparticles*. Macromolecules, 2010. 43(13): p. 5665-5671.
9. van der Ende, A. E., et al., *Linear release nanoparticle devices for advanced targeted cancer therapies with increased efficacy*. Polymer Chemistry, 2010. 1(1): p. 93-96.
10. van der Ende, A., et al., *Tailored polyester nanoparticles: post-modification with dendritic transporter and targeting units via reductive amination and thiol-ene chemistry*. Soft Matter, 2009. 5(7): p. 1417-1425.
11. Zhang, X. J., et al., *beta-Cyclodextrin grafting hyperbranched polyglycerols as carriers for nasal insulin delivery*. Carbohydrate Polymers, 2011. 84(4): p. 1419-1425.
12. Mugabe, C., et al., *Development and in vitro characterization of paclitaxel and docetaxel loaded into hydrophobically derivatized hyperbranched polyglycerols*. International Journal of Pharmaceutics, 2011. 404(1-2): p. 238-249.
13. Mugabe, C., et al., *In Vivo Evaluation of Mucoadhesive Nanoparticulate Docetaxel and Paclitaxel Loaded Hydrophobically Derivatized Hyperbranched Polyglycerols for Intravesical Bladder Cancer Therapy*. European Urology Supplements, 2011. 10(2): p. 166-167.
14. Mugabe, C., et al., *Paclitaxel incorporated in hydrophobically derivatized hyperbranched polyglycerols for intravesical bladder cancer therapy*. Bju International, 2009. 103(7): p. 978-986.
15. Burakowska, E., S. C. Zimmerman, and R. Haag, *Photoresponsive Crosslinked Hyperbranched Polyglycerols as Smart Nanocarriers for Guest Binding and Controlled Release*. Small, 2009. 5(19): p. 2199-2204.
16. Haag, R., et al., *Polymeric nanocapsules based on core-shell-type architectures in hyperbranched polyglycerols*. Abstracts of Papers of the American Chemical Society, 2001. 221: p. U363-U364.
17. Ye, L., et al., *Synthesis and Characterization of Carboxylic Acid Conjugated, Hydrophobically Derivatized, Hyperbranched Polyglycerols as Nanoparticulate Drug Carriers for Cisplatin*. Biomacromolecules, 2011. 12(1): p. 145-155.
18. Wang, S. X., et al., *Growing hyperbranched polyglycerols on magnetic nanoparticles to resist nonspecific adsorption of proteins*. Colloids and Surfaces B-Biointerfaces, 2008. 67(1): p. 122-126.
19. Sunder, A., H. Frey, and R. Mulhaupt, *Hyperbranched polyglycerols by ring-opening multibranching polymerization*. Macromolecular Symposia, 2000. 153: p. 187-196.
20. Steinhilber, D., et al., *Hyperbranched polyglycerols on the nanometer and micrometer scale*. Biomaterials, 2011. 32(5): p. 1311-1316.
21. Wilms, D., S. E. Stiriba, and H. Frey, *Hyperbranched Polyglycerols: From the Controlled Synthesis of Biocompatible Polyether Polyols to Multipurpose Applications*. Accounts of Chemical Research, 2010. 43(1): p. 129-141.
22. Khan, M. and W. T. S. Huck, *Hyperbranched polyglycidol on Si/SiO2 surfaces via surface-initiated polymerization*. Macromolecules, 2003. 36(14): p. 5088-5093.
23. Tokar, R., et al., *Cationic Polymerization of Glycidol—Coexistence of the Activated Monomer and Active Chain-End Mechanism*. Macromolecules, 1994. 27(2): p. 320-322.
24. Sunder, A., et al., *Copolymers of glycidol and glycidyl ethers: Design of branched polyether polyols by combination of latent cyclic AB(2) and ABR monomers*. Macromolecules, 2000. 33(21): p. 7682-7692.
25. Dworak, A., W. Walach, and B. Trzebicka, *Cationic Polymerization of Glycidol—Polymer Structure and Polymerization Mechanism*. Macromolecular Chemistry and Physics, 1995. 196(6): p. 1963-1970.
26. Hang, J. G. Z., et al., *RGD-substituted high molecular weight hyper-branched polyglycerols (HPG) are effective platelet inhibitors*. Blood, 2007. 110(11): p. 281 A-281A.
27. Mugabe, C., et al., *In Vitro and In Vivo Evaluation of Intravesical Docetaxel Loaded Hydrophobically Derivatized Hyperbranched Polyglycerols in an Orthotopic Model of Bladder Cancer*. Biomacromolecules, 2011. 12(4): p. 949-960.
28. Rangelov, S., et al., *Hydrodynamic behavior of high molar mass linear polyglycidol in dilute aqueous solution*. Journal of Physical Chemistry B, 2007. 111(38): p. 11127-11133.
29. Gervais, M., et al., *Linear High Molar Mass Polyglycidol and its Direct a-Azido Functionalization*. Macromolecular Symposia, 2011. 308(1): p. 11.
30. Debaig, C., T. Benvegnu, and D. Plusquellec, *Synthesis of linear and cyclic polyglycerols. Polyglyceryled surfactants: synthesis and characterization*. Ocl-Oleagineux Corps Gras Lipides, 2002. 9(2-3): p. 155-162.
31. Gervais, M., et al., *Synthesis of Linear High Molar Mass Glycidol-Based Polymers by Monomer-Activated Anionic Polymerization*. Macromolecules, 2010. 43(4): p. 1778-1784.
32. Alconcel, S. N. S., A. S. Baas, and H. D. Maynard, *FDA-approved poly(ethylene glycol)-protein conjugate drugs*. Polymer Chemistry, 2011. 2(7): p. 1442-1448.
33. Gunasekaran, K., et al., *Conjugation of siRNA with Comb-Type PEG Enhances Serum Stability and Gene Silencing Efficiency*. Macromolecular Rapid Communications, 2011. 32(8): p. 654-659.
34. Boyer, C., et al., *Well-defined protein-polymer conjugates via in situ RAFT polymerization*. Journal of the American Chemical Society, 2007. 129(22): p. 7145-7154.
35. Parrott, M. C. and J. M. DeSimone, *Drug Delivery Relieving Pegylation*. Nature Chemistry, 2012. 4(1): p. 13-14.
36. Wilms, D., et al., *Hyperbranched PEG by Random Copolymerization of Ethylene Oxide and Glycidol*. Macromolecular Rapid Communications, 2010. 31(20): p. 1811-1815.
37. Fischer, W., et al., *Dendritic Polyglycerols with Oligoamine Shells Show Low Toxicity and High siRNA Transfection Efficiency in Vitro*. Bioconjugate Chemistry, 2010. 21(10): p. 1744-1752.
38. Maminski, M. L., et al., *Fast-curing polyurethane adhesives derived from environmentally friendly hyperbranched polyglycerols—The effect of macromonomer structure*. Biomass & Bioenergy, 2011. 35(10): p. 4461-4468.
39. Hamilton, S. K., et al., *Effective delivery of IgG-antibodies into infected cells via dendritic molecular transporter conjugate IgGMT*. Molecular Biosystems, 2008. 4(12): p. 1209-1211.
40. Sizovs, A., et al., *Carbohydrate Polymers for Nonviral Nucleic Acid Delivery*. Topics in Current Chemistry, 2010. 296(296): p. 131-190.
41. J. Chem. Soc., 1998. Perkin Trans 1: p. 2771.

What is claimed is:

1. A method for making a polymer, the method comprising polymerizing glycidol to form the polymer, the polymer comprising repeating units selected from:

A1

[structure]

A2

[structure]

B1

[structure], and

B2

[structure], wherein R⁰ is selected from H, alkyl, NH$_2$, and R$^1$;
wherein R$^1$ comprises a crosslinking functionality; and
wherein the ratio of (A1+A2):(B1+B2) is greater than 5.

2. The method of claim 1, wherein polymerizing glycidol is performed at a temperature ranging from −80° C. to 50° C.

3. The method of claim 1, further comprising crosslinking the polymer with crosslinks.

4. The method of claim 3, wherein the crosslinks comprise one or more of $-\!\!+\!CH_2\!+\!\!\!-_{2\text{-}30}$, [structures with subscripts 0-5, 0-8, 0-5, 0-5, 0-5], and wherein at least one of

[structures with subscripts 0-5, 0-8, 0-5, 0-5, 0-5], and is not 0.

5. The method of claim 1, wherein the ratio of (A1+A2):(B1+B2) is greater than 10.

6. A method for making a polymer, the method comprising polymerizing glycidol to form the polymer, the polymer comprising at least one repeating unit formed from a monomer selected from:

[structures of monomers]

or a combination thereof.

7. The method of claim 6, wherein polymerizing glycidol is performed at a temperature ranging from −80° C. to 50° C.

8. The method of claim 6, further comprising crosslinking the polymer with crosslinks.

9. The method of claim 8, wherein the crosslinks comprise one or more of:

$-\!\!+\!CH_2\!+\!\!\!-_{2\text{-}30}$, [structures with subscripts 0-5, 0-8, 0-5, 0-5, 0-5], and wherein at least one of

[structures with subscripts 0-5, 0-8, 0-5, 0-5], and

-continued

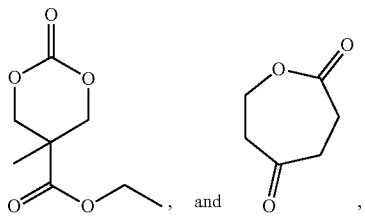

is not 0.

10. A method of forming a nanoparticle comprising:
polymerizing glycidol to form a polymer, the polymer comprising at least one repeating unit formed from a monomer selected from:

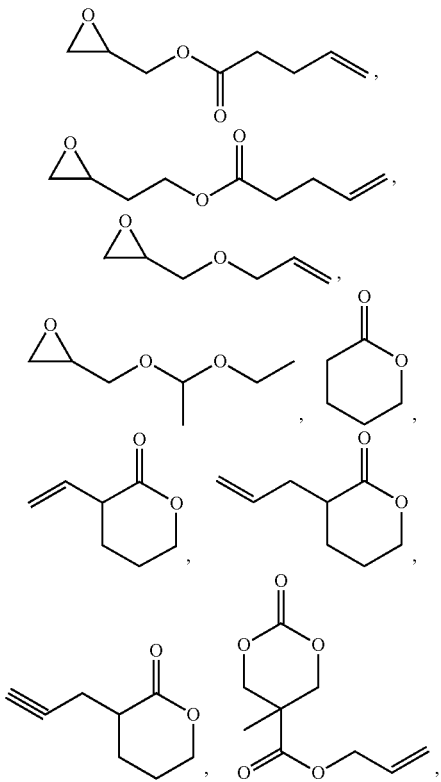

-continued

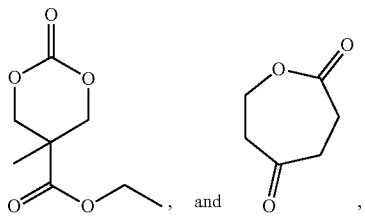, and or a combination thereof; and crosslinking the polymer with crosslinks, wherein the crosslinks comprise:

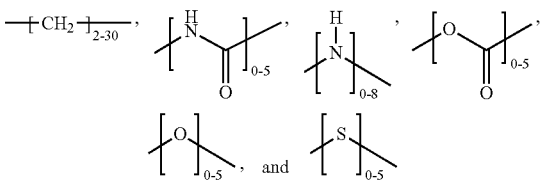

wherein at least one of

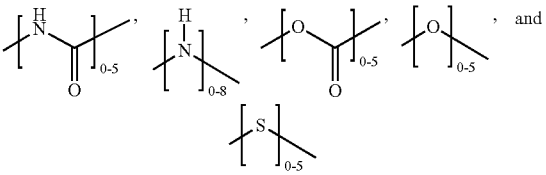

is not 0, thereby forming the nanoparticle.

11. The method of claim 10, wherein polymerizing glycidol is performed at a temperature ranging from −80° C. to 50° C.

* * * * *